US009295650B2

(12) United States Patent
Neumann et al.

(10) Patent No.: US 9,295,650 B2
(45) Date of Patent: Mar. 29, 2016

(54) FUNCTIONAL, CROSS-LINKED NANOSTRUCTURES FOR TANDEM OPTICAL IMAGING AND THERAPY

(75) Inventors: William L. Neumann, Kirkwood, MO (US); Richard B. Dorshow, St. Louis, MO (US); John N. Freskos, Clayton, MO (US); Karen L. Wooley, College Station, TX (US); Nam S. Lee, Concord, MA (US); Yun Lin, Concord, MA (US); Guorong Sun, Bryan, TX (US)

(73) Assignees: Mallinckrodt LLC, Hazelwood, MO (US); The Texas A&M University System, College Station, TX (US); Washington University, St. Louis, MI (US)

( * ) Notice: Subject to any disclaimer, the term of this patent is extended or adjusted under 35 U.S.C. 154(b) by 54 days.

(21) Appl. No.: 13/697,149

(22) PCT Filed: Nov. 17, 2011

(86) PCT No.: PCT/US2011/036392
§ 371 (c)(1),
(2), (4) Date: Dec. 13, 2012

(87) PCT Pub. No.: WO2011/143524
PCT Pub. Date: Nov. 17, 2011

(65) Prior Publication Data
US 2013/0137976 A1 May 30, 2013

Related U.S. Application Data

(60) Provisional application No. 61/334,698, filed on May 14, 2010.

(51) Int. Cl.
A61K 49/00 (2006.01)
A61K 9/14 (2006.01)
(Continued)

(52) U.S. Cl.
CPC .............. *A61K 9/146* (2013.01); *A61K 9/0092* (2013.01); *A61K 9/1075* (2013.01);
(Continued)

(58) Field of Classification Search
None
See application file for complete search history.

(56) References Cited

U.S. PATENT DOCUMENTS

| 4,548,907 A | 10/1985 | Seitz et al. |
| 5,429,826 A | 7/1995 | Nair et al. |

(Continued)

FOREIGN PATENT DOCUMENTS

| JP | 60138541 | 7/1985 |
| JP | 2003015294 | 1/2003 |

(Continued)

OTHER PUBLICATIONS

V. L. Alexeev et al., "High Ionic Strength Glucose-Sensing Photonic Crystal," Anal. Chem. 75:2316-2323, 2003.
(Continued)

*Primary Examiner* — Paul Dickinson

(57) ABSTRACT

The present invention provides optical agents comprising optically functional cross linked supramolecular structures and assemblies useful for tandem optical imaging and therapy. Supramolecular structures and assemblies of the present invention include optically functional shell-cross linked micelles wherein optical functionality is achieved via incorporation of one or more linking groups that include one or more photoactive moieties. The present invention further includes imaging and therapeutic methods using one or more optical agents of the present invention including optically functional shell cross-linked micelles having an associated therapeutic agent.

20 Claims, 24 Drawing Sheets

(51) Int. Cl.
| | |
|---|---|
| *A61K 9/00* | (2006.01) |
| *A61K 9/107* | (2006.01) |
| *A61K 9/51* | (2006.01) |
| *A61K 31/20* | (2006.01) |
| *A61K 31/70* | (2006.01) |
| *A61K 38/16* | (2006.01) |
| *A61K 38/22* | (2006.01) |
| *A61K 39/395* | (2006.01) |
| *A61M 5/00* | (2006.01) |

(52) U.S. Cl.
CPC ............ *A61K 9/5138* (2013.01); *A61K 9/5192* (2013.01); *A61K 31/20* (2013.01); *A61K 31/70* (2013.01); *A61K 38/16* (2013.01); *A61K 38/22* (2013.01); *A61K 39/395* (2013.01); *A61K 49/0021* (2013.01); *A61K 49/0054* (2013.01); *A61K 49/0082* (2013.01); *A61K 49/0093* (2013.01); *A61M 5/007* (2013.01)

(56) References Cited

U.S. PATENT DOCUMENTS

| | | | |
|---|---|---|---|
| 5,562,099 | A | 10/1996 | Cohen et al. |
| 6,007,845 | A | 12/1999 | Domb et al. |
| 6,221,397 | B1 | 4/2001 | Russell-Jones et al. |
| 6,383,500 | B1 | 5/2002 | Wooley et al. |
| 6,540,981 | B2 | 4/2003 | Klaveness et al. |
| 6,806,089 | B1 | 10/2004 | Lakowicz et al. |
| 7,026,342 | B2 | 4/2006 | Wagle et al. |
| 7,166,306 | B2 | 1/2007 | Chen et al. |
| 7,316,899 | B2 | 1/2008 | McDevitt et al. |
| 7,332,527 | B2 | 2/2008 | Bronich et al. |
| 7,531,191 | B2 | 5/2009 | Zion et al. |
| 7,550,441 | B2 | 6/2009 | Farokhzad et al. |
| 7,638,558 | B2 | 12/2009 | Breitenkamp et al. |
| 7,682,603 | B2 | 3/2010 | Hammer et al. |
| 2003/0064422 | A1 | 4/2003 | McDevitt et al. |
| 2003/0099574 | A1 | 5/2003 | Bentsen et al. |
| 2004/0005582 | A1 | 1/2004 | Shipwash |
| 2004/0202719 | A1 | 10/2004 | Zion et al. |
| 2005/0019265 | A1 | 1/2005 | Hammer et al. |
| 2006/0269479 | A1 | 11/2006 | Colton et al. |
| 2008/0063621 | A1 | 3/2008 | Gyongyossy-Issa et al. |
| 2008/0081074 | A1 | 4/2008 | Gu et al. |
| 2008/0308744 | A1 | 12/2008 | Frangioni et al. |
| 2009/0061010 | A1 | 3/2009 | Zale et al. |
| 2009/0061473 | A1 | 3/2009 | Saxena et al. |
| 2010/0009926 | A1 | 1/2010 | Kim et al. |
| 2010/0056392 | A1 | 3/2010 | Greving et al. |
| 2010/0092536 | A1 | 4/2010 | Hunter et al. |
| 2010/0311903 | A1 | 12/2010 | Rajagopalan |

FOREIGN PATENT DOCUMENTS

| | | |
|---|---|---|
| WO | WO 97/49736 | 12/1997 |
| WO | WO 01/87227 | 11/2001 |
| WO | WO 02/053158 | 7/2002 |
| WO | WO 03/066712 | 8/2003 |
| WO | WO 2005/041884 | 5/2005 |
| WO | WO 2005/082423 | 9/2005 |
| WO | WO 2006/044716 | 4/2006 |
| WO | WO 2006/054288 | 5/2006 |
| WO | WO 2006/107903 | 10/2006 |
| WO | WO 2006/138479 | 12/2006 |
| WO | WO 2007/106142 | 9/2007 |
| WO | WO 2007/133807 | 11/2007 |
| WO | WO 2007/149479 | 12/2007 |
| WO | WO 2008/001575 | 1/2008 |
| WO | WO 2008/064274 | 5/2008 |
| WO | WO 2008/105773 | 9/2008 |
| WO | WO 2008/108941 | 9/2008 |
| WO | WO 2008/108944 | 9/2008 |
| WO | WO 2008/124632 | 10/2008 |
| WO | WO 2008/134731 | 11/2008 |
| WO | WO 2009/061473 | 5/2009 |
| WO | WO 2010/024783 | 3/2010 |
| WO | WO 2010/033220 | 3/2010 |
| WO | WO 2010/042555 | 4/2010 |

OTHER PUBLICATIONS

M. Barzoukas et al., "Molecular engineering of push-pull dipolar and quadrupolar molecules for two-photon absorption: A multivalence-bond states approach," J. Chem. Phys. 113:3951-3959, 2000.

A. Baugher et al. "Location of fluorotryptophan sequestered in an amphiphilic nanoparticle by rotational-echo double-resonance NMR," Biophysical Journal 75:2574-2576, Nov. 1998.

D. Benoit et al., "Development of a universal alkoxyamine for "living" free radical polymerizations," J. Am. Chem. Soc. 121:3904-3920, 1999.

B. P. Binks et al., "Temperature-Induced Inversion of Nanoparticle-Stabilized Emulsions," Angew. Chem. Int. Ed. 44:4795-4798, 2005.

E. Blanco et al., "Multifunctional micellar nanomedicine for cancer therapy," Exp. Biol. Med. 234:123-131, 2009.

J. Chan et al., "PLGA-lecithin-PEG coreshell nanoparticles for controlled drug delivery," Biomaterials 30:1627-1634, 2009.

H. Cui et al., "Block copolymer assembly via kinetic control," Science. 317:647-650, 2007.

Dorshow et al., "New optical probes for the continuous monitoring of renal function," Proceedings of SPIE 6867, 2008, 12 pages.

T. Etrych et al., "New HPMA copolymers containing doxorubicin bound via pH-sensitive linkage: Synthesis and preliminary in vitro and in vivo biological properties," J Controlled Release 73(1):89-102, May 18, 2001, Abstract Only.

M. Gindy et al., "Multifunctional nanoparticles for imaging, delivery and targeting in cancer therapy," Expert Opin. Drug Deliv. 6(8):865-878, 2009.

P. Greenspan et al., "Spectrofluorometric studies of the lipid probe, vile red," Journal of Lipid Research 26:781-789, 1985.

F. Gu et al., "Precise engineering of targeted nanoparticles using self-assembled biointegrated block copolymers," PNAS 105(7):2586-2591, Feb. 19, 2008.

I. W. Hamley, "Nanostructure fabrication using block Copolymers," Nanotechnology 14:R39-R54, 2003.

C.-K. Huang et al., "Multifunctional micelles for cancer cell targeting, distribution imaging, and anticancer drug delivery," Advanced Functional Materials 17:2291-2297, 2007.

H. Huang et al., "Hydrogel-Coated Glassy Nanospheres: A Novel Method for the Synthesis of Shell Cross-Linked Knedels," J. Am. Chem. Soc. 119:11653-11659, 1997.

A. Ievins et al., "Synthesis of core functionalized polymer micelles and shell cross-linked nanoparticles," Macromolecules 41:2998-3006, 2008.

R. Iha et al., "Applications of orthogonal "click" chemistries in the synthesis of functional soft materials," Chem. Rev. 109:5620-5686, 2009.

International Search Report, International Application No. PCT/US2008/012575, Sep. 11, 2009, 4 pages.

International Search Report, International Application No. PCT/US2011/036411, Sep. 19, 2011, 2 pages.

International Search Report, International Application No. PCT/US2011/036392, Aug. 20, 2012, 3 pages.

F. Jaffer et al., "Optical and multimodality molecular imaging insights into atherosclerosis," Arterioscler Thromb. Vasc. Biol. 29(7):1017-1024, 2009.

W. Jiang et al., "Nanoparticle-mediated cellular response is size-dependent," Nature Nanotechnology 3:145-150, Mar. 2008.

M. Joralemon et al., "Antigen-decorated shell cross-linked nanoparticles: Synthesis, characterization, and antibody interactions," Bioconjugate Chem. 16:1246-1256, 2005.

M. Joralemon et al., "Shell Click-Crosslinked (SCC) Nanoparticles: A New Methodology for Synthesis and Orthogonal Functionalization,"J. Am. Chem. Soc. 127:16892-16899, 2005.

C. Khemtong et al., "Polymeric nanomedicine for cancer MR imaging and drug delivery," Chem. Commun. 24:3477-3640, Jun. 28, 2009.

(56) References Cited

OTHER PUBLICATIONS

J. Kim et al., "Multifunctional nanostructured materials for multimodal imaging, and simultaneous imaging and therapy," Chem. Soc. Rev. 38:372-390, 2009.

J.-H. Kim et al., "Polymers for bioimaging," Prog. Polym. Sci. 32:1031-1053, 2007.

J. Kim et al., "Self-assembling of aminopyrazine fluorescent dyes and their solid state spectra, part 2," Dyes and Pigments 41:183-191, 1999.

O. Koo et al., "Role of nanotechnology in targeted drug delivery and imaging: A concise review," Nanomedicine: Nanotechnology, Biology, and Medicine 1:193-212, 2005.

N. Lee et al., "Functionalized, crosslinked nanostructures for tandem optical imaging and therapy," Poster Presentation No. 0801B, WMIC Meeting, Sep. 10, 2010.

N. Lee et al., "Influence of Nanostructure Morphology on Host Capacity and Kinetics of Guest Release," Small 7(14):1998-2003, 2011.

N. Lee et al., "Tunable dual-emitting shell-crosslinked nano-objects as single-component ratiometric pH-sensing materials," J. Mater. Chem. 21:14193-14202, 2011.

N. Lee et al., "Aqueous-only, pH-induced nanoassembly of dual pKa-driven contraphilic block copolymers," Chem. Comm. (Camb) 42:5339-5341, Nov. 14, 2008.

N. Lee et al., "Photonic shell-crosslinked nanoparticle probes for optical imaging and monitoring," Adv. Matter 21(13):1344-1348, Apr. 6, 2009.

N. Lee et al., "Photonic shell-crosslinked nanoparticle probes for optical imaging and monitoring," Adv. Matter 20:1-5, 2009.

N. Lee et al., "Photonic shell-crosslinked nanoparticles probes for optical imaging and monitoring," Polymer Preprints 49(1):1051-1052, Apr. 1, 2008.

Y. Li et al., "Shell crosslinked nanoparticles: A progress report of their design for drug delivery," Chapter 16, In: Nanotechnology in Therapeutics: Current Technology and Applications, Horizon Bioscience, Norfolk UK, 2007, pp. 381-407.

Z. Li et al., "Multicompartment Micelles from ABC Miktoarm Stars in Water," Science 306:98-101, 2004.

J. Liu et al., "Nanostructured materials designed for cell binding and transduction," Biomacromolecules 2:362-368, 2001.

S. Liu et al., "Polymeric Surfactants for the New Millennium: A pH-Responsive, Zwitterionic, Schizophrenic Diblock Copolymer," Angew. Chem. Int. Ed. 41:1413-1416, 2002.

Q. Ma et al., "Environmentally-responsive, entirely hydrophilic, shell-cross-linked (SCK) nanoparticles," Nano Lett. 1(11), 651-655, 2001.

R. K. O'Reilly et al., "Cross-linked block copolymer micelles: functional nanostructures of great potential and versatility," Chem. Soc. Rev. 35:1068-1083, 2006.

K. Qi et al., "Determination of the Bioavailability of Biotin Conjugated onto Shell Cross-Linked (SCK) Nanoparticles," J. Am. Chem. Soc. 126:6599-6607, 2004.

D. Peer et al., "Nanocarriers as an emerging platform for cancer therapy," Nature Nanotechnology 2:751-760, Dec. 2007.

H. Peng et al., "Core-cross-linked polymer micelles via living polymerizations," Materials Science and Engineering C 29:746-750, 2009.

E. Read et al., "Recent advances in shell cross-linked micelles," Chem. Commun. 3021-3035, 2007.

A. Rosier et al., "Advanced drug delivery devices via self-assembly of amphiphilic block copolymers," Advanced Drug Delivery Reviews 53:95-108, 2001.

R. Rossin et al., "Cu-labeled folate-conjugated shell cross-linked nanoparticles for tumor imaging and radiotherapy: Synthesis, radiolabeling, and biological evaluation," J. Nuclear Med. 46(7):1210-1218, Jul. 2005.

H. K. Sajja et al., "Development of multifunctional nanoparticles for targeted drug delivery and non-invasive imaging of therapeutic effect," Current Drug Delivery Technologies 6:43-51, 2009.

G. Sun et al., "Construction of functionalizable, crosslinked nanostructures," 237th ACS National Meeting, Salt Lake City, UT, Mar. 23, 2009, Abstract.

G. Sun et al., "A fundamental investigation of cross-linking efficiencies within discrete nanostructures, using the cross-linker as a reporting molecule," Soft Matter 5:3422-3429, 2009 (Web release Aug. 17, 2009).

Sun "Multicompartment Polymer Nanostructures with Ratiometric Dual-Emission pH-Sensitivity," J. Am. Chem. Soc. 133:8534-8543, 2011.

K. B. Thurmond II et al., "Packaging of DNA by shell crosslinked nanoparticles," Nucleic Acid Research 27(14):2966-2971, 1999.

A. Walther et al., "Multiple Morphologies, Phase Transitions, and Cross-Linking of Crew-Cut Aggregates of Polybutadiene-block-poly(2-vinylpyridine) Diblock Copolymers," Macromolecules 41:3254-3260, 2008.

J. Xu et al., "Labeling of polymer nanostructures for medical imaging: Importance of cross-linking extent, spacer length, and charge density," Macromolecules 40:2971-2973, 2007.

X. Xu et al., "Enhanced stability of core-surface cross-linked micelles fabricated from amphiphilic brush copolymers," Biomacromolecules 5:1736-1744, 2004.

X. Xu et al., "Polymerized PolyHEMA Photonic Crystals: pH and Ethanol Sensor Materials," J. Am. Chem. Soc. 130:3113-3119, 2008.

K. Zhang et al., "Folate-mediated cell uptake of shell-crosslinked spheres and cylinders," J. Polymer Science: Part A: Polymer Chemistry 46:7578-7583, 2008.

K. Zhang et al., "Shape effects of nanoparticles conjugated with cell-penetrating peptides (HIV Tat PTD) on CHO cell uptake," Bioconjugate Chem. 19:1880-1887, 2008.

Q. Zhang et al., "Shell Cross-Linked Nanoparticles Containing Hydrolytically Degradable, Crystalline Core Domains," J. Am. Chem. Soc. 122:3642-3651, 2000.

FUNCTIONAL, CROSS-LINKED NANOSTRUCTURES FOR TANDEM OPTICAL IMAGING AND THERAPY

CROSS-REFERENCE TO RELATED APPLICATIONS

This application is a U.S. National Stage Application under 35 U.S.C. §371 of International Application No. PCT/US11/36392, filed May 13, 2011, which claims the benefit of U.S. provisional patent application Ser. No. 61/334,698, filed May 14, 2010, all of which are incorporated by reference herein.

BACKGROUND OF THE INVENTION

Self-assembled nanostructures are a class of nanomaterials having chemical and physical properties that are potentially beneficial for biomedical applications. Amphiphilic polymer micelle supramolecular structures, for example, have been proposed as a versatile nanomaterials platform for encapsulating, solubilizing, and facilitating delivery of poorly water soluble drugs, including chemotherapeutic agents. Incorporation of targeting ligands into amphiphilic polymer micelle supramolecular structures has promise to provide an effective route for targeted delivery of pharmaceuticals to specific cell types, tissues and organs. Use of micelle supramolecular structures for drug formulation and delivery applications is currently the subject of considerable research.

Polymer micelle supramolecular structures are typically formed via entropically driven self-assembly of amphiphilic polymers in a solution environment. For example, when block copolymers, having spatially segregated hydrophilic and hydrophobic domains are provided in aqueous solution at a concentration above critical micelle concentration (CMC) the polymers aggregate and self assemble such that hydrophobic domains form a central hydrophobic core and hydrophilic domains self assemble into an exterior hydrophilic corona region exposed to the aqueous phase. The core-corona structure of amphiphilic polymer micelles provides useful physical properties, as the hydrophobic core provides a shielded phase capable of solubilizing hydrophobic molecules, and the exterior corona region is at least partially solvated, thus imparting colloidal stability to these nanostructures.

A number of amphiphilic polymer systems, including block copolymers and cross linked block copolymer assemblies, have been specifically engineered and developed for biomedical applications, such as drug formulation and delivery applications. The following references provide examples of amphiphilic polymer drug delivery systems, including block copolymer drug delivery systems, which are hereby incorporated by reference in their entireties: (1) Li, Yali; Sun, Guorong; Xu, Jinqi; Wooley, Karen L., Shell Crosslinked Nanoparticles: a Progress Report on their Design for Drug Delivery; Nanotechnology in Therapeutics (2007), 381-407; (2) Qinggao Ma, Edward E. Remsen, Tomasz, Kowalewski, Jacob Schaefer, Karen Wooley, "Environmentally-responsive, Entirely, Hydrophilic, Shell Cross-linked (SCK) Nanoparticles" Nano Lett. 2001, 1, 651; (3) Jones, M.-C.; Leroux J.-C. "Polymeric Micelles: A New Generation of Colloidal Drug Carriers" Eur. J. Pharm. Biopharm. 1999, 48, 101-111; and (4) Kwon, G. S.; Naito, M.; Kataoka, K.; Yokoyama, M.; Sakurai, Y.; Okano, T. "Block Copolymer Micelles as Vehicles for Hydrophobic Drugs" Colloids and Surfaces, B: Biointerfaces 1994, 2, 429-34.

Although polymer systems have been suggested for drug delivery systems, the use of polymer supramolecular assemblies for tandem optical imaging and therapy has not been provided. The ability to use one molecular system for drug delivery and imaging is provided in this invention.

SUMMARY OF THE INVENTION

The present invention provides optical agents, including compositions, preparations and formulations, for optical imaging and therapy. In particular, the optical agent is useful for tandem optical imaging and therapy, i.e., where an optical agent contains chemical moieties which are useful for performing optical imaging applications and also moieties which are useful for therapeutic applications. Specific aspects of optical imaging include visualization, diagnostic monitoring and phototherapeutic applications. Specific aspects of therapy include chemotherapy, or drug therapy used in the prevention or treatment of a variety of disease conditions. In an aspect, the invention provides controlled delivery of a therapeutic agent.

Optical agents of the present invention include photonic nanostructures and nanoassemblies including supramolecular structures, such as shell-cross linked nanoparticles or rod-shaped nanostructures that incorporate at least one linking group comprising one or more photoactive moieties that provide functionality for imaging applications, and incorporate at least one therapeutic agent. Optical agents of the present invention comprise supramolecular structures having linking groups imparting useful optical and structural functionality. In an embodiment, for example, the presence of linking groups function to covalently cross link polymer components to provide a cross linked shell stabilized supramolecular structure, and also impart useful optical functionality, for example by functioning as a chromophore, fluorophore, photosensitizer, and/or a photoreactive species.

In an aspect of the invention, the optical agent forms a supramolecular structure in aqueous solution, the supramolecular structure having an interior hydrophobic core and a covalently cross linked hydrophilic shell, wherein the interior hydrophobic core comprises the hydrophobic blocks of the block copolymers, and the covalently cross linked hydrophilic shell comprises the hydrophilic blocks of the block copolymers, and wherein the therapeutic agent is at least partially encapsulated by the supramolecular structure and the therapeutic agent is non-covalently associated with the hydrophobic core. In an aspect, the therapeutic agent is non-covalently associated with the supramolecular structure. In an aspect, the optical agent comprises cross linked block copolymers, wherein each of the block copolymers comprises a hydrophilic block and a hydrophobic block; and linking groups covalently cross linking at least a portion of the hydrophilic blocks of the block copolymers, wherein at least a portion of the linking groups comprise one or more photoactive moieties; and a therapeutic agent; wherein the optical agent forms a supramolecular structure in aqueous solution, the supramolecular structure having an interior hydrophobic core and a covalently cross linked hydrophilic shell, wherein the interior hydrophobic core comprises the hydrophobic blocks of the block copolymers, and the covalently cross linked hydrophilic shell comprises the hydrophilic blocks of the block copolymers, and wherein the therapeutic agent is at least partially encapsulated by the supramolecular structure and the therapeutic agent is non-covalently associated with the hydrophobic core. In an aspect, the therapeutic agent is associated with the supramolecular structure in any structural configuration that allows useful release of the therapeutic agent. In an embodiment, the therapeutic agent is at least partially encapsulated by the supramolecular structure. Optical agents of the present invention include supramolecular structures and assemblies, including shell-cross linked micelles, wherein a therapeutic agent is physically associated with or covalently linked to one or more of the blocks of the copolymers.

In an aspect, there is more than one different therapeutic agent associated with the supramolecular structure. In exemplary embodiments of this aspect of the invention, the different therapeutic agents can be useful for different disease conditions. In exemplary embodiments of this aspect of the invention, the different therapeutic agents can be chemical variations on the same chemical moiety which may each have different release profiles, for example.

Optical agents of the present invention are useful for imaging a therapeutic agent in combination with a variety of in vivo, in vitro and ex vivo biomedical diagnostic, visualization and imaging applications, such as tomographic imaging, monitoring and evaluating organ functioning, anatomical visualization, coronary angiography, fluorescence endoscopy, phototherapeutic treatment methods, image guided surgery, administration and targeted specific delivery of therapeutic agents, endoscopic procedures and therapies, and the detection and imaging of tumors. Useful optical imaging methods include multiphoton imaging, and photoacoustic imaging. In an embodiment, photonic nanostructures and nanoassemblies of the present invention comprising shell-cross linked micelles provide optical agents for absorbing electromagnetic radiation provided to a target biological environment, organ or tissue, and transferring it internally to a phototherapeutic agent capable of providing a desired therapeutic effect. In this aspect, the phototherapeutic agent can be used in combination with a non-phototherapy therapeutic agent.

In one aspect, the present invention provides an optical agent that includes a cross linked supramolecular structure having bifunctional linking groups for covalently cross linking polymer components and for providing useful optical functionality and for providing a chemical environment for associating the therapeutic agent. Further description of the polymer blocks and supramolecular structures is provided elsewhere herein.

In an embodiment, the optical agent forms a supramolecular structure in aqueous solution comprising a spherical, cylindrical, discoidal, toroidal, vesicular or multi-compartment structure.

Optical agents of the present invention include, for example, shell-cross linked micelles, optionally having cross sectional dimensions selected from the range of 5 nanometers to 500 nanometers, and all individual values and ranges therein, capable of functioning as a chromophore, fluorophore or phototherapeutic agent, and optionally capable of excitation in the visible region (e.g. 400 nm to 750 nm) and/or the near infrared region (e.g., 750-1300 nm). Selection of the physical dimensions of micelle-based optical agents of the present invention may be based on a number of factors such as, toxicity, immune response, biocompatibility and/or bioclearance considerations. In embodiments, the cross sectional dimensions are between 5 to 75 nm. In embodiments, the cross sectional dimensions are between 25 to 100 nm. In an embodiment, the optical agent comprises dyes that absorb and emit at a wavelength between 350 and 1200 nm, including azulenes and NIR dyes for imaging. In an embodiment, the optical agent comprises Type I phototherapeutic agents, including azides, azo compounds and sulfenates. In an embodiment, the optical agent comprises Type II phototherapeutic agents including porphyrins.

In an aspect of the invention, a therapeutic agent is a cytotoxic agent. As used herein, a cytotoxic agent kills a cell or decreases cell viability. In an aspect of the invention, the therapeutic agent is a chemotherapy agent. Chemotherapeutic agents comprise alkylating agents, DNA intercalators, microtubule-targeting molecules, folate antagonists, nucleoside antimetabolites, and other antineoplastic agents described in "Chemotherapeutic Agents. In *Cancer Medicine*, Vol. 1, Kufe, D. W. et al. Eds., BC Decker, Hamilton, Ontario, 2003, pp. 727-811," incorporated herein by reference. In an embodiment, the chemotherapy agent is a DNA intercalating anthracycline drug. In an embodiment, the anthracycline drug is daunorubicin, doxorubicin, epirubicin, 2-pyrrolinodoxorubicin, morpholino-doxorubicin or cyanomorpholino-doxorubicin. In an embodiment, the chemotherapy agent is any known chemotherapeutic agent including vinblastine, vincristine, tamoxifen and antiapoptotic agents such as bortezomib and cycloheximide. In an aspect of the invention, the therapeutic agent is a platinum complex, a Taxol, a Type I phototherapeutic compound, or a Type II phototherapeutic compound. Therapeutic agents can be used in the methods and compounds and compositions of the invention without undue experimentation by using the information provided here regarding association of the therapeutic agent with the supramolecular structure and other aspects of the invention. In an embodiment, the therapeutic agent is present in the optical agent at an effective concentration. In an embodiment, the therapeutic agent is present in the optical agent at an effective concentration to provide a cytotoxic effect to a cell or portion thereof. In an embodiment, the therapeutic agent reaches a level or 1 micromolar to 1 millimolar after administration of the nanoparticle to the subject or patient. In an embodiment, the therapeutic agent is present in amount of 0.005 to 0.1 mg/mL. These concentrations are calculated based on the weight percent of the drug with respect to the weight of the polymer. For example, up to 20 wt % of paclitaxel can be loaded into the nanoparticle, up to 5 wt % of Type I phototherapeutic can be loaded into the nanoparticle, and up to 18 wt % of doxorubicin can be loaded into nanoparticle and up to 36 wt % of doxorubicin can be loaded into rod-shaped nanostructure In an aspect, the optical agent of the invention further comprises a targeting moiety. In an embodiment, a targeting moiety is chemically bonded or physically associated to the hydrophilic blocks of at least a portion of the block copolymer. In an embodiment, the targeting moiety is a peptide, a protein, an oligonucleotide, an antibody, a carbohydrate, a hormone, a lipid or a drug. In an embodiment, the targeting moiety comprises a ST receptor binding agent, a bombesin receptor binding agent, a leukemia peptide, and a folate receptor binding agent.

In an aspect, the present invention provides a tandem optical imaging method and therapeutic method. In this method, an effective amount of an optical agent of the present invention is administered to a mammal (e.g., a patient undergoing treatment). In this aspect, at least one photoactive moiety of the optical agent includes at least one chromophore and/or fluorophore, optionally capable of excitation via absorption of electromagnetic radiation having wavelengths in the visible region (e.g. 400 nm to 750 nm) and/or the near infrared region (e.g., 750-1300 nm). The optical agent that has been administered is exposed to electromagnetic radiation. Electromagnetic radiation transmitted, scattered or emitted by the optical agent is then detected. In some embodiments, fluorescence may be excited from the optical agent (e.g., due to the electromagnetic radiation exposure), optionally via multiphoton excitation processes. Use of electromagnetic radiation having wavelengths selected over the range of 400 nanometers to 1300 nanometers may be useful for some in situ optical imaging methods of the present invention, including biomedical applications for imaging organs, tissue and/or tumors, anatomical visualization, optical guided surgery and endoscopic procedures. The therapeutic agent is released from the optical agent before, during or after the optical imaging procedure. Specifically, the word "tandem" does not require the optical imaging and therapy procedures be necessarily simultaneous. In an aspect, the release of a therapeutic agent can occur over time and the extent of release over time can be monitored.

In another aspect, the present invention provides a method of providing photodynamic therapy. In this method, an effective amount of an optical agent of the present invention is administered to a mammal (e.g., a patient undergoing treatment). In this aspect, at least one photoactive moiety of the optical agent includes one or more phototherapeutic agents, optionally capable of excitation via absorption of electromagnetic radiation having wavelengths in the visible region (e.g. 400 nm to 750 nm) and/or the near infrared region (e.g., 750-1300 nm). The optical agent that has been administered is exposed to electromagnetic radiation. In some embodiments, the optical agent may be targeted to a selected organ, tissue or tumor site in the mammal, for example by incorporation of an appropriate targeting ligand in the optical agent. Use of electromagnetic radiation having wavelengths selected over the range of 400 nanometers to 1300 nanometers may be useful for some phototherapeutic treatment methods of the present invention. Exposure of the optical agent to electromagnetic radiation activates the phototherapeutic agent(s) causing, for example, release of the phototherapeutic agent and/or cleavage of one or more photolabile bonds of the phototherapeutic agent, thereby generating one or more reactive species (e.g., free radicals, ions etc.). In an embodiment, the associated phototherapeutic agent provides a secondary treatment mode.

In another aspect, the invention provides an optical agent for use in a tandem optical imaging and therapeutic procedure. In an embodiment, a procedure of the present invention comprises: (i) administering to a mammal an effective amount of the optical agent as described herein, wherein the one or more photoactive moieties comprise one or more chromophores and/or fluorophores, wherein the therapeutic agent is released from the supramolecular structure; (ii) exposing the optical agent administered to the mammal to electromagnetic radiation; and (iii) detecting electromagnetic radiation transmitted, scattered or emitted by the optical agent.

In another aspect, the invention provides a shell-cross linked micelle comprising: (i) cross linked block copolymers, wherein each of the block copolymers comprises a poly (acrylic acid) polymer block directly or indirectly bonded to a hydrophobic block; (ii) pyrazine-containing linking groups covalently cross linking at least a portion of the poly(acrylic acid) polymer blocks of the block copolymers; wherein the pyrazine-containing linking groups are bound to monomers of the poly(acrylic acid) polymer block by amide bonds, wherein the copolymers form a supramolecular structure; and (iii) a therapeutic agent at least partially encapsulated by the supramolecular structure. In an embodiment of this aspect, the mole ratio of the pyrazine-containing linking groups to monomers of the poly(acrylic acid) polymer block is selected over a range of 1:100 to 99:100.

DETAILED DESCRIPTION OF THE INVENTION

Figure 1:
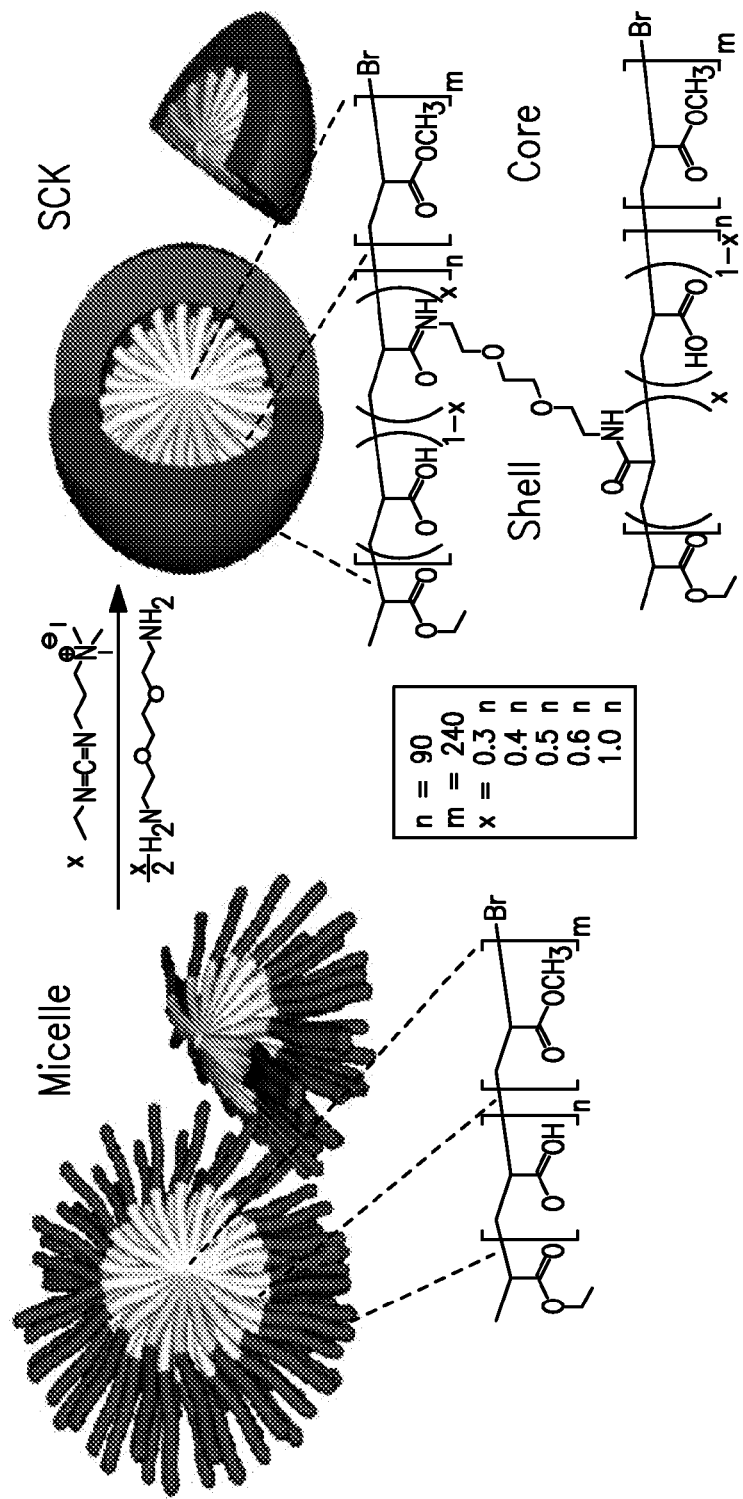
FIG. 1 illustrates an example of SCK formation. Amphiphilic block copolymers self-assemble into micelles having a hydrophobic core. The block copolymers are then functionalized to form cross linking between the individual polymers. The cross linking of the copolymers forms a shell surrounding the hydrophobic core.
Figure 2:
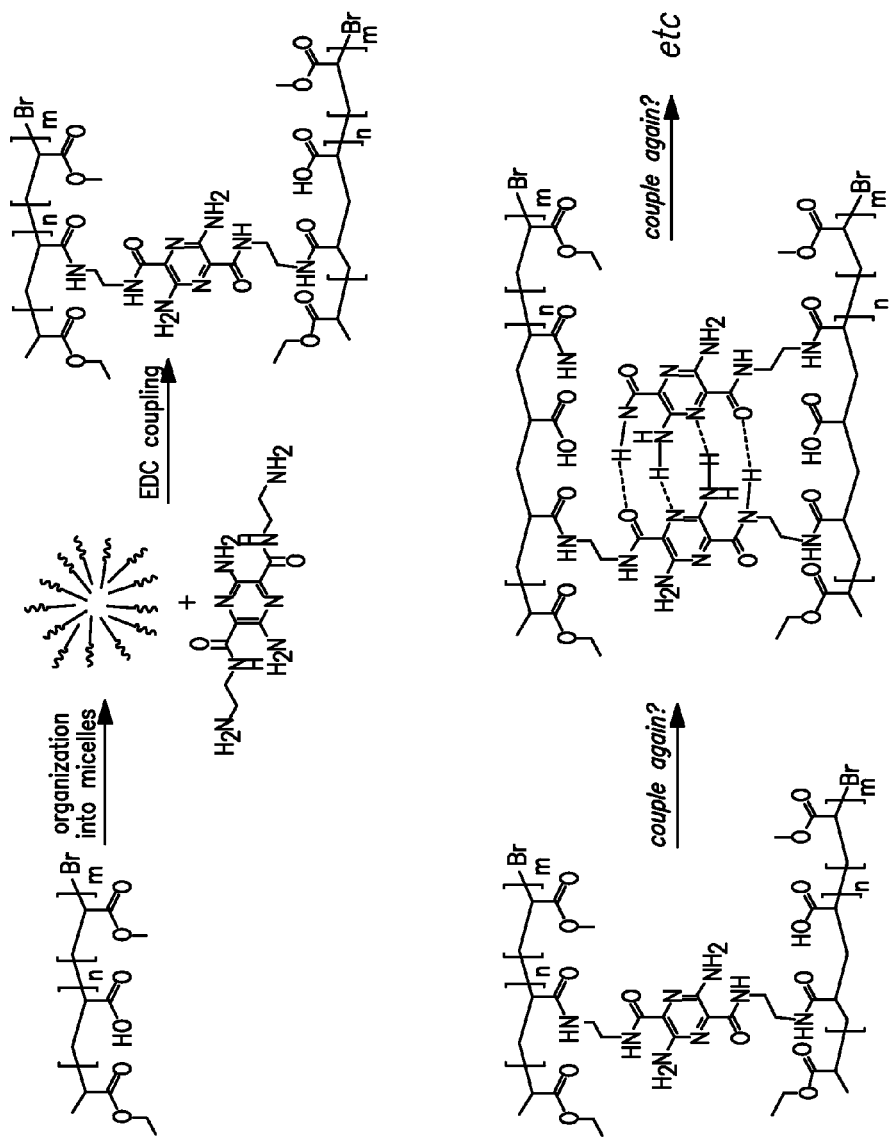
FIG. 2 provides a schematic diagram illustrating a synthetic pathway for the formation of photonic shell containing SCKs via cross linking chemistry with a photonic linking group of the present invention.
Figure 3:
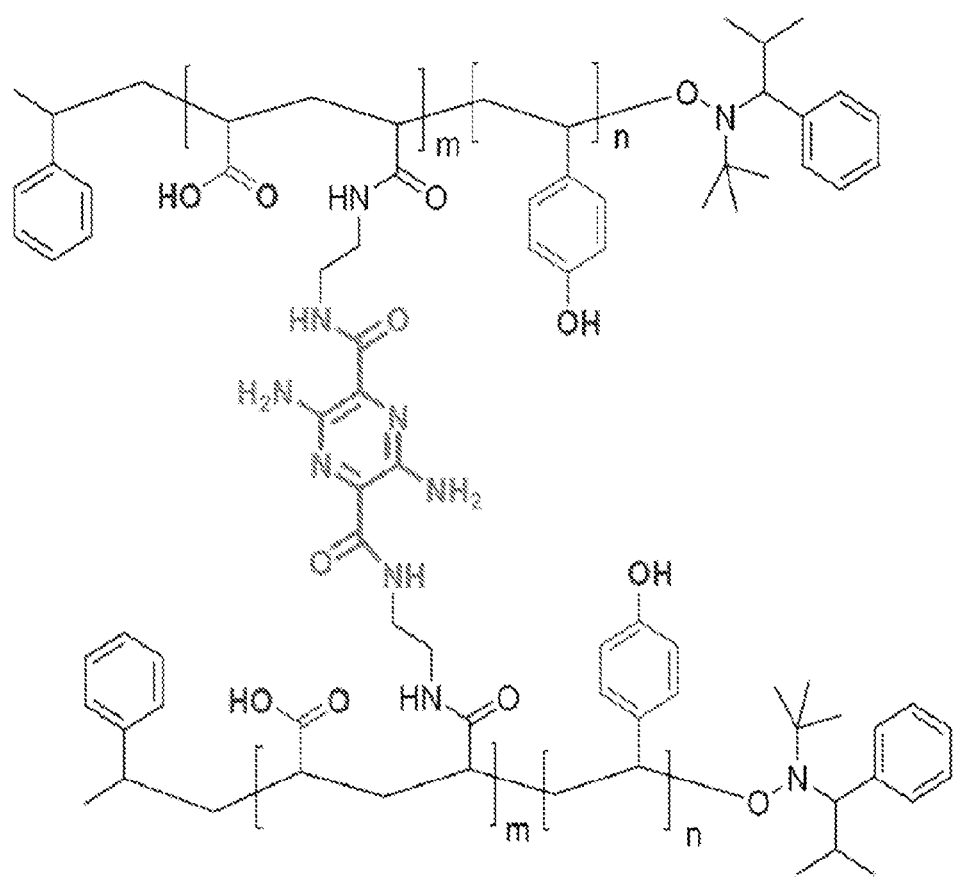
FIG. 3 illustrates an exemplary photonic shell cross linked nanoparticle structure.

In general the terms and phrases used herein have their art-recognized meaning, which can be found by reference to standard texts, journal references and contexts known to those skilled in the art. The following definitions are provided to clarify their specific use in the context of the invention.

"Optical agent" generally refers to compositions, preparations and/or formulations for coupling electromagnetic radiation into and/or out of an environment and/or sample. For some applications, for example, the present optical agents are administered to a biological environment or sample, such as a patient, mammal, an organ, tissue, tumor, tumor site, excised tissue or cell material, cell extract, and/or biological fluid, colloid and/or suspension, for coupling electromagnetic radiation into and/or out of a biological sample. In some embodiments, optical agents of the present invention absorb, transmit and/or scatter electromagnetic radiation provided to a biologic sample and/or biological environment. In some embodiments, optical agents of the present invention are excited by electromagnetic radiation provided to a biologic sample and/or biological environment, and emit electromagnetic radiation via fluorescence, phosphorescence, chemiluminescence and/or photoacoustic processes. In some embodiments, optical agents of the present invention absorb electromagnetic radiation provided to a biologic sample and/or biological environment, and become activated, for example via photofragmentation or other photoinitiated chemical reaction, including photocleavage of one or more photolabile bonds or photofragmentation to generate reactive species such as nitrenes, carbine, free radicals and/or ions. In some embodiments, optical agents of the present invention absorb electromagnetic radiation provided to a biologic sample and/or biological environment and radiatively or non-radiatively transfer at least a portion of the absorbed energy to a moiety, molecule, complex or assembly in proximity.

Optical agents of the present invention include, but are not limited to, contrast agents, imaging agents, dyes, photosensitizer agents, photoactivators, and photoreactive agents; and conjugates, complexes, bioconjugates, and derivatives thereof. Optical agents of the present invention include photonic nanostructures and nanoassemblies including supramolecular structures, such as spherical, cylindrical, discoidal, toroidal, vesicular or multi-compartment micelles, that incorporate at least one linking groups comprising a photoactive moiety, such as a fluorophore, a chromophore, a photosensitizer, and a photoreactive moiety and a therapeutic agent at least partially encapsulated by the supramolecular structure.

"Supramolecular structure" refers to structures comprising an assembly of molecules that are covalently linked, physically associated or both covalently linked and physically associated. Supramolecular structures include assemblies of molecules, such as amphiphilic polymers, including block copolymers having a hydrophilic block and hydrophobic group. In some supramolecular structures of the present invention, hydrophilic portions of the block copolymers are oriented outward toward a continuous aqueous phase and form a hydrophilic shell or corona phase, and hydrophobic portions of the block copolymers are oriented inward and form a hydrophobic inner core. Supramolecular structures of the present invention include, but are not limited to, spherical, cylindrical, discoidal, toroidal, vesicular or multi-compartment micelles. Supramolecular structures of the present invention include self assembled structures. Supramolecular structures include cross linked structures, such as shell-cross linked micelle structures and shell-crosslinked nanoparticles (SCK) or rod-shaped nanostructures (SC-rods or SCR).

"Polymer" refers to a molecule comprising a plurality of repeating chemical groups, typically referred to as monomers. Polymers may include any number of different monomer types provided in a well defined sequence or random distribution. A "copolymer", also commonly referred to as a heteropolymer, is a polymer formed when two or more different types of monomers are linked in the same polymer. "Block copolymers" are a type of copolymer comprising blocks or spatially segregated domains, wherein different domains comprise different polymerized monomers having different compositions, chemical properties and/or physical properties. In a block copolymer, adjacent blocks are constitutionally different, i.e. adjacent blocks comprise constitutional units derived from different species of monomer or from the same species of monomer but with a different composition or sequence distribution of constitutional units. Different blocks (or domains) of a block copolymer may reside on different ends or the interior of a polymer (e.g. [A][B]), or may be provided in a selected sequence ([A][B][A][B], for example). "Diblock copolymer" refers to block copolymer having two different polymer blocks. "Triblock copolymer" refers to block copolymer having three different polymer blocks. "Polyblock copolymer" refers to block copolymer having at least two different polymer blocks, such as two, three, four, five etc. different polymer blocks. Optical agents of the present invention include supramolecular structures comprising diblock copolymers, triblock copolymers and polyblock copolymers, along with graft copolymers. Optionally, block copolymers of the present invention comprise a PEG block (i.e., $(CH_2CH_2O)_b$—). Optionally, block copolymers of the present invention comprise a PEG block bound to one or more blocks of the copolymer backbone. The methods of incorporating and using PEG in the current optical agents is described further elsewhere herein.

"Photoactive moiety" generally refers to a component of a molecule having optical functionality. Photoactive moieties include, for example, functional groups and substituents that function as a fluorophore or a chromophore in the present compositions and methods. Photoactive moieties are capable of undergoing a number of processes upon absorption of electromagnetic radiation including fluorescence, activation, cleavage of one or more photolabile bonds and energy transfer processes. Photoactive or photoreactive in this context refers to compositions and components thereof that are activated by absorption of electromagnetic radiation and, subsequently undergo chemical reaction or energy transfer processes. The present invention includes optical agents comprising supramolecular structures, such as shell cross-linked micelles, having linking groups comprising photoactive moieties that are excited upon absorption of electromagnetic radiation having wavelengths in the visible region (e.g. 400 nm to 750 nm) and/or the near infrared region (e.g., 750-1300 nm). The amount of photoactive moiety in the optical agents may be any amount that allows the desired purpose. For example, if the optical agent is used for fluorescence imaging, there must be a sufficient amount of photoactive moiety in the optical agent to be monitored. In embodiments, there is between 1 and 40% of a photoactive moiety in an optical agent, with respect to the number of acrylic acid repeat units.

As used herein "hydrophilic" refers to molecules and/or components (e.g., functional groups, monomers of block polymers etc.) of molecules having at least one hydrophilic group, and "hydrophobic" refers to molecules and/or components (e.g., functional groups of polymers, and monomers of block copolymers etc.) of molecules having at least one hydrophobic group. Hydrophilic molecules or components thereof tend to have ionic and/or polar groups, and hydrophobic molecules or components thereof tend to have nonionic and/or nonpolar groups. Hydrophilic molecules or components thereof tend to participate in stabilizing interactions with an aqueous solution, including hydrogen bonding and dipole-dipole interactions. Hydrophobic molecules or components tend not to participate in stabilizing interactions with an aqueous solution and, thus often cluster together in an aqueous solution to achieve a more stable thermodynamic state. An amphiphilic molecule or structure comprises both hydrophobic and hydrophilic units. It is recognized that in the context of an amphiphilic block copolymer of the present invention, a block may be both relatively more hydrophobic than another block and a block may be relatively more hydrophilic than another block.

When used herein, the term "diagnosis", "diagnostic" and other root word derivatives are as understood in the art and are further intended to include a general monitoring, characterizing and/or identifying a state of health or disease. The term is meant to encompass the concept of prognosis. For example, the diagnosis of cancer can include an initial determination and/or one or more subsequent assessments regardless of the outcome of a previous finding. The term does not necessarily imply a defined level of certainty regarding the prediction of a particular status or outcome.

As defined herein, "contacting" means that a compound used in the present invention is provided such that is capable of making physical contact with another element, such as a microorganism, a microbial culture or a substrate. In another embodiment, the term "contacting" means that the compound used in the present invention is introduced into a subject receiving treatment, and the compound is allowed to come in contact in vivo.

As used herein, "therapeutic agent" means a compound or group which is useful in ameliorating, suppressing, eradicating, preventing, reducing the risk of, or delaying the onset of a disease condition. In an embodiment, the disease condition is cancer and the therapeutic agent is a cancer drug. In an embodiment, a composition of the invention is isolated or purified. In an embodiment, an isolated or purified compound may be at least partially isolated or purified as would be understood in the art. In an embodiment, the composition of the invention has a chemical purity of 95%, optionally for some applications 99%, optionally for some applications 99.9%, optionally for some applications 99.99% pure, and optionally for some applications 99.999% pure.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups (or cycloalkyl groups) include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxyl group is an alkyl group linked to oxygen and can be represented by the formula R—O.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
- —COOR where R is a hydrogen or an alkyl group or an aryl group and more specifically where R is methyl, ethyl, propyl, butyl, or phenyl groups all of which are optionally substituted;
- —COR where R is a hydrogen, or an alkyl group or an aryl groups and more specifically where R is methyl, ethyl, propyl, butyl, or phenyl groups all of which groups are optionally substituted;
- —CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
- —N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.
- —SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
- —OCOOR where R is an alkyl group or an aryl groups;
- —SO$_2$N(R)$_2$ where R is a hydrogen, an alkyl group, or an aryl group and R and R can form a ring;
- —OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As used herein, the term "alkylene" refers to a divalent radical derived from an alkyl group as defined herein. Alkylene groups in some embodiments function as bridging and/or spacer groups in the present compositions.

As used herein, the term "cycloalkylene" refers to a divalent radical derived from a cycloalkyl group as defined herein. Cycloalkylene groups in some embodiments function as bridging and/or spacer groups in the present compositions.

As used herein, the term "alkenylene" refers to a divalent radical derived from an alkenyl group as defined herein. Alkenylene groups in some embodiments function as bridging and/or spacer groups in the present compositions.

As used herein, the term "cycloalkenylene" refers to a divalent radical derived from a cycloalkenyl group as defined herein. Cycloalkenylene groups in some embodiments function as bridging and/or spacer groups in the present compositions.

As used herein, the term "alkynylene" refers to a divalent radical derived from an alkynyl group as defined herein. Alkynylene groups in some embodiments function as bridging and/or spacer groups in the present compositions.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Pharmaceutically acceptable salts comprise pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$_4^+$) and substituted ammonium (N(R')$_4^+$), where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

The compounds of this invention may contain one or more chiral centers. Accordingly, this invention is intended to include racemic mixtures, diasteromers, enantiomers and mixtures enriched in one or more steroisomer. The scope of the invention as described and claimed encompasses the racemic forms of the compounds as well as the individual enantiomers and non-racemic mixtures thereof.

Many of the compositions described herein are at least partially present as an ion when provided in solution and as will be understood by those having skill in the art the present compositions include these partially or fully ionic forms. A specific example relates to acidic and basic groups, for example on the polymer back bone of block copolymers and in linking groups, that will be in an equilibrium in solution with respect to ionic and non-ionic forms. The compositions and formula provided herein include all fully and partially ionic forms that would be present in solution conditions of pH ranging from 1-14, and optionally pH ranging from 3-12 and optionally pH ranging from 6-8. The compositions and formula provided herein include all fully and partially ionic forms that would be present under physiological conditions.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering optical agents useful in the present invention to a patient or subject. A "patient" or "subject", used equivalently herein, refers to an animal. In particular, an animal refers to a mammal, preferably a human. The subject either: (1) has a condition remediable or treatable by administration of an optical agent of the invention; or (2) is susceptible to a condition that is preventable or capable of lessening the duration and/or severity of by administering an optical agent of this invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

This disclosure relates generally to the concept of integrating therapeutic agents and photoactive molecules (e.g., fluorophores or chromophores) into polymer micelles through physical association and covalent cross linking chemistry. The resulting nanosystems are useful for tandem therapy and in vivo imaging, visualization, monitoring and phototherapy applications.

An optical agent of this aspect comprises cross linked block copolymers, each of which comprises a hydrophilic block and a hydrophobic block. Further, the optical agent of this aspect comprises linking groups that covalently cross link at least a portion of the hydrophilic blocks of the block copolymers. With regard to some optical agents, at least a portion of the linking groups connecting hydrophilic blocks of the block copolymers include one or more photoactive moieties, such as fluorophores or photosensitizers capable of excitation in the visible region (e.g. 400 nm to 750 nm) and/or the near infrared region (e.g., 750-1300 nm). The compositions of block copolymer and linking group components are selected such that the optical agent forms a supramolecular structure in aqueous solution. This resulting supramolecular structure has an interior hydrophobic core that includes the hydrophobic blocks of the block copolymers. Also, the resulting supramolecular structure has a covalently cross linked hydrophilic shell that includes the hydrophilic blocks of the block copolymers.

Selection of the composition of linking groups and extent of cross linking, at least in part, determines the optical, physical, physiological and chemical properties of supramolecular structures and assemblies of optical agents of the present invention, such as their excitation wavelengths, emission wavelengths, Stokes shifts, quantum yields, cross sectional dimensions, extent of cross linking, stability, biocompatibility, physiological clearance rate upon administration to a patient, etc. Useful photoactive moieties of the linking groups for optical agents of the present invention include one or more fluorophores, chromophores, and conjugates, complexes, fragments and derivatives thereof. In an embodiment, for example, the stoichiometric ratio of the linking groups to monomers of the hydrophilic blocks is selected over the range of 0.1:100 to 99:100, optionally 1:100 to 50:100, still optionally 50:100 to 99:100, also optionally 1:100 to 25:100, preferably 25:100 to 75:100. These concepts are discussed in WO2009/061473 which is hereby incorporated by reference in its entirety.

In an embodiment of the optical imaging aspect of the invention, in particular diagnostic, imaging and physiological sensing applications, at least a portion of the linking groups of the present optical agents comprise one or more chromophores and/or fluorophores. Useful linking groups of this aspect include visible dyes and/or near infrared dyes, including fluorescent dyes. In an embodiment, for example, the linking groups are chromophore and/or fluorophore functional groups capable of excitation upon absorption of electromagnetic radiation having wavelengths selected over the range of 400 nanometers to 1300 nanometers, and optionally capable of emission of electromagnetic radiation having wavelengths selected over the range of 400 nanometers to 1300 nanometers. Incorporation of linking groups that are excited upon absorption of electromagnetic radiation having wavelengths over the range of about 700 nanometers to about 1200 nanometers, optionally for some applications 400 nm to 900 nm, and optionally for some applications 700 nm to 900 nm, is particularly useful for certain diagnostic and therapeutic applications as electromagnetic radiation of these wavelengths is effectively transmitted by some biological samples and environments (e.g., biological tissue). In an embodiment, an optical agent of the invention includes one or more fluorophores having a Stokes shift selected over the range of, for example, 10 nanometers to 200 nanometers, optionally for some applications 20 nm to 200 nm, and optionally for some applications 50 nm to 200 nm. Useful photoactive moieties of the linking groups for optical agents of the present invention include a pyrazine, and conjugates, complexes, fragments and derivatives thereof. In an embodiment, an optical agent of the present invention comprises a pyrazine-based linking group that cross links the hydrophilic blocks of the block copolymers, optionally a pyrazine-based amino linking group, such as a pyrazine-based diamino linking group or a pyrazine-based tetra amino linking group.

A range of linking chemistry is useful in the shell-cross linked supramolecular structures of optical agents of the present invention. Cross linking can be achieved, for example, via chemical reaction between the hydrophilic blocks of copolymers and cross linking reagents(s) containing one or more amine, imine, sulfhydryl, azide, carbonyl, imidoester, succinimidyl ester, carboxylic acid, hydroxyl, thiol, thiocyanate, acrylate, or halo group. Cross linking can be achieved, for example, via chemical reaction between cross linking reagents(s) and the hydrophilic block of the copolymer containing one or more monomers having one or more ester sites for conjugation to the linking group via amidation. In an embodiment the hydrophilic block of the copolymer includes N-acryloxysuccinimide monomers for conjugation to the linking groups. In some embodiments, for example, the hydrophilic block of the copolymers are cross linked via amide or disulfide linkages between at least a portion of the monomers of the hydrophilic blocks and the linking groups. Linking groups of the present invention optionally include spacer moieties, such as a $C_1$-$C_{30}$ poly (ethylene glycol) (PEG) spacer, or substituted or unsubstituted $C_1$-$C_{30}$ alkyl chain. Linking groups of the present invention optionally include one or more amino acid groups or derivatives thereof. In an embodiment, for example, an optical agent of the present invention incorporates linking groups having one or more basic amino acid groups or derivatives thereof including, but not limited to, arginine, lysine, histidine, ornithine, and homoarginine. Use of linking groups containing one or more basic amino acids is beneficial in the present invention for achieving high extents of cross linking between monomers of the hydrophilic groups of the block copolymers.

In an embodiment of phototherapeutic applications, the photoactive moiety(ies) of the linking groups for the optical agents comprise(s) one or more photoreactive moieties such as phototherapeutic agents or precursors of phototherapeutic agents, optionally capable of excitation via absorption of electromagnetic radiation having wavelengths in the visible region (e.g. 400 nm to 750 nm) and/or the near infrared region (e.g., 750-1300 nm). In some embodiments, for example, the linking groups are capable of absorbing electromagnetic radiation and initiating a desired therapeutic effect such as the degradation of a tumor or other lesion. In an embodiment, for example, an optical agent of the present invention comprises linking groups containing one or more photosensitizer that absorbs visible or near infrared radiation and undergoes cleavage of photolabile bonds and/or energy transfer processes that generate reactive species (e.g., radicals, ions, nitrene, carbine etc.) capable of achieving a desired therapeutic effect. In an embodiment, an optical agent comprises a phototherapeutic agent comprising linking groups that generates reactive species (e.g., radicals, ions, nitrene, carbine etc.) upon absorption of electromagnetic radiation having wavelengths selected over the range of 700 nanometers to 1200 nanometers, optionally for some applications 400 nm to 900 nm, and optionally for some applications 700 nm to 900 nm.

Useful photoreactive moieties for linking groups of optical agents of this aspect of the present invention include, but are not limited to, Type-1 or Type-2 phototherapeutic agents such as: a cyanine, an indocyanine, a phthalocyanine, a rhodamine, a phenoxazine, a phenothiazine, a phenoselenazine, a fluorescein, a porphyrin, a benzoporphyrin, a pyrazine, a squaraine, a corrin, a croconium, an azo dye, a methine dye, an indolenium dye, a halogen, an anthracyline, an azide, a sulfenate, a diazo compound, a chlorine, a naphthalocyanine, a methylene blue, a chalcogenopyrylium analogue, a disulfide, a sulfenamide, a hydrazine, an o-alkyl-hydroxylamine, and conjugates, complexes, fragments and derivatives thereof.

Selection of the composition of block copolymers in part determines the optical, physical, physiological and chemical properties of supramolecular structures and assemblies of optical agents of the present invention, such as the excitation wavelengths, emission wavelengths, Stokes shifts, quantum yields, cross sectional dimensions, extent of cross linking, stability, biocompatibility, physiological clearance rate upon administration to a patient etc. In an embodiment, the present invention provides an optical agent that is a supramolecular structure or assembly, such as a shell-cross linked micelle composition, wherein at least a portion of the polymer components comprise diblock copolymers each having a hydrophilic block directly or indirectly linked to a hydrophobic block. In the context of this description, directly linked refers to block copolymers wherein the hydrophilic and hydrophobic block are linked to each other directly via a covalent bond, and indirectly linked refers to block copolymers wherein the hydrophilic and hydrophobic block are linked to each other indirectly via a spacer or linking group. Hydrophilic blocks and hydrophobic blocks of block copolymers of the present invention can have a wide range of lengths, for example, lengths selected over the range of 10 to 250 monomers. Hydrophilic blocks of supramolecular structures and assemblies of the present optical agents are capable of effective cross linking between the block copolymers, for example using EDC (1-Ethyl-3-[3-dimethylaminopropyl]carbodiimide hydrochloride) coupling reactions or photoinitiated cross linking reactions. In an embodiment, degradable polymers are used in the compositions and methods of the invention. In an embodiment, degradable polymers degrade under conditions present in a human.

In an embodiment, hydrophilic blocks of optical agents of the present invention (represented by [hydrophobic block] in some examples) include, but are not limited to, a poly(acrylic acid) polymer block; a poly(ethylene glycol) polymer block; a poly(acetoxystyrene) polymer block; or a copolymer thereof. In an embodiment, useful hydrophobic blocks of optical agents of the present invention include, but are not limited to, a poly(p-hydroxystyrene) polymer block; a polystyrene polymer block; a polyacrylate polymer block, a poly (propylene glycol) polymer block; a poly(ester) polymer block; a polylactic acid block; or a copolymer thereof. In an embodiment, the hydrophilic block has a number of monomers selected from the range of 10 to 250. In an embodiment, the hydrophilic block has a number of monomers selected from the range of 40 to 100. In an embodiment, the hydrophilic block has a number of polymers selected from the range of 200 to 600.

The hydrophobic block in the formulas provided herein (represented by [hydrophobic block]) can have a wide range of compositions depending on the desired application and use of the present optical agents. In an embodiment, the composition of [hydrophobic block] is selected from the group consisting of a poly(p-hydroxystyrene) polymer block; a polystyrene polymer block; a polyacrylate polymer block, a poly (propylene glycol) polymer block; or a copolymer thereof. In an embodiment, the [hydrophobic block] comprises monomers including one or more aryl groups, such as phenyl, phenol and/or derivative thereof. In an embodiment, the hydrophobic block is a poly(p-hydroxystyrene) polymer block; a polystyrene polymer block; a polyacrylate polymer block; a poly(propylene glycol) polymer block; a poly(ester)

polymer block; a polylactic acid polymer block; a poly(tert-butylacrylate) polymer block; a poly(N-acryloxysuccinimide) polymer block; or a copolymer thereof.

In an embodiment, the hydrophobic block has a number of monomers selected from the range of 10 to 250. In an embodiment, the hydrophobic block has a number of monomers selected from the range of 40 to 100. In an embodiment, the hydrophobic block has a number of polymers selected from the range of 200 to 600. In a specific embodiment, the hydrophobic block is poly(p-hydroxystyrene) and has a number of polymers selected from the range of 300 to 600. In a specific embodiment, the hydrophobic block is poly(p-hydroxystyrene) and has a number of polymers selected from the range of 30 to 200. In a specific embodiment, the hydrophobic block is polystyrene and has a number of polymers selected from the range of 40 to 100.

In an embodiment, the hydrophobic block is selected from but not limited to poly(methyl acrylate), poly(ε-caprolactone), poly(lactic acid), poly(glycolic acid), polylactide, and polyglycolide. In an embodiment, the hydrophilic block is selected from but not limited to poly(acrylic acid), poly(aminoethyl acrylamide), poly(oligoethylene oxide acrylate), and poly(N-acryloxysuccinimide).

In a specific embodiment, the hydrophilic block is a poly(acrylic acid) polymer block, a hydrophobic block is a poly(p-hydroxystyrene) block and the linking groups are bound to monomers of the poly(acrylic acid) polymer block by amide bonds. The preparation of the hydrophilic and hydrophobic blocks and copolymers is generally known, as is the suitable lengths of the various blocks of the polymers. These aspects of the invention are intended to be fully included as if they were specifically listed.

In an embodiment, the hydrophilic block comprises poly(acrylic acid) (PAA) and there are from 10 to 500 repeating units. In an embodiment, the hydrophobic block comprises poly(acetoxystyrene) having from 10 to 300 repeating units. In an embodiment, the hydrophobic block comprises poly(p-hydroxystyrene) having from 10 to 300 repeating units. In an embodiment, the hydrophilic block comprises poly(ethylene oxide) (PEO) having from 10 to 300 repeating units. In an embodiment, the hydrophilic block comprises PNAS in aqueous solution having from 10 to 300 repeating units. In an embodiment, the hydrophobic block comprises polystyrene (PS) having from 10 to 600 repeating units.

Compositions of the invention include formulations and preparations comprising one or more of the present optical agents and therapeutic agents provided in an aqueous solution, such as a pharmaceutically acceptable formulation or preparation. Optionally, compositions of the present invention further comprise one or more pharmaceutically acceptable surfactants, buffers, electrolytes, salts, carriers and/or excipients. In an embodiment, the optical agent of the present invention comprises one or more therapeutic agents at least partially encapsulated by the supramolecular structure, such as a hydrophobic drug or combination of hydrophobic drugs, hydrophobic biologic agent, or hydrophobic phototherapeutic agent. The present invention includes, for example, optical agents wherein a therapeutic agent is non-covalently associated with the hydrophobic core. Therapeutic agents of this aspect of the present invention optionally include phototherapeutic agents, such as Type-1 or Type-2 phototherapeutic agents, or chemotherapy agents.

In another aspect, the present invention provides a method of monitoring a physiological state or condition. In this method, an effective amount of an optical agent of the present invention is administered to a mammal (e.g., a patient undergoing treatment). The optical agent that has been administered is exposed to electromagnetic radiation. Electromagnetic radiation transmitted, scattered or emitted by the optical agent is detected. In some embodiments, a change in the wavelength or intensity of electromagnetic radiation emitted by the optical agent that has been administered to the mammal may be detected, measured and/or monitored as a function of time.

In another aspect, the present invention provides a method for making an optical agent. In this method, a plurality of block copolymers are dissolved in aqueous solution, wherein each of the block copolymers comprises a hydrophilic block and a hydrophobic block, and wherein the block copolymers self assemble in the aqueous solution to form a supramolecular structure, such as a micelle structure. The block copolymers of the supramolecular structure are then contacted with a cross linking reagent comprising one or more photoactive moieties, optionally contacted with a pyrazine-based amino cross linker such as a pyrazine-based diamino or tetramino cross linker. Optionally, at least a portion of the monomers of the hydrophilic group comprise N-acryloxysuccinimide (NAS) monomers. Further, at least a portion of the hydrophilic blocks of the block copolymers of the supramolecular structure are cross linked via linking groups generated from the cross linking reagent, thereby making the optical agent. In some embodiments, the block copolymers self assemble in the aqueous solution to form a micelle structure, which is subsequently cross linked to form a shell-cross linked micelle. Optionally, the cross linking may be carried out via EDC coupling reactions or via photoinitiated cross linking reactions. Optionally, the crosslinking may achieve an extent of crosslinking of the hydrophilic blocks of the copolymers selected over the range of 1 to 99%, optionally 1 to 75% and optionally 20 to 75%. In an aspect of the invention, the crosslinking density (the amount of covalently incorporated crosslinkers in the nanostructure network) is between 1-10%. In an aspect of the invention, the crosslinking density is between 20-30%. In an aspect of the invention, the crosslinking density is between 5-35%.

In some embodiments, the dissolving may be carried out at a pH greater than 7. In such embodiments, the pH of the block copolymers dissolved in the aqueous solution may be subsequently slowly decreased to a pH of about 7. In one aspect, a therapeutic agent is associated with the complex by physical association of the copolymers with a solution of the therapeutic agent.

A body of research now exists regarding the supramolecular assembly of amphiphilic block copolymers into micelles which can be covalently shell-cross linked (SCK) to form core-shell type nanoparticles. Aspects of the present invention include the chemical nature of the block copolymers used to form the precursor micelles and the corresponding contributions to the overall morphology and environmental responsiveness of the resulting SCK. Further synthetic elaboration of these systems can be accomplished in a pre- or post-SCK fashion with incorporation of tissue targeting and/or imaging appendages on the exterior of the nanostructure. In addition, chemistry has been developed to attach functionality within the excavated core of SCK nanoparticles.

The methods and compositions of the present invention uses bi-functional optical probe molecules as photonic linkage systems for the micelle cross linking step in SCK formation in an aspect. The resultant SCK nanostructures have a covalently stabilized shell that contains a specified number of copies of the optical probe. As will be recognized, descriptions of SCK also apply to SCR.

The present photonic nanosystems and compositions thereof enable a number of potential biomedical uses.

In an embodiment, photonic nanosystems and compositions thereof enable chemical and/or physiological sensors and sensing methods. In an embodiment, photonic nanosystems and compositions thereof provide carriers and antennae for Type I Phototherapeutic Agents. In an embodiment of this aspect, the photonic shell of the present photonic nanosystems and compositions is used as an "Antenna/Transducer" for absorbing the appropriate laser irradiation and transferring it internally (via FRET) to type I phototherapeutic warheads that are either physically associated with the shell and/or core of the structures or covalently attached either through stable or photolabile bonds. The type I phototherapeutic warheads may be conjugatable derivatives of agents that decompose to cytotoxic reactive intermediates upon laser irradiation. The nanoparticle strategy allows the delivery of large doses in vivo.

Compounds of the present invention further include conjugates, for example, bioconjugates comprising a component of the optical agent linked to one or more targeting ligands such as a peptide, protein or other ligand capable of providing molecular recognition and/or targeting functionality. Specifically, the optical agents described here can be targeted with the appropriate exteriorly displayed ligand to the desired location (e.g. $A_yB_x$ $A_5B_1$, Bombesin, EGF, VEGF, etc). This aspect is described further herein.

In an embodiment, optical agents and compositions thereof provide photoacoustic imaging and therapy agents. In an embodiment of this aspect, the photonic shell SCKs or SCRs provide organic optical probes for photoacoustic imaging and therapy. The photonic shells containing many copies of longer wavelength probes (cryptate analogues, for example) may be tuned to provide the enhanced cross-sections for absorption based photoacoustic methods.

The present invention provides optical agents comprising optically functional cross linked supramolecular structures and assemblies useful for a range of imaging, diagnostic, and therapeutic applications. Supramolecular structures and assemblies of the present invention include optically functional shell-cross linked micelles wherein optical functionality is achieved via incorporation of one or more linking groups comprising photoactive moieties. The present invention further includes imaging, sensing and therapeutic methods using one or more optical agents of the present invention including optically functional shell cross-linked micelles. The present invention includes in situ monitoring methods, for example, wherein physical and/or structural changes in an optically functional shell-cross linked micelle generated in response to changes in chemical environment or physiological conditions causes a measurable change in the wavelengths or intensities of emission from the micelle.

In an aspect, the present invention provides an optical agent comprising an optically functional shell-cross linked micelle, comprising: (i) a plurality of cross linked block copolymers, wherein each of the block copolymers comprises a hydrophilic block and a hydrophobic block; and (ii) a plurality of linking groups covalently cross linking at least a portion of the hydrophilic blocks of the block copolymers, wherein at least a portion of the linking groups comprise one or more photoactive moieties, such as such as chromophores, fluorophores and/or phototherapeutic agents; and a therapeutic agent; wherein the optical agent forms a supramolecular structure in aqueous solution, the supramolecular structure having an interior hydrophobic core and a covalently cross linked hydrophilic shell, wherein the interior hydrophobic core comprises the hydrophobic blocks of the block copolymers, and the covalently cross linked hydrophilic shell comprises the hydrophilic blocks of the block copolymers, and wherein the therapeutic agent is at least partially encapsulated by the supramolecular structure and the therapeutic agent is non-covalently associated with the hydrophobic core.

Optionally, the extent of cross linking in the cross linked micelle is selected over the range of 1% to 75% of the monomers of the hydrophilic blocks of the block copolymers, and optionally 10 to 75% of the monomers of the hydrophilic blocks of the block copolymers.

An optically functional shell-cross linked micelle composition useful for biomedical applications, for example, comprise block copolymers having poly(acrylic acid) polymer hydrophilic block, optionally having between 20-250 monomer units. In an embodiment, for example, linking groups comprising one or more photoactive moieties are bound to at least a portion of the monomers of the poly(acrylic acid) polymer block by amide bonds.

In an embodiment, at least a portion of the monomers of the hydrophilic blocks are bound to pyrazine-based linking groups such as a pyrazine-based amino linking group. In an embodiment, for example, at least a portion of the hydrophilic blocks of the block copolymers comprise monomers bound to linking groups having the formula:

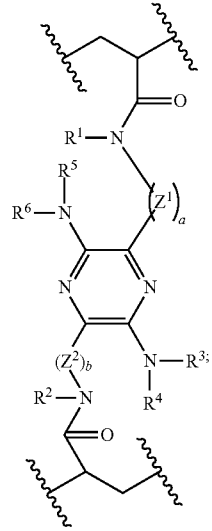

(FX2)

wherein each of $R^1$-$R^6$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group or a natural or non-natural amino acid or fragment (e.g., side chain) thereof;

each of $Z^1$ and $Z^2$ is independently

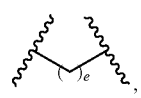

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein each e is independently is selected from the range of 0 to 10; and each of a and b is independently 0 or 1. The present invention includes compositions comprising enantiomers, diastereomers, and/or ionic forms (e.g., protonated and deprotonated forms) of formula (FX2).

In an optical agent of the invention, at least a portion of the monomers of the hydrophilic blocks of the block copolymers are bound to the linking groups by formula (FX2) and each $R^1$-$R^6$ is independently hydrogen, $C_1$-$C_{20}$ alkyl, $C_5$-$C_{20}$ aryl, $C_1$-$C_{20}$ acyl, $C_2$-$C_{20}$ alkenyl, $C_2$-$C_{20}$ alkynyl, $C_5$-$C_{20}$ alkylaryl, halo, amine, hydroxyl, carboxyl, $C_1$-$C_{20}$ alkoxycarbonyl, or a natural or non-natural amino acid or fragment (e.g., side chain) thereof. In an optical agent of the invention, at least a portion of the monomers of the hydrophilic blocks of the block copolymers are bound to the linking groups by formula (FX2) and at least one of, and optionally each of, $R^1$-$R^6$ is independently hydrogen, $C_1$-$C_{10}$ alkyl, $C_5$-$C_{10}$ aryl, or $C_1$-$C_{10}$ acyl. In an embodiment, each e is independently is selected from the range of 1 to 5. In an optical agent of the invention, at least a portion of the monomers of the hydrophilic blocks of the block copolymers are bound to the linking groups by formula (FX2) and each of $Z^1$ and $Z^2$ is independently amide, $C_1$-$C_{10}$ alkylene, $C_3$-$C_{10}$ cycloalkylene, poly(alkylene glycol), $C_2$-$C_{10}$ alkenylene, $C_3$-$C_{10}$ cycloalkenylene, carbonyl, or $C_2$-$C_{10}$ alkynylene. In an embodiment, at least one of $Z^1$ and $Z^2$ is a substituent comprising —(CH$_2$CH$_2$O)$_b$— (PEG, poly(ethylene glycol)) wherein b is selected from the range of 1 to 10.

In an embodiment, at least a portion of the monomers of the hydrophilic blocks are bound to pyrazine-based linking groups via a amide bonding scheme (e.g., via amino carbonyl groups). In an embodiment, for example, at least a portion of the hydrophilic blocks of the block copolymers comprise monomers bound to linking groups having the formula:

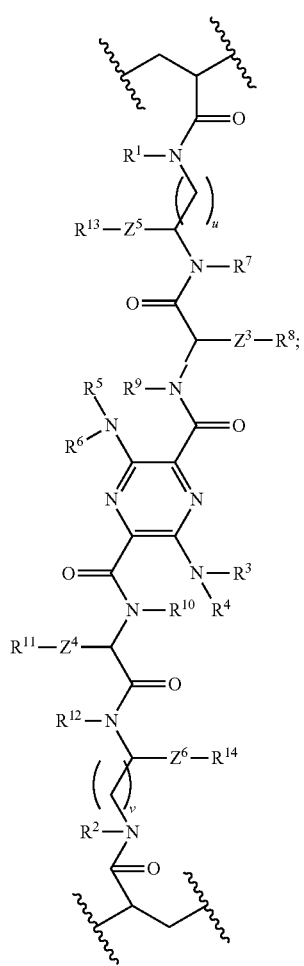

(FX3)

wherein each of $R^1$-$R^{14}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group or a natural or non-natural amino acid or fragment (e.g., side chain) thereof; each of u and v is independently selected from the range of 0 to 10; each of $Z^3$-$Z^6$ is independently

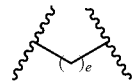

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein each e is independently is selected from the range of 0 to 10. In an embodiment, e is selected from the range of 1 to 5. The present invention includes compositions comprising enantiomers, diastereomers, and/or ionic forms (e.g., protonated and deprotonated forms) of formula (FX3).

In an embodiment of the compounds of formula (FX3), one or more CH$_2$ groups bound by u and v may be independently replaced by NH, O, S, a carbonyl (C=O), or a sulfonyl (S=O or O=S=O); two adjacent CH$_2$ groups may be replaced by —CH=CH— or —C≡C—.

In an embodiment of compounds of formula (FX3), at least one of $R^8$, $R^{11}$, $R^{13}$, and $R^{14}$ is

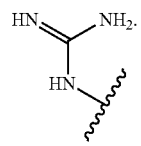

In an embodiment, each of $R^{15}$ and $R^{16}$ is independently a hydrogen or $C_1$-$C_5$ alkyl.

In an optical agent of the invention, at least a portion of the monomers of the hydrophilic blocks of the block copolymers are bound to the linking groups by formula (FX3) and each $R^1$-$R^{16}$ is independently hydrogen, $C_1$-$C_{20}$ alkyl, $C_5$-$C_{20}$ aryl, $C_1$-$C_{20}$ acyl, $C_2$-$C_{20}$ alkenyl, $C_2$-$C_{20}$ alkynyl, $C_5$-$C_{20}$ alkylaryl, halo, amine, hydroxyl, carboxyl, $C_1$-$C_{20}$ alkoxycarbonyl, or a natural or non-natural amino acid or fragment (e.g., side chain) thereof. In an optical agent of the invention, at least a portion of the monomers of the hydrophilic blocks of the block copolymers are bound to the linking groups by formula (FX3) and at least one of $R^1$-$R^{16}$, and optionally each of $R^1$-$R^{16}$, is independently hydrogen, $C_1$-$C_{10}$ alkyl, $C_5$-$C_{10}$ aryl, or $C_1$-$C_{10}$ acyl. In an embodiment, each e is independently is selected from the range of 1 to 5. In an optical agent of the invention, at least a portion of the monomers of the hydrophilic blocks of the block copolymers are bound to the linking groups by formula (FX3) and each of $Z^3$-$Z^6$ is independently amide, $C_1$-$C_{10}$ alkylene, $C_3$-$C_{10}$ cycloalkylene, poly(alkylene glycol), $C_2$-$C_{10}$ alkenylene, $C_3$-$C_{10}$ cycloalkenylene, carbonyl, or $C_2$-$C_{10}$ alkynylene. In an embodiment, at least one of $Z^3$-$Z^6$ is a substituent comprising —(CH$_2$CH$_2$O)$_b$— (PEG, poly(ethylene glycol)) wherein b is selected from the range of 1 to 10.

As will be understood by those having skill in the art, the present invention includes supramolecular structures and compositions cross linked via other types of covalent bonding known in the art of synthetic organic chemistry and polymer chemistry.

In an embodiment, at least a portion of the monomers of the hydrophilic blocks are bound to pyrazine-based linking groups such as pyrazine-based amino linking groups. In an embodiment, for example, at least a portion of the block copolymers and linking groups of the optical agent have the formula:

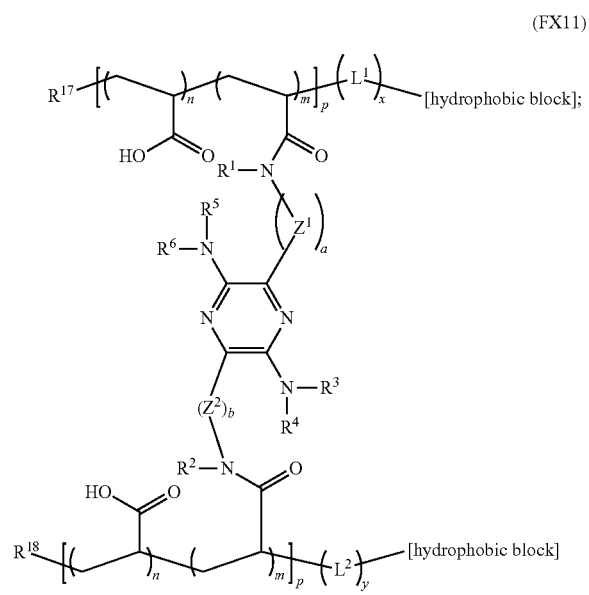

(FX11)

wherein each p is independently selected from the range of 20 to 250, wherein independently for each value of p, n is independently a number from 1 to 0 and m is independently a number from 1 to 0; wherein each of $R^1$-$R^6$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group or a natural or non-natural amino acid or fragment thereof; each of $R^{17}$ and $R^{18}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group, a natural or non-natural amino acid or fragment thereof or an additional hydrophilic block of the copolymers; each of $Z^1$, $Z^2$, $L^1$ and $L^2$ is independently

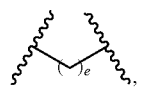

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein each e is independently selected from the range of 0 to 10; each of a and b is independently 0 or 1; wherein [hydrophobic block] is a hydrophobic block of the block copolymers; wherein each of x and y is independently 0 or 1. The present invention includes compositions comprising enantiomers, diastereomers, and/or ionic forms (e.g., protonated and deprotonated forms) of formula (FX11).

In an embodiment, at least a portion of the monomers of the hydrophilic blocks are bound to pyrazine-based linking groups having one or more guanidine or guanidine derivative moieties (e.g., side chain of the amino acid arginine). In an embodiment, for example, at least a portion of the block copolymers and linking groups of the optical agent have the formula:

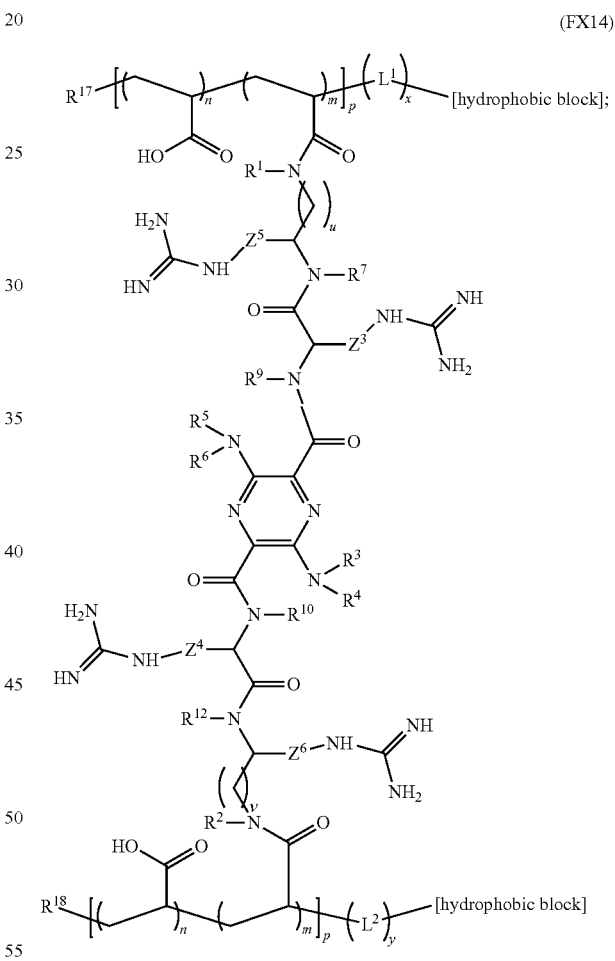

(FX14)

wherein each p is selected from the range of 20 to 250, wherein independently for each value of p, n is independently a number from 1 to 0 and m is independently a number from 1 to 0; wherein each of $R^1$-$R^7$, $R^9$, $R^{10}$, and $R^{12}$-$R^{14}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group or a natural or non-natural amino acid or fragment thereof; each of $R^{17}$ and $R^{18}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group, a natural or non-natural amino acid or fragment thereof or an additional hydrophilic block of the copolymers; each of $Z^3$-$Z^6$, $L^1$ and $L^2$ is independently

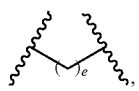

wherein one or more CH$_2$ groups may be replaced by NH, O, S, a carbonyl (C═O), or a sulfonyl (S═O or O═S═O); two adjacent CH$_2$ groups may be replaced by —CH═CH— or —C≡C—; and wherein each e is independently selected from the range of 0 to 10; each of u and v is independently selected from the range of 0 to 10; wherein [hydrophobic block] is a hydrophobic block of the block copolymers; wherein each of x and y is independently 0 or 1.

In an embodiment of the compounds of formula (FX14), one or more CH$_2$ groups bound by u and v may be independently replaced by NH, O, S, a carbonyl (C═O), or a sulfonyl (S═O or O═S═O); two adjacent CH$_2$ groups may be replaced by —CH═CH— or —C≡C—.

The present invention includes compositions comprising enantiomers, diastereomers, and/or ionic forms (e.g., protonated and deprotonated forms) of formula (FX13) and (FX14).

As shown in formulas (FX11) and (FX14), a portion of the polymer backbones of the block copolymers is shown in block parenthesis (i.e., the parenthesis with the subscript "p") indicating repeating units of the hydrophilic block. For each repeating unit in this portion of the polymer backbone n and m can independently have values between 0 and 1, indicating that the monomers of the repeating unit may vary in this embodiment along on the polymer backbone. This structure reflects that fact that the extent and structure of cross linking between cross linked block copolymers can vary along the polymer back bone. For example, n and m may both equal 1 for the first unit of the polymer backbone shown in formula (FX11) or (FX14), signifying that both cross linked and non-cross linked monomer groups are present in this unit, and m may equal 1 and n equal 0 in the second repeating unit of the polymer backbone signifying that only the cross linked monomer groups is present in the second unit. Accordingly, the optical agent of formula (FX11) or (FX14) represent a class of compositions having a variable extent of cross linking, for example, an extent of cross linking ranging from 1 to 75%, and optionally 20 to 75%. The hydrophilic block of the block copolymer may have any number of additional chemical domains. In an embodiment, for example, $R^{17}$ and/or $R^{18}$ are independently a substituent comprising —(CH$_2$CH$_2$O)$_b$— (i.e., (PEG, poly(ethylene glycol))), wherein b is selected from the range of 1 to 10.

In an embodiment, the hydrophilic groups of at least a portion of the block copolymers further comprise a poly(ethylene glycol) domain (PEG), for example a domain comprising —(CH$_2$CH$_2$O)$_b$— wherein h is selected from the range of 10 to 500. In an embodiment, the block copolymers include a PEG domain having from 50 to 250 repeating units. In an embodiment, the block copolymers include a PEG domain having from 20 to 100 repeating units. The PEG domain may be attached to another block of the copolymer using any suitable linking chemistry, as is known in the art. For example, PEG can be attached to a —C(═O)—NH group which may be originally a PAA group. In an embodiment, at least one of the blocks on the backbone includes —(CH$_2$CH$_2$O)$_b$— (PEG, poly(ethylene glycol)). The number of PEG repeating units may be any suitable number, including a total size of 1-5 kDa for the PEG group, in an embodiment. In an embodiment, b in the formula above is selected from the range of 1 to 10. The PEG group or any other substituent may be derivatized by any suitable group, such as a reactive group, to aid in subsequent chemistry steps or for any other desired purpose.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers, enantiomers and diastereomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, biological materials, reagents, synthetic methods, purification methods, analytical methods, assay methods and biological methods other than those specifically exemplified can be employed in the practice of the invention without resort to undue experimentation. All art-known functional equivalents, of any such methods, device elements, starting materials, biological materials, reagents, synthetic methods, purification methods, analytical methods, assay methods and biological methods are intended to be included in this invention. Whenever a range is given in the specification, for example, a pH range, a time range, a repeating-unit number range or a composition range, all intermediate ranges and subranges, as well as all individual values included in the ranges given are intended to be included in the disclosure. The term "number" is inclusive of integers, fractions and decimals. In particular, the term number used in a range includes all integers, fractions and decimals within that range.

Whenever a range is given in the specification, for example, a pH range, a time range, a repeating-unit number range or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention may be carried out using a large number of variations of the devices, device components, methods steps set forth in the present description. As will be obvious to one of skill in the art, methods and devices useful for the present methods can include a large number of optional composition and processing elements and steps.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

The present compositions, preparations and formulations can be used both as a diagnostic agent as well as a photodynamic therapeutic agent concomitantly. For example, an effective amount of the present compositions, preparations and formulations in a pharmaceutically acceptable formulation is administered to a patient. Administration is followed by a procedure that combines photodiagnosis and phototherapy. For example, a composition comprising compounds for combined photodiagnosis and phototherapy is administered to a patient and its concentration, localization, or other parameters is determined at the target site of interest. More than one measurement may be taken to determine the location of the target site. The time it takes for the compound to accumulate at the target site depends upon factors such as pharmcokinetics, and may range from about thirty minutes to two days. Once the site is identified, the phototherapeutic part of the procedure may be done either immediately after determining the site or before the agent is cleared from the site. Clearance depends upon factors such as pharmacokinetics.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations may also include aerosol formulation, creams, gels, solutions, etc. The present compositions, preparations and formulations are administered in doses effective to achieve the desired diagnostic and/or therapeutic effect. Such doses may vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations may also optionally include stabilizing agents and skin penetration enhancing agents.

Methods of this invention comprise the step of administering an "effective amount" of the present diagnostic and therapeutic compositions, formulations and preparations containing the present compounds, to diagnosis, image, monitor, evaluate treat, reduce or regulate a biological condition and/or disease state in a patient. The term "effective amount," as used herein, refers to the amount of the diagnostic and therapeutic formulation, that, when administered to the individual is effective diagnosis, image, monitor, evaluate treat, reduce or regulate a biological condition and/or disease state. As is understood in the art, the effective amount of a given composition or formulation will depend at least in part upon, the mode of administration (e.g. intravenous, oral, topical administration), any carrier or vehicle employed, and the specific individual to whom the formulation is to be administered (age, weight, condition, sex, etc.). The dosage requirements need to achieve the "effective amount" vary with the particular formulations employed, the route of administration, and clinical objectives. Based on the results obtained in standard pharmacological test procedures, projected daily dosages of active compound can be determined as is understood in the art. As used herein, "treat" means reduce or regulate a biological condition and/or disease state in a patient.

Any suitable form of administration can be employed in connection with the diagnostic and therapeutic formulations of the present invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The diagnostic and therapeutic formulations of this invention can be administered alone, but may be administered with a pharmaceutical carrier selected upon the basis of the chosen route of administration and standard pharmaceutical practice.

The diagnostic and therapeutic formulations of this invention and medicaments of this invention may further comprise one or more pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

The invention may be further understood by the following non-limiting examples, which in part, describe preparation and use of the optical agent before association with a therapeutic agent.

EXAMPLE 1

Photonic Shell-Crosslinked Nanoparticle Probes for Optical Imaging and Monitoring Shell-crosslinked micelles have been shown to be excellent nanostructural platforms for a variety of biomedical applications, ranging from the delivery of large payloads of chemotherapeutics and diagnostic agents to the in vivo targeting of such entities to tumors via the external multivalent presentation of tissue specific ligands. The outstanding versatility of these systems is derived from both the ease with which they are produced (by placing amphiphilic block copolymers into a solvent that is selective for solubilizing a portion of the polymer chain segments), and the final core-shell or other (multi) compartment-type morphologies. In general, for shell-crosslinked knedel-like (SCK) nanoparticles derived from amphiphilic block copolymers containing poly(acrylic acid) as the hydrophilic, crosslinkable component, non-functional diamines have been used to chemically crosslink the carboxylate-rich shells in order to generate stable discrete nanoparticles. Even in cases where the core domain is transformed from a hydrophobic block copolymer segment to a hydrophilic polymer chain or degraded into small molecule fragments through chemical excavation strategies, the covalently-crosslinked shell layer retains structural integrity, resulting in the formation of nanocage frameworks, which are able to undergo expansion and contraction under changing environmental conditions.

In this Example the use of the reversible hydrophobicity/hydrophilicity of the core domain to drive the block copolymer micelle assembly/disassembly in water without the aid of organic solvents, as a unique, green chemistry approach to the formation of SCKs is demonstrated. In this pursuit, it is shown that simple polymer nanoparticles can be fashioned into sophisticated sensing devices, by bringing together the concepts of reversible hydrophobicity and nanoparticle expansion/contraction, with the use of functional crosslinkers. The functional crosslinkers provide structural integrity and optical signals to both mediate and probe the local changes within the SCKs.

Photonic shell-crosslinked nanoparticles (SCKs) were prepared via crosslinking between fluorophores and micelles.

In an embodiment, the fluorophore-SCKs were assembled from the diblock copolymer precursor, poly(acrylic acid)$_{103}$-b-poly(p-hydroxystyrene)$_{41}$, PAA-b-PpHS, which was synthesized via nitroxide-mediated radical polymerization. Micelles were formed by first dissolving the block copolymer in water at high pH and then slowly decreasing the solution pH to 7, at which protonated PpHS block formed a hydrophobic core while maintenance of the deprotonated PAA block shaped a hydrophilic shell. The resulting micelle solution was incubated with the photoactive moiety, with the addition of EDCI to provide a nanoparticle having different amounts of optical agents and different degrees of crosslinking. The reaction mixture solutions were dialyzed against nanopure water for 4 days to remove the urea by-products and any non-attached photoactive groups. The nanoparticle dimensions were measured by atomic force microscopy (AFM) and transmission electron microscopy (TEM).

Experimental Section

Synthesis of poly(tert-butyl acrylate)$_{104}$ (5): To a flame-dried 50-mL Schlenk flask equipped with a magnetic stir bar and under N$_2$ atmosphere, at room temperature (rt), was added 2,2,5-trimethyl-3-(1'-phenylethoxy)-4-phenyl-3-azahexane (600 mg, 1.84 mmol), 2,2,5-trimethyl-4-phenyl-3-azahexane-3-nitroxide (20.0 mg, 0.092 mmol), and tert-butyl acrylate (31.5 g, 245 mmol). The reaction flask was sealed and stirred 10 min at rt (i.e. room temperature). The reaction mixture was degassed through three cycles of freeze-pump-thaw. After the last cycle, the reaction mixture was recovered back to rt and stirred for 10 min before being immersed into a pre-heated oil bath at 125° C. to start the polymerization. After 72 h, $^1$H NMR analysis showed 72% monomer conversion had been reached. The polymerization was quenched by quick immersion of the reaction flask into liquid N$_2$. The reaction mixture was dissolved in THF and precipitated into H$_2$O/MeOH (v:v, 1:4) three times to afford white powder, (19.3 g, 85% yield based upon monomer conversion); M$_{n,GPC}$=13,700 Da, PDI=1.1, DP=104.

Synthesis of poly(tert-butylacrylate)$_{104}$-b-poly(acetoxystyrene)$_{41}$ (6): To a flame-dried 50-mL Schlenk flask equipped with a magnetic stir bar and under N$_2$ atmosphere at rt, 5 (3.0 g, 0.22 mmol) and 4-acetoxystyrene (4.44 g, 27.4 mmol) were added. The reaction mixture was allowed to stir for 1 h at rt to obtain a homogenous solution. The reaction mixture was degassed through three cycles of freeze-pump-thaw. After the last cycle, the reaction mixture was recovered back to rt and stirred for 10 min before being immersed into a pre-heated oil bath at 125° C. to start the polymerization. After 6 h, 32% monomer conversion was reached, as analyzed by $^1$H NMR spectroscopy. After quenching by immersion of the reaction flask into a bath of liquid $N_2$, THF was added to the reaction mixture and the polymer was purified by precipitating into $H_2O$/MeOH (v:v, 1:4) three times to afford 6 as a white powder, (3.73 g, 83% yield); $M_{n,GPC}$=17,400 Da, PDI=1.3, DP=41.

Preparation of poly(tert-butyl acrylate)$_{104}$-b-poly(p-hydroxystyrene)$_{41}$ (7): To a 25-mL round bottom (RB) flask, (6) (3.0 g, 0.15 mmol) and MeOH (10 mL) were added and stirred 10 min at rt. The cloudy mixture was heated slowly to reflux. Immediately after the solution turned clear, a sodium methoxide solution in MeOH (25 wt %) (26 mg, 0.12 mmol) was added through syringe. The reaction mixture was further allowed to heat at reflux for 4 h. After cooling down to rt, the reaction mixture was precipitated in water with 4% acetic acid to afford 7 as white solid (2.6 g, 95% yield). $M_{n,NMR}$=18,600 Da.

Synthesis of poly(acrylic acid)$_{104}$-b-poly(p-hydroxystyrene)$_{41}$ (1): To a 50 mL RB flask equipped with a stir bar, was added 7 (2.5 g, 0.13 mmol) and trifluoroacetic acid (20.2 g, 177 mmol). The reaction mixture was allowed to stir for 24 h at rt. Excess acid was removed under vacuum. The residue was dissolved into 10 mL of THF and purified by dialysis against nanopure water (18.0 MΩ-cm) for three days and freeze-dried to afford 1 as a white powder (1.6 g, 95% yield). $M_{n,NMR}$=12,000 Da Preparation of Micelle 2 from 1: To a 50 mL of RB flask equipped with a magnetic stir bar was added 1 (2.0 mg, 0.16 µmol) and 15 mL of nanopure water. The pH value was adjusted to 12 by adding 1.0 M NaOH solution to afford a clear solution. The micellization was initiated after decreasing the pH value to 7 by adding dropwise 1.0 M HCl. After further stirring 12 h at rt, the micelle solution was used directly for construction of SCK 3 and 4.

Preparation of Shell-Crosslinked Nanoparticles (SCK 3 or 4) from Micelle 2: To a 50 mL RB flask equipped with a magnetic stir bar was added a solution of micelles in nanopure $H_2O$ (15.0 mL, 0.016 mmol of carboxylic acid residues). To this solution, was added a solution of 3,6-diamino-$N^2$,$N^5$-bis (2-aminoethyl)pyrazine-2,5-dicarboxamide (0.397 mg, 1.12 µmol (6.25 mol % relative to the acrylic acid residues) for 12.5% crosslinking extent; or 0.794 mg, 2.24 µmol (12.5 mol % relative to the acrylic acid residues) for 25% crosslinking extent) in 1 mL nanopure $H_2O$. The reaction mixture was allowed to stir for 2 h at rt. To this solution was added, dropwise via a syringe pump over 1 h, a solution of 1-[3'-(dimethylamino)propyl]-3-ethylcarbodiimide methiodide (EDCI, 0.849 mg, 2.86 µmol for 12.5% crosslinking extent; or 1.70 mg, 5.72 µmol for 25% crosslinking extent) in nanopure $H_2O$ (1.0 mL) and the reaction mixture was further stirred for 16 h at rt. Finally, the reaction mixture was transferred to pre-soaked dialysis tubing (MWCO ca. 3,500 Da) and dialyzed against nanopure water for 3 d to remove the small molecule starting materials and by-products, and afford aqueous solutions of SCK 3 and 4. SCK solutions for DLS, UV-vis, and fluorescence studies were further partitioned into six vials each containing 5 mM PBS (with 5 mM NaCl) at pH values of 4.5, 6.1, 8.0, 9.5, and 11.

Synthesis of 3,6-diamino-$N^2$,$N^5$-bis(2-aminoethyl)pyrazine-2,5-dicarboxamide: A mixture of sodium 3,6-diaminopyrazine-2,5-dicarboxylate (500 mg, 2.07 mmol), tert-butyl 2-aminoethylcarbamate (673 mg, 4.20 mmol), HOBt (836 mg, 5.46 mmol) and EDCI (1.05 g, 5.48 mmol) in DMF (25 mL) was allowed to stir for 16 h and was then concentrated. The residue was partitioned with 1 N $NaHSO_4$ (200 mL) and EtOAc (200 mL). The organic layer was separated and washed with water (200 mL×3), sat. $NaHCO_3$ (200 mL×3) and brine. Dried with $MgSO_4$, filtered and concentrated to afford the bisamide as an orange foam. 770 mg, 76% yield. $^1$H NMR (300 MHz, DMSO-$d_6$) major conformer, δ 8.44 (t, J=5.7 Hz, 2 H), 6.90 (t, J=5.7 Hz, 2 H), 6.48 (br, 4 H), 2.93-3.16 (m, 8 H), 1.37 (s, 9 H), 1.36 (s, 9 H) ppm. $^{13}$C NMR (75 MHz, DMSO-$d_6$), δ 165.1, 155.5, 155.4, 146.0, 126.2, 77.7, 77.5, 45.2, 44.5, 28.2 ppm. LC-MS (15-95% gradient acetonitrile in 0.1% TFA over 10 min), single peak retention time=7.18 min on 30 mm column, (M+H)$^+$=483 amu. To the product (770 mg, 1.60 mmol) in methylene chloride (100 mL), was added TFA (25 mL) and the reaction was stirred at room temperature for 2 h. The mixture was concentrated and the residue was dissolved into methanol (15 mL). Diethyl ether (200 mL) was added and the orange solid precipitate was isolated by filtration and dried at high vacuum to afford an orange powder. 627 mg, 77% yield. $^1$H NMR (300 MHz, DMSO-$d_6$) δ 8.70 (t, J=6 Hz, 2 H), 7.86 (br, 6 H), 6.50 (br, 4 H), 3.46-3.58 (m, 4 H), 3.26-3.40 (m, 4 H) ppm. $^{13}$C NMR (75 MHz, DMSO-$d_6$) δ 166.4, 146.8, 127.0, 39.4, 37.4 ppm. LC-MS (15-95% gradient acetonitrile in 0.1% TFA over 10 min), single peak retention time=2.60 min on 30 mm column, (M+H)$^+$=283 amu. UV-vis (100 µM in PBS) $\lambda_{abs}$=435 nm. Fluorescence (100 nM) $\lambda_{ex}$=449 nm, $\lambda_{em}$=562 nm. The product was converted to the HCl salt by coevaporation (3×100 mL) with 1 N aqueous HCl.

EXAMPLE 2

General Methods for Photonic Cross-Linker Synthesis

Analytical thin layer chromatography (TLC) was performed on Analtech 0.15 mm silica gel 60-GF$_{254}$ plates. Visualization was accomplished with exposure to UV light, exposure to Iodine or by dipping in an ethanolic PMA solution followed by heating. Solvents for extraction were HPLC or ACS grade. Chromatography was performed by the method of Still with Merck silica gel 60 (230-400 mesh) with the indicated solvent system. NMR spectra were collected on a Bruker ARX-500, or Varian Mercury-300 spectrometer. $^1$H NMR spectra were reported in ppm from tetramethylsilane on the δ scale. Data are reported as follows: Chemical shift, multiplicity (s=singlet, d=doublet, t=triplet, q=quartet, m=multiplet, b=broadened, obs=obscured), coupling constants (Hz), and assignments or relative integration. $^{13}$C NMR spectra were reported in ppm from the central deuterated solvent peak. Grouped shifts are provided where an ambiguity has not been resolved. Preparative reversed phased liquid chromatography runs were conducted on a low pressure system employing an AllTech Model 7125 Rheodyne Injector Valve with a 5 mL sample loop, an AllTech Model 426 pump, an ISCO UA-6 absorbance detector with built-in recorder, peak separator and type 11 optical unit, an ISCO Foxy 200 fraction collector and using Lobar LiChroprep RP-18 (40-63 µm) prepacked columns and on a Waters Autopurification System using a Waters XBrigdge Preparative C18 OBD 30×150 mm column. LCMS were run on a Shimadzu LCMS-2010A using Agilent Eclipse (XDB-C18, 4.6×30 mm, 3.5-Micron) Rapid Resolution Cartridges and Agilent Eclipse (XDB-C18 4.6×250 mm, 3.5-Micron) Columns. GCMS were run on a Varian Saturn 2000 using a DB5 capillary column (30 m×0.25 mm I.D., 1.0µ film thickness). MALDI mass spectra were run on a PE Biosystems Voyager System 2052. Electronic absorption spectra were measured in phosphate buffered saline using a Shimadzu UV-3101PC UV-VIS-NIR scanning spectrophotometer. Emission spectra were recorded in phosphate buffered saline using a Jobin Yvon Fluorolog-3 fluorescence spectrometer.

Figure 4:
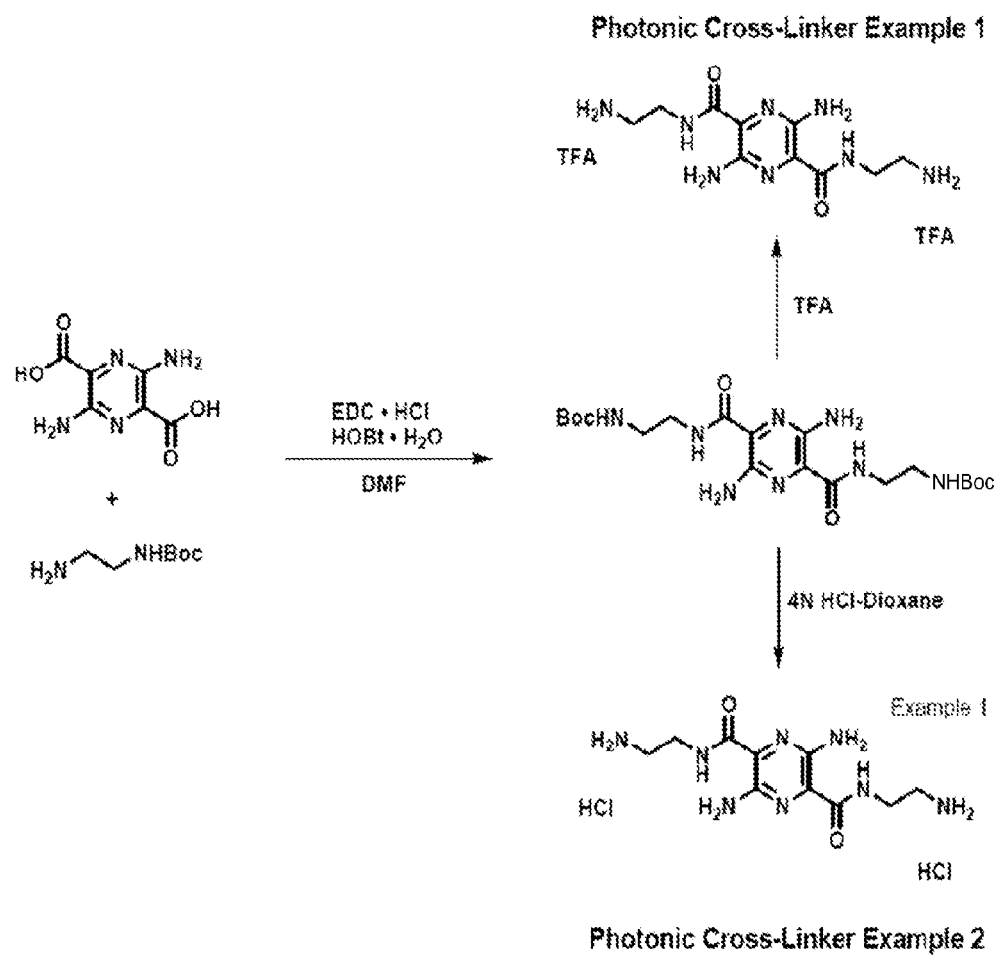
FIG. 4 depicts a synthetic scheme showing synthesis of Photonic Cross-Linker of Examples 1 and 2.

Abbreviations
AFM Atomic Force Microscopy
Arg Arginine
DMF Dimethyl formamide
DLS Dynamic Light Scattering
DP Degree of Polymerization
Dz Intensity averaged hydrodynamic diameter
Dn Number averaged hydrodynamic diameter
EDC-HCl 1-(3-Dimethylaminopropyl)-3-ethylcarbodiimide hydrochloride
ESI Electrospray Ionization
EtOAc Ethyl Acetate
GPC Gel Permeation Chromatography
HOBt-H2O 1-Hydroxybenzotriazole hydrate
HRMS High Resolution Mass Spectrometry
IR Infrared Spectroscopy
LCMS Liquid Chromatography-Mass Spectrometry
MeOH Methanol
Mn Number Average Molecular Weight
MS Mass Spectrometry
MWCO Molecular Weight Cut-Off
NMR Nuclear Magnetic Resonance Spectroscopy
PBS Phosphate Buffered Saline
PDI Polydispersity Index
PMA Phosphomolybdic acid stain
PTA Phosphotungstic acid stain
SCK Shell Cross-Linked Nanoparticle
TEA Triethylamine
TEM Transmission Electron Microscopy
TFA Trifluoroacetic acid
THF Tetrahydrofuran
TLC Thin Layer Chromatography Photonic Cross-Linker Chemistry Photonic Cross-Linker Example 1: 3,6-diamino-$N^2,N^5$-bis (2-aminoethyl)pyrazine-2,5-dicarboxamide bis-TFA salt. FIG. 4 illustrates a synthetic pathway for production of Photonic Cross-linker Example 1.

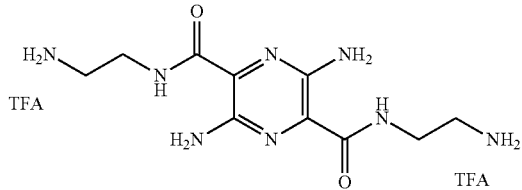 [SMILES: NCCNC(=O)c1nc(N)c(C(=O)NCCN)nc1N]

Step 1. Synthesis of 3,6-diamino-$N^2,N^5$-bis[2-(tert-butoxycarbonyl)aminoethyl]pyrazine-2,5-dicarboxamide

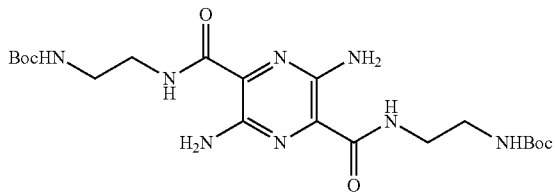 [SMILES: CC(C)(C)OC(=O)NCCNC(=O)c1nc(N)c(C(=O)NCCNC(=O)OC(C)(C)C)nc1N]

A mixture of sodium 3,6-diaminopyrazine-2,5-dicarboxylate (500 mg, 2.07 mmol), tert-butyl 2-aminoethylcarbamate (673 mg, 4.20 mmol), HOBt-H$_2$O (836 mg, 5.46 mmol) and EDC-HCl (1.05 g, 5.48 mmol) in DMF (25 mL) was stirred for 16 h and concentrated. The residue was partitioned with EtOAc (100 mL) and 1N NaHSO$_4$ (100 mL). The layers were separated and the EtOAc solution was washed with water (100 mL), saturated sodium bicarbonate (100 mL) and brine (100 mL). The EtOAc layer was dried (MgSO$_4$), filtered and concentrated to afford 770 mg (76% yield) of the bisamide as an orange foam: $^1$H NMR (300 MHz, DMSO-d$_6$), major conformer, δ 8.44 (t, J=5.7 Hz, 2 H), 6.90 (t, J=5.7 Hz, 2 H), 6.48 (bs, 4 H), 2.93-3.16 (complex m, 8 H), 1.37 (s, 9 H), 1.36 (s, 9 H). $^{13}$C NMR (75 MHz, DMSO-d$_6$), conformational isomers δ 165.1 (s), 155.5 (bs), 155.4 (bs), 146.0 (s), 126.2 (s), 77.7 (bs), 77.5 (bs), 45.2 (bt), 44.5 (bt), 28.2 (q).

Step 2. To the product from step 1 (770 mg, 1.60 mmol) in methylene chloride (100 mL) was added TFA (25 mL) and the reaction was stirred at room temperature for 2 h. The mixture was concentrated and the residue taken up into methanol (15 mL). Ether (200 mL) was added and the orange solid precipitate was isolated by filtration and dried at high vacuum to afford 627 mg (77% yield) of Photonic Cross-Linker Example 1 as an orange powder: $^1$H NMR (300 MHz, DMSO-d$_6$), δ 8.70 (t, J=6 Hz, 2 H), 7.86 (bs, 6 H), 6.50 (bs, 4 H), 3.46-3.58 (m, 4 H), 3.26-3.40 (m, 4 H). $^{13}$C NMR (75 MHz, DMSO-d$_6$) δ 166.4 (s), 146.8 (s), 127.0 (s), 39.4 (t), 37.4 (t). LCMS (5-95% gradient acetonitrile in 0.1% TFA over 10 min), single peak retention time=3.62 min on 30 mm column, (M+H)$^+$=283. UV/vis (100 μM in PBS)$\lambda_{abs}$=435 nm. Fluorescence (100 nM) $\lambda_{ex}$=449 nm, $\lambda_{em}$=562 nm.

Photonic Cross-Linker Example 2: 3,6-diamino-$N^2,N^5$-bis (2-aminoethyl)pyrazine-2,5-dicarboxamide dihydrochloride. FIG. 4 illustrates a synthetic pathway for production of Photonic Cross-linker Example 2.

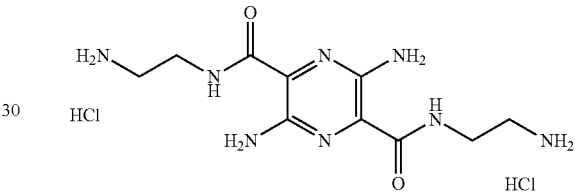

The product from Example 1, step 1 (351 mg, 0.73 mmol) was dissolved in 4N HCl-dioxane (35 mL) and the reaction mixture was stirred for 30 min at room temperature. The reaction was concentrated and triturated with ether (100 mL) to afford 226 mg (87% yield) of Photonic Cross-Linker Example 2 as an orange solid: MS (ESI) m/z=283 [M+H]$^+$. UV/vis (100 μM in PBS) $\lambda_{abs}$=435 nm. Fluorescence (100 nM) $\lambda_{ex}$=449 nm, $\lambda_{em}$=562 nm.

Alternative Synthesis of phototonic cross-linker 2: (3,6-diamino-$N^2,N^5$-bis(3-(2-(2-(3-aminopropoxy)ethoxy) ethoxy)propyl)pyrazine-2,5-dicarboxamide dihydrochloride): Step 1. Synthesis of tert-butyl 1,1'-(3,6-diaminopyrazine-2,5-diyl)bis(1-oxo-6,9,12-trioxa-2-azapentadecane-15,1-diyl)dicarbamate: A mixture of 3,6-diaminopyrazine-2,5-dicarboxylic acid (0.31 g, 1.56 mmol), tert-butyl 3-(2-(2-(3-aminopropoxy)ethoxy)propyl carbamate (1.00 g, 3.12 mmol), EDC.HCl (0.72 g, 3.74 mmol) and HOBt (0.50, 3.74 mmol) was stirred in DMF (35 mL) for 16 hr at room temperature. The residue was partitioned with EtOAc (100 mL) and saturated sodium bicarbonate (100 mL). The layers were separated and the EtOAc solution was washed with 5% aq. Citric acid (100 mL) and brine (100 mL). The EtOAc layer was dried (MgSO$_4$), filtered and concentrated to afford 1.2 g (48% yield) of the bisamide as an orange oil. The crude bis-amide was taken on to the next step with no further purification: HRMS calcd for C$_{36}$H$_{66}$N$_8$O$_{12}$Na, [M+Na]$^+$=825.4692 g/mol; Observed, 825.4674 g/mol.

Step 2. To the crude product mixture from step 1 (~1.20 g, 1.50 mmol) was added 4N HCl-Dioxane (10 mL) and the resulting mixture was stirred for 1 hr at room temperature. Concentration, in vacuo and pumping at high vacuum afforded 910 mg (90% yield) product as a viscous red oil: IR (NaCl): 2957, 2940, 1809, 1751, 1231, 1098, 1070, 866, 833, 775 cm$^{-1}$. LCMS (5-95% gradient acetonitrile in 0.1% TFA over 10 min), single peak retention time=5.70 min on 30 mm column, HRMS calcd. for $C_{72}H_{136}N_{10}O_{32}$ $[M+H]^+$= 603.3824 g/mol. Observed M+H=603.3823 g/mol. UV/vis (100 μM in PBS) $\lambda_{abs}$=435 nm. Fluorescence (100 nM) $\lambda_{ex}$=449 nm, $\lambda_{em}$=562 nm.

Figure 5:
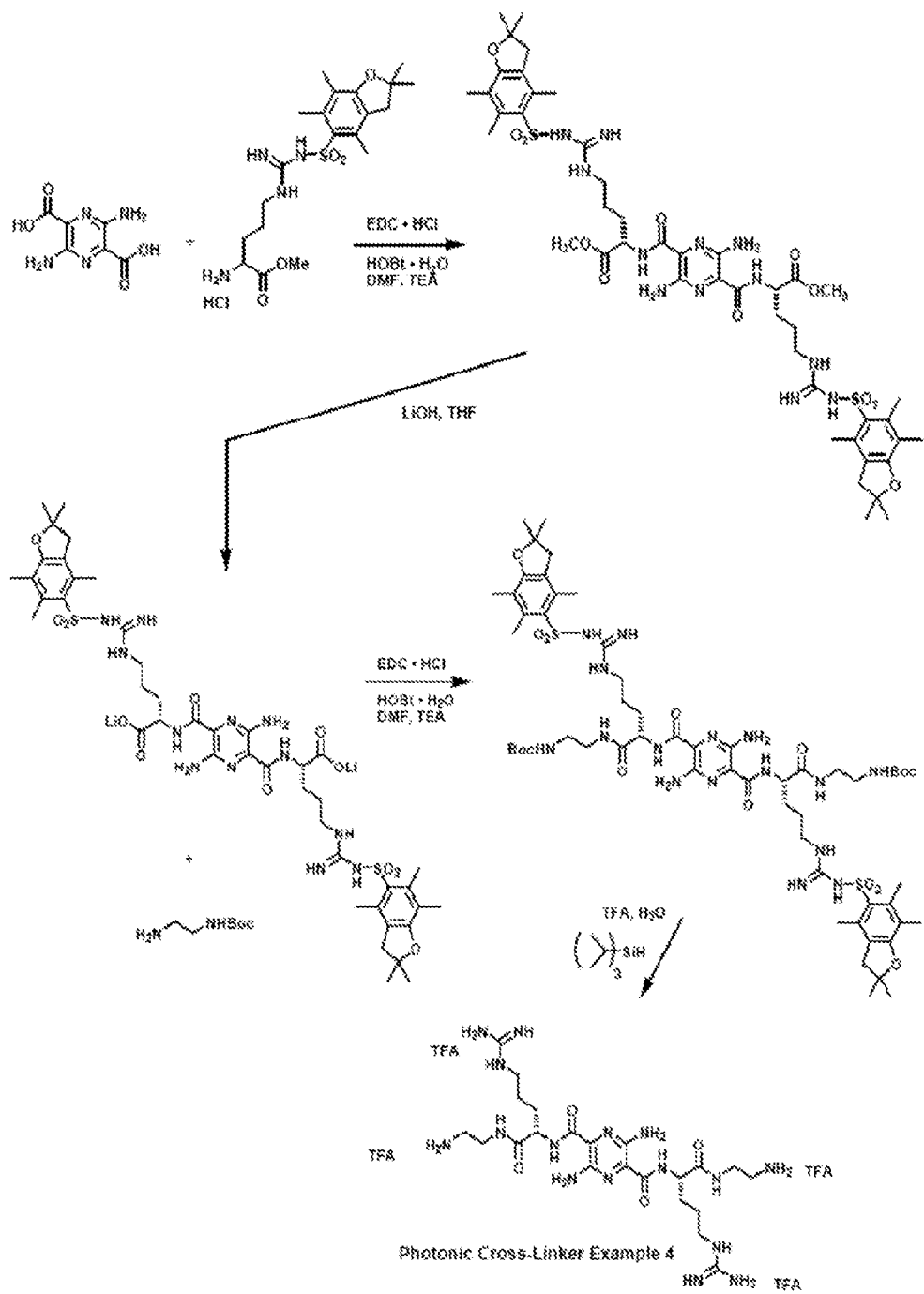
FIG. 5 depicts a synthetic scheme showing synthesis of Photonic Cross-Linker Example 4.
Figure 6:
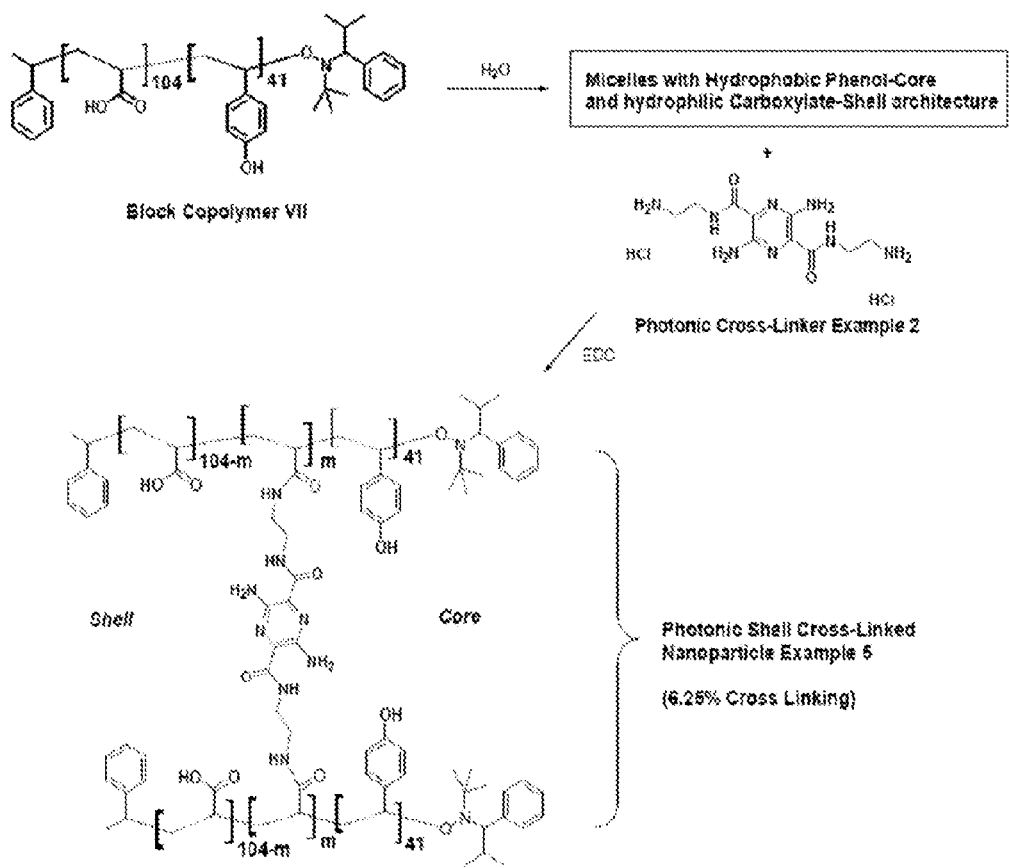
FIG. 6 depicts a synthetic scheme showing synthesis of Photonic Shell Cross-Linked Nanoparticle Example 5.
Figure 7:
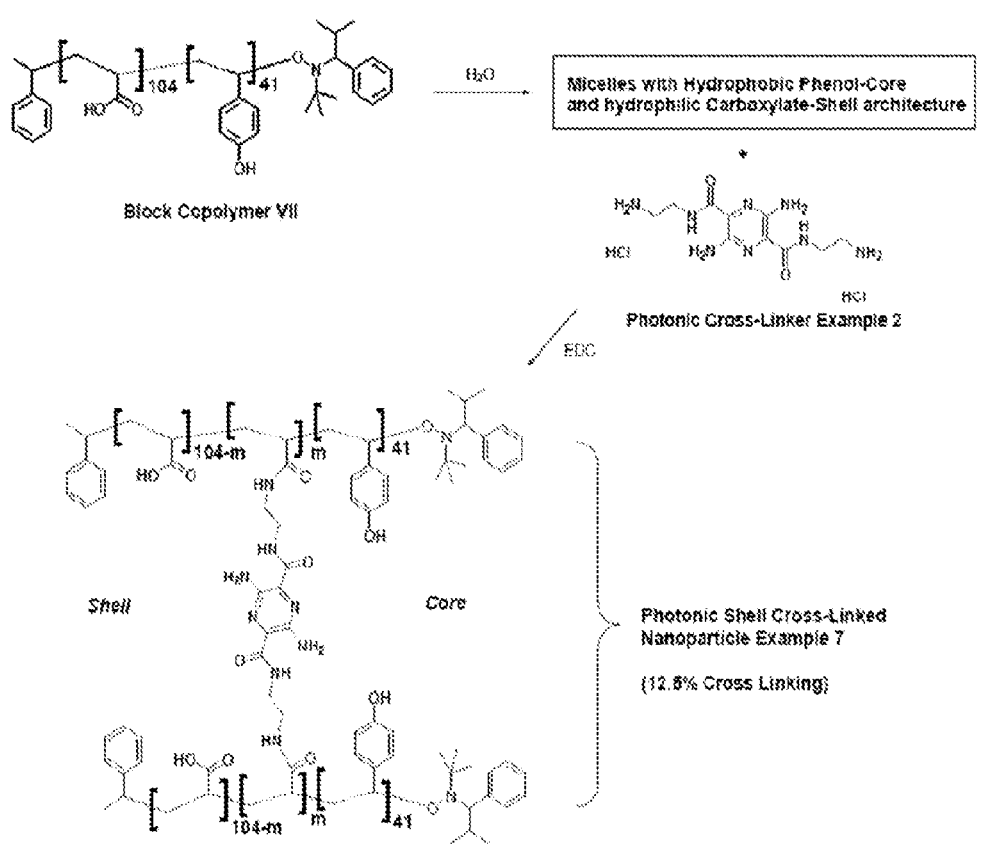
FIG. 7 depicts a synthetic scheme showing synthesis of Photonic Shell Cross-Linked Nanoparticle Example 7.

Photonic Cross-Linker Example 4: 3,6-Diamino-N2,N5-bis[N-(2-aminoethyl)-Arginine amide]-pyrazine-2,5-dicarboxamide tetra TFA salt. FIG. 5 illustrates a synthetic pathway for production of Photonic Cross-linker Example 4.

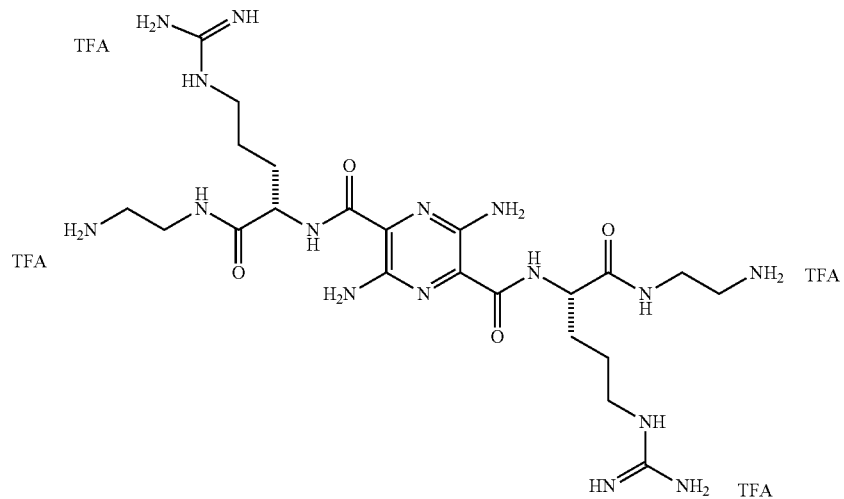

Step 1. Synthesis of 3,6-Diamino-N2,N5-bis(N-pbf-Arginine methyl ester)-pyrazine-2,5-dicarboxamide

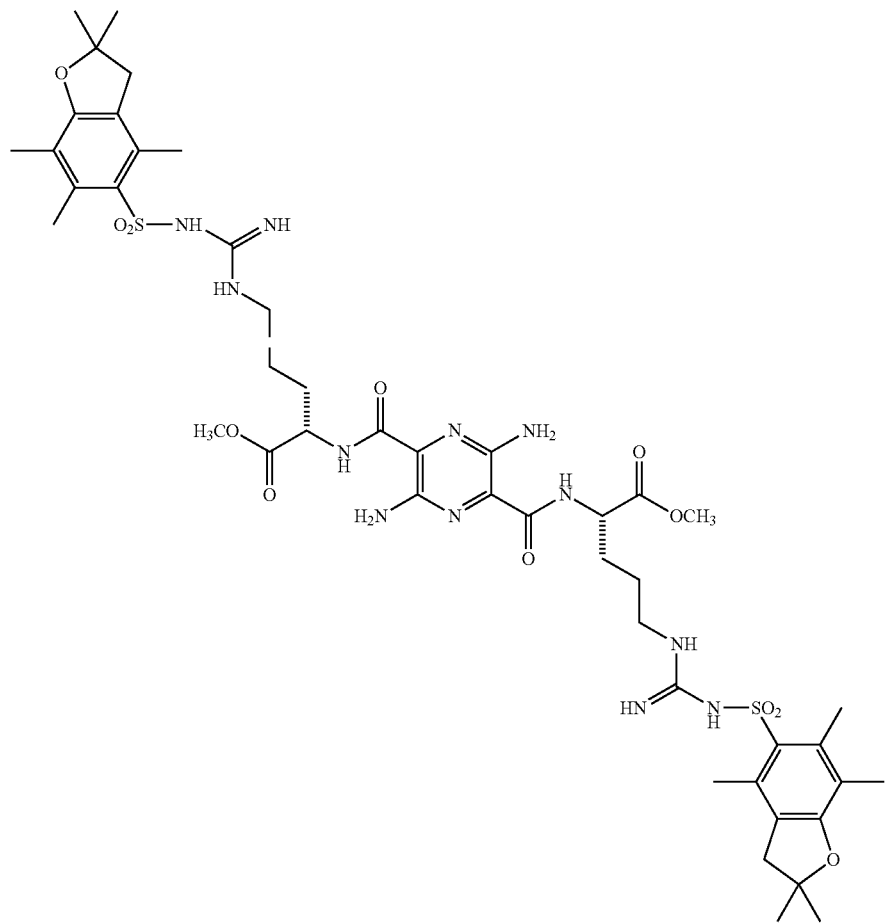

A mixture of 3,6-diaminopyrazine-2,5-dicarboxylic acid (0.90 g, 4.54 mmol), H-Arg(pbf)-OMe.HCl (4.77 g, 9.99 mmol), EDC (1.53 g, 9.99 mmol), HOBt (1.34 g, 9.99 mmol) and TEA (726 μL, 9.99 mmol) was stirred in DMF (35 mL) for 16 hr at room temperature. Concentration and workup as in Photonic Cross-Linker Example 1 followed by filtration through a plug of silica gel afforded the crude bis-amide which was taken on to the next step with no further purification.

Step 2. Synthesis of 3,6-Diamino-N2,N5-bis(N-pbf-Arginine)-pyrazine-2,5-dicarboxamide di-lithium salt

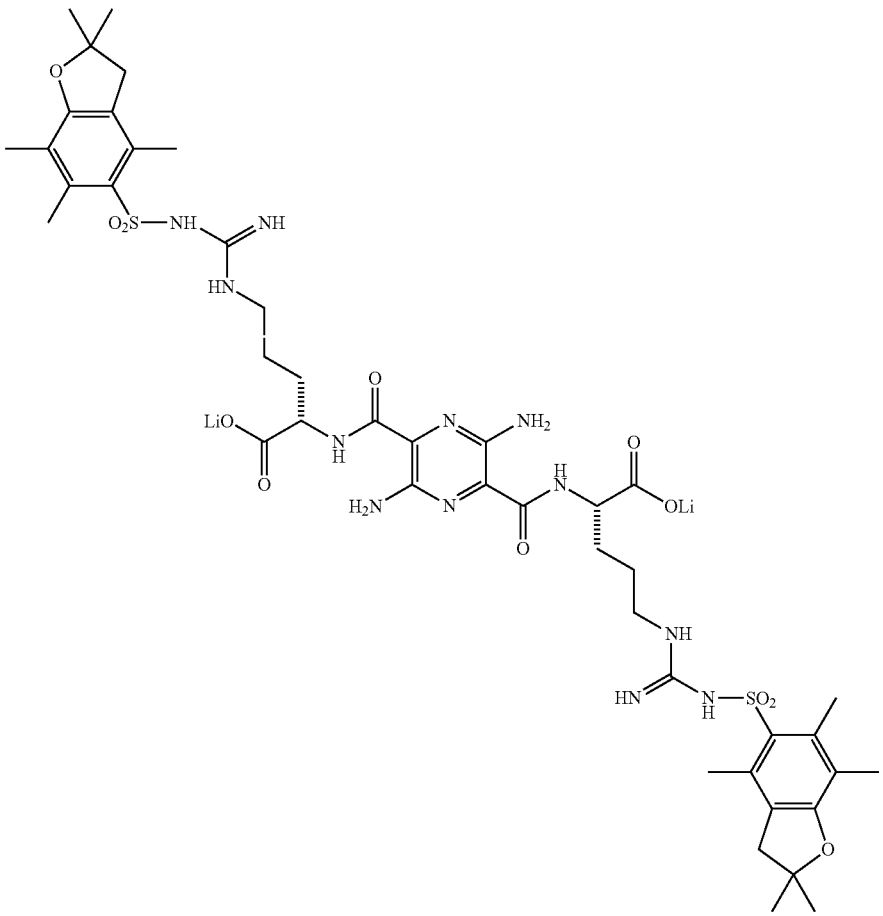

A solution of the product from Step 1 (2.40 g, 2.30 mmol) in THF (35 mL) was treated with a solution of lithium hydroxide (276 mg 11.5 mmol) in water (5.0 mL). After stirring for 1 hr at room temperature, HPLC analysis indicated reaction was complete. The reaction was quenched by the addition of dry ice and concentrated. This material was used in the next step without further purification.

Step 3. Synthesis of 3,6-Diamino-$N^2,N^5$-bis[N-(2-Bocaminoethyl)-Arginine amide]-pyrazine-2,5-di-carboxamide

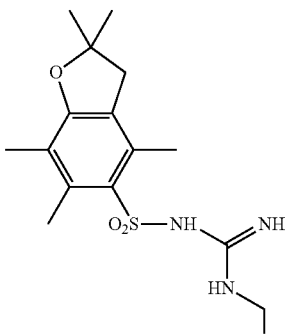

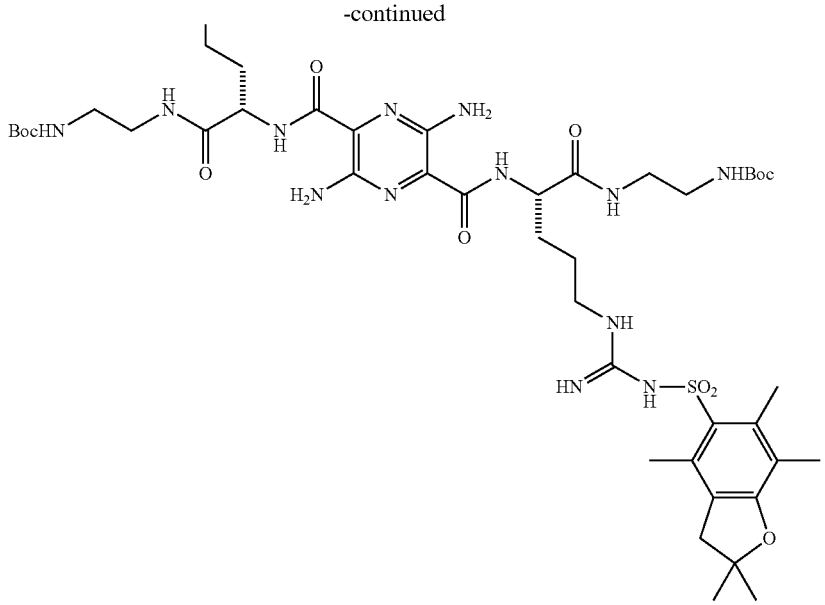

A mixture of the product from Step 2 (1.00 g, 0.97 mmol), tert-butyl 2-aminoethyl-carbamate (350 mg, 2.19 mmol), EDC.HCl (420 mg, 2.19 mmol) HOBt (290 mg, 2.15 mmol) and TEA (~0.5 mL) in DMF (50 mL) was stirred at room temperature for 16 h. The reaction was concentrated and the residue was processed as in Photonic Cross-Linker Example 1 to afford 1.05 g of product as a red semi-solid: MS (ESI) [M+H]$^+$=1300; [M+Na]$^+$=1323. This material was used in the next step without further purification.

Step 4. Synthesis of Photonic Cross-Linker Example 4. To the product from Step 3 (900 mg, 0.69 mmol) was added TFA (9.25 mL), water (25 µL), and triisopropyl silane (25, µL). The resulting mixture was stirred at room temperature for 72 h (convenience—over weekend). The reaction mixture was concentrated. The residue was purified by preparative HPLC (C18, 30×150 mm column, 5% ACN in H$_2$O to 95% over 12 min, 0.1% TFA) to afford 178 mg (26% yield) of Photonic Cross-Linker Example 4 as a red foam: HRMS calcd for C$_{22}$H$_{43}$N$_{16}$O$_4$, 595.3648 [M+H]$^+$. found, 595.3654.

Poly(acrylic acid)-b-poly(p-hydroxystyrene) Chemistry: Synthesis of block copolymers via nitroxide-mediated radical polymerization Synthesis of poly(tert-butylacrylate)$_{104}$ (I): In a 50-mL Schlenk flask with a magnetic stir bar, 2,2,5-trimethyl-3-(1-phenylethoxy)-4-phenyl-3-azahexane (500 mg, 1.34 mmol), 2,2,5-trimethyl-4-phenyl-3-azahexane-3-nitroxide (17.0 mg, 0.077 mmol), and tert-butyl acrylate (16.4 g, 128 mmol) were mixed together. The reaction mixture underwent three cycles of freeze-pump-thaw. The reaction was heated to 125° C. rapidly in a pre-heated oil bath. After 23 hrs, the reaction was quenched in liquid nitrogen. The reaction mixture was dissolved in THF and precipitated in 20% H$_2$O in MeOH three times to afford white powder, (7.17 g, 86% yield); M$_n$=13,700 Da, PDI=1.1, DP=40, conv=61%.

Synthesis of poly(tert-butylacrylate)$_{104}$-b-poly(acetoxystyrene)$_{41}$ (II): In a 50-mL Schlenk flask, I (2.0 g, 0.37 mmol), 4-acetoxystyrene (5.95 g, 37 mmol), and DMF (0.5 mL) was added to obtain a homogenous mixture. The reaction mixture was heated to 125° C. in a pre-heated oil bath and heated under stirring for 23 h. The reaction was dissolved in THF and precipitated in 20% H$_2$O in MeOH three times to afford white powder, (5.81 g, 91% yield); M$_n$=17,402 Da, PDI=1.3, DP=70, conv=80%.

Synthesis of poly(tert-butylacrylate)$_{110}$ (III): In a 50-mL Schlenk flask with a magnetic stir bar, 2,2,5-trimethyl-3-(1-phenylethoxy)-4-phenyl-3-azahexane (600 mg, 1.84 mmol), 2,2,5-trimethyl-4-phenyl-3-azahexane-3-nitroxide (20.0 mg, 0.092 mmol), and tert-butyl acrylate (31.5 g, 245 mmol) were mixed together. The reaction mixture underwent three cycles of freeze-pump-thaw. The reaction was heated to 125° C. rapidly in a pre-heated oil bath. After 72 hrs, the reaction was quenched in liquid nitrogen. The reaction mixture was dissolved in THF and precipitated in 20% H$_2$O in MeOH three times to afford white powder, (19.33 g, 73% yield); M$_n$=14,400 Da, PDI=1.1, DP=40, conv=61%.

Synthesis of poly(tert-butylacrylate)$_{110}$-b-poly(acetoxystyrene)$_{207}$ (IV): In a 50-mL Schlenk flask, III (1.70 g, 0.108 mmol), 4-acetoxystyrene (11.87 g, 64.6 mmol), 2,2,5-trimethyl-4-phenyl-3-azahexane-3-nitroxide (1.19 mg, 5.39 µmol), and DMF (4.0 mL) was added to obtain a homogenous mixture. The reaction mixture was heated to 125° C. in a pre-heated oil bath and let stir for 8 h. The reaction was dissolved in THF and precipitated in 20% H$_2$O in MeOH three times to afford white powder, (3.84 g, 74% yield); M$_n$=48,300 Da, PDI=1.3, DP=200, conv=35%.

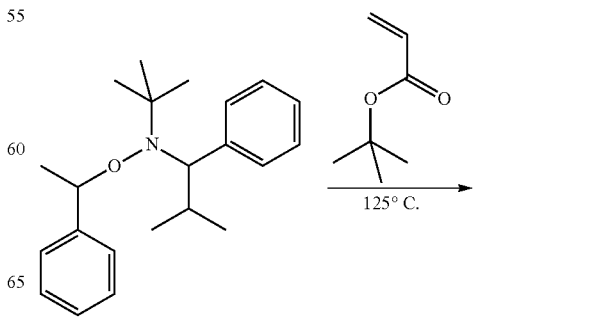

-continued

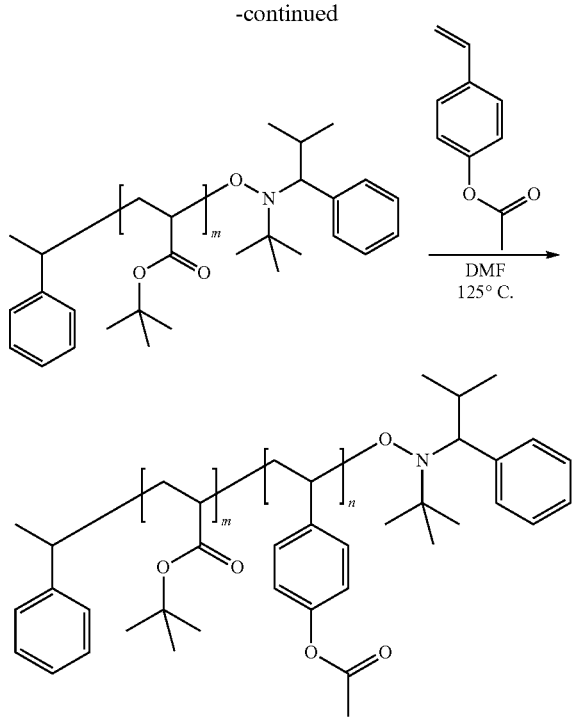

| Conditions | Characterizations |
|---|---|
| m = 104  23 h, 61% conv.  86% yield | $M_n^{GPC}$ = 13,700 Da  PDI = 1.1 |
| m = 110  72 h, 61% conv.  n = 207  73% yield | $M_n^{GPC}$ = 14,400 Da  PDI = 1.1 |

| Condition | Characterizations |
|---|---|
| 23 h, 80% conv.  90% yield | $M_n^{GPC}$ = 17,400 Da  PDI = 1.3 |
| 8 h, 35% conv.  74% yield | $M_n^{GPC}$ = 48,300 Da  PDI = 1.3 |

Hydrolysis of II or IV to afford poly(tert-butylacrylate)$_{104}$-b-poly(p-hydroxystyrene)$_{41}$ (V) or poly(tert-butylacrylate)$_{110}$-b-poly(p-hydroxystyrene)$_{207}$ (VI): In a 25-mL rb flask, II (3.0 g, 0.148 mmol) or IV (3.84 g, 0.08 mmol) and MeOH (10 mL) were added and let stirred at rt for 10 min. A cloudy mixture was heated slowly to reflux. Immediately after the solution cleared, sodium methoxide (25% in MeOH) (26 mg, 0.12 mmol or 76 mg, 0.35 mmol) was syringed into the reaction pot. The reaction mixture was allowed to heat at reflux for 4 h. The reaction mixture was precipitated in acetic acid (4% in water) to afford 2.6 g (95% yield), $M_n^{NMR}$=18,600 Da (V) or 3.0 g (97% yield), $M_n^{NMR}$=38,700 Da (VI).

Acidolysis of V or VI to afford poly(acrylic acid)$_{104}$-b-poly(p-hydroxystyrene)$_{41}$ (VII) or poly(acrylic acid)$_{110}$-b-poly(p-hydroxystyrene)$_{207}$ (VIII): In a Schlenk flask, V (2.5 g, 0.134 mmol) or VI (2.9 g, 0.075 mmol) was added with a stir bar. Excess amount of trifluoroacetic acid (20.2 g, 177 mmol) was syringed into the reaction pot to solubilize the block copolymer and let stirred for 24 h. The reaction mixture was dissolved in 10 mL of methylene chloride. Residual acid and solvent were removed in vacuum. The purification process was repeated three times. Slightly pink solution was dialyzed against nanopure water for three days and freeze-dried to afford 1.6 g or 2.4 g of the white polymer (95% or 94% yield). IR (v): 3438 (OH inter-, intramolecular H-bond), 2928 (COOH dimer), 1654 (COOH intramolecular H-bond), 1560-1384 (COOH anion), 1249 (Aryl-OH), 1172-1123 (C—OH) cm$^{-1}$.

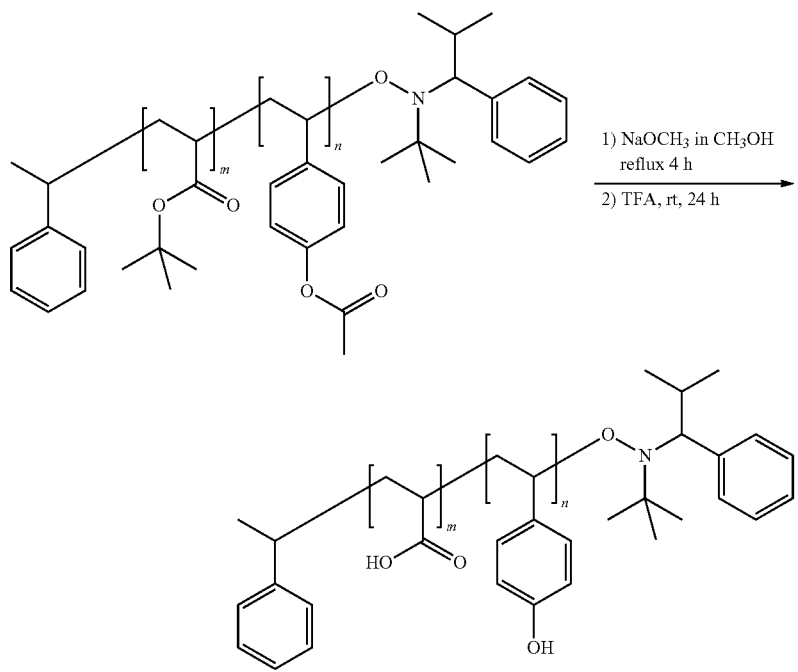

Photonic Shell Cross-Linked Nanoparticle Probe Chemistry

Preparation of micelles from VII or VIII: Micelles were prepared by first dissolving 2 mg of the block copolymer VII or VIII in 15 mL of nanopure water and stirring for 12 hrs.

Preparation of shell cross-linked nanoparticles (SCK) from micelles: Micelle solution pH was adjusted between 5 and 6. An electronic pipette was used to add 6.25 mol % or 12.5 mol % of diamine-terminated crosslinker (from stock solution with concentration 2.392 mg/mL or 6.2957 mg/mL) to the micelle solution and let stir for 3 hrs. To this reaction mixture was added dropwise, via a metering pump, a solution of 1-[3-(dimethylamino)propyl]-3-ethylcarbodiimide methiodide dissolved in nanopure water (12.5 mol % or 25.0 mol %). The reaction mixture was allowed to stir for 24 hrs at rt and was then transferred to presoaked dialysis membrane tube (MWCO ca. 3.5 kDa), and dialyzed against 5 mM PBS solution for three days to remove small molecules. SCK solutions for TEM and AFM studies were further dialyzed against nanopure water for three days and its pH adjusted to the desired value by addition of NaOH/HCl. SCK solutions for DLS, UV-vis, and fluorescence studies were further partitioned into six vials each containing 5 mM PBS at pH values 4.5, 6.1, 8.0, 9.5, 11.0, and 12.8.

Characterization Methods: Characterization of the polymers by gel permeation chromatography (GPC): Molecular weight and the molecular weight distribution (PDI) of the polymers I, II, III, and IV were determined by GPC. GPC was conducted on a Waters 1515 HPLC (Waters Chromatography, Inc.) equipped with a Waters 2414 differential refractometer, a PD2020 dual angle (15° and 90°) light scattering detector (Precision Detectors, Inc.), and a three column series PL gel 5 μm Mixed C, 500 Å, and $10^4$ Å, 300×7.5 mm columns (Polymer Laboratories Inc.). The system was equilibrated at 35° C. in anhydrous THF, which served as the polymer solvent and eluent with a flow rate of 1.0 mL/min. Polymer solutions were prepared at a known concentration (ca. 3 mg/mL) and an injection volume of 200 μL was used. Data collection and analysis were performed, respectively, with Precision Acquire software and Discovery 32 software (Precision Detectors, Inc.). Interdetector delay volume and the light scattering detector calibration constant were determined by calibration using a nearly monodispersed polystyrene standard (Pressure Chemical Co., $M_p$=90 kDa, $M_w/M_n$<1.04). The differential refractometer was calibrated with standard polystyrene reference material (SRM 706 NIST), of known specific refractive index increment do/dc (0.184 mL/g). The do/dc values of the analyzed polymers were then determined from the differential refractometer response.

Analysis of the SCKs or micelles by dynamic light scattering (DLS): Hydrodynamic diameters (Dz, Dn) and size distributions for the SCKs in aqueous solutions were determined by dynamic light scattering (DLS). The DLS instrumentation consisted of a Brookhaven Instruments Limited (Holtsville, N.Y.) system, including a model BI-200SM goniometer, a model BI-9000AT digital correlator, a model EMI-9865 photomultiplier, and a model 95-2 Ar ion laser (Lexel, Corp.; Farmindale, N.Y.) operated at 514.5 nm. Measurements were made at 20 (1° C. Prior to analysis, solutions were centrifuged in a model 5414 microfuge (Brinkman Instruments, Inc.; Westbury, N.Y.) for 4 min to remove dust particles. Scattered light was collected at a fixed angle of 90°. The digital correlator was operated with 522 ratio spaced channels, an initial delay of 0.1 μs, a final delay of 5.0 μs, and a duration of 15 min. A photomultiplier aperture of 200 μm was used, and the incident laser intensity was adjusted to obtain a photon counting of 200 kcps. Only measurements in which the measured and calculated baselines of the intensity autocorrelation function agreed to within 0.1% were used to calculate particle size. The calculations of the particle size distributions and distribution averages were performed with the ISDA software package (Brookhaven Instruments Company), which employed single-exponential fitting, cumulants analysis, and nonnegatively constrained least-squares particle size distribution analysis routines. A stock solution of PBS was made by dissolving 7.564 g of $NaH_2PO_4$, 19.681 g of $Na_2HPO_4$, and 11.688 g of NaCl in 4 liters of nanopure water. After complete dissolution, NaOH or HCl was added to achieve the desired pH value. The samples were filtered using 0.45 μm pore size nylon membrane filters in order to remove dust and any large, nonmicellar aggregates.

Analysis of the SCKs or micelles by atomic force microscopy (AFM): The height measurements and distributions for the SCCs were determined by tapping-mode AFM under ambient conditions in air. The AFM instrumentation consisted of a Nanoscope III BioScope system (Digital Instruments, Veeco Metrology Group; Santa Barbara, Calif.) and standard silicon tips (type, OTESPA-70; L, 160 μm; normal spring constant, 50 N/m; resonance frequency, 224-272 kHz). The sample solutions were drop (2 μL) deposited onto freshly cleaved mica and allowed to dry freely in air.

Analysis of the SCKs or micelles by transmission electron microscopy (TEM): TEM samples were diluted in water (9:1) and further diluted with a 1% phosphotungstic acid (PTA) stain (1:1). Carbon grids were prepared by a plasma treatment to increase the surface hydrophilicity. Micrographs were collected at 100,000× magnification and calibrated using a 41 nm polyacrylamide bead standard from NIST. Histograms of particle diameters were generated from the analysis of a minimum of 150 particles from at least three different micrographs.

Analysis of the SCKs by UV-vis/Fluorescence: UV-vis spectroscopy data were acquired on a Varian Cary 1E UV-vis spectrophotometer. Fluorescence spectroscopy data were acquired on a Varian Cary Eclipse Fluorescence spectrophotometer. Each sample was prepared independently from a nanoparticle stock solution at ca. 0.13 mg/mL. Sample solutions at various pH values from 4.5, 6.1, 8.0, 9.5, 11.0, and 12.8 were excited at $\lambda_{em}$=435 nm, and the fluorescence emission spectra in the range 445-800 nm were recorded.

EXAMPLE 3

Additional Linkage Systems

Additional chemistries were used for further photonic cross-linking systems. For example, the Example 4 crosslinker is shown below. The substituents and methods of preparing and using the linkers and cross-linkers described herein are known in the art with the information described herein.

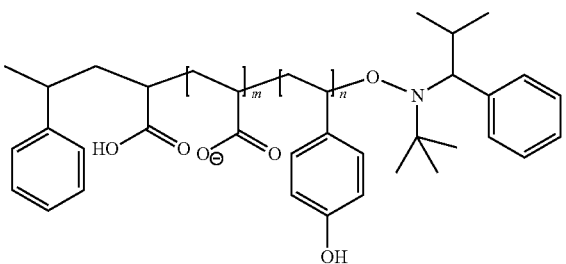

-continued

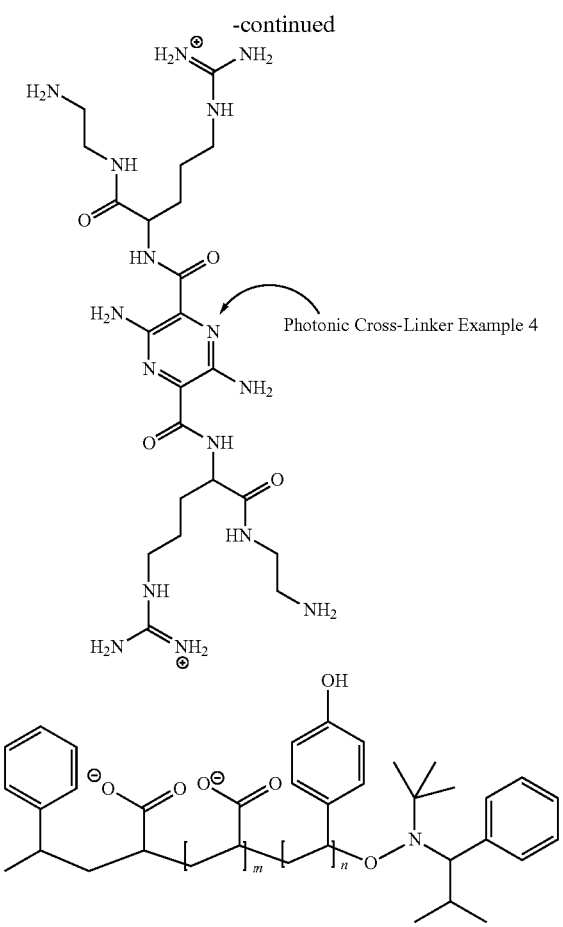

Photonic Cross-Linker Example 4

EXAMPLE 4

Construction of Functionalizable, Crosslinked Nanostructures

During the past decade, nanoscale micelles and vesicles assembled from amphiphilic block copolymer precursors have attracted much attention due to their promise for applications in the field of nanomedicine, ranging from controlled delivery of drugs and other diagnostic and therapeutic agents, to targeting of specific diseases and reporting of biological mechanisms via introduction of various functionalities. The thermodynamic stability of such nanoscale systems is only achieved above the critical micelle/vesicle concentration and their stability in vivo is therefore of concern. To overcome this restriction, covalent crosslinking throughout the shell/core domain of micelles or membrane domain of vesicles has been developed and demonstrated as an effective methodology for providing robust nanostructures.

In this Example, functional block copolymer systems were established based on N-acryloxysuccinimide (NAS) monomer building blocks, containing pre-installed active esters as amidation sites. A series of pyrazine-based diamino crosslinkers (Scheme 1 of this Example 4, Cross linkers 1-3) were designed for exploring the potential factors during the reaction with pyrazine acting as a monitoring probe. Furthermore, the photophysical properties of these crosslinked nanostructures were also investigated to explore their potential application for optical imaging and monitoring.

Scheme 1 of Example 4: Chemical structures of pyrazine-based diamino crosslinkers. Structure 2 is also referred to as MP-3142. Structure 3 is also referred to as MP-3192.

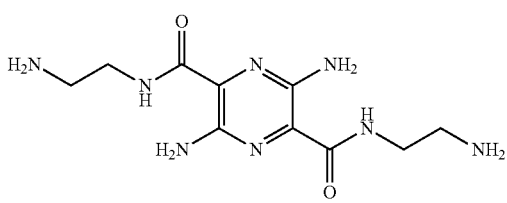

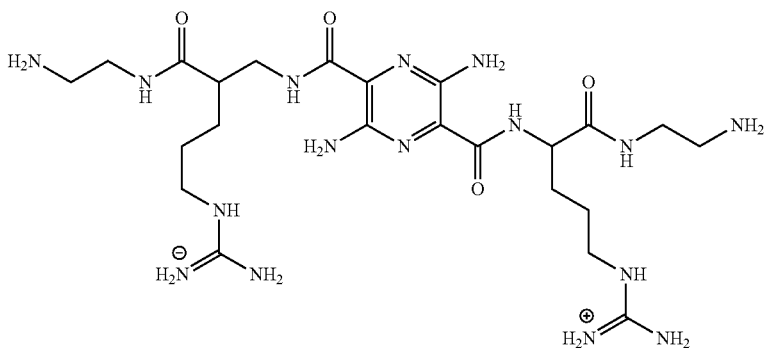

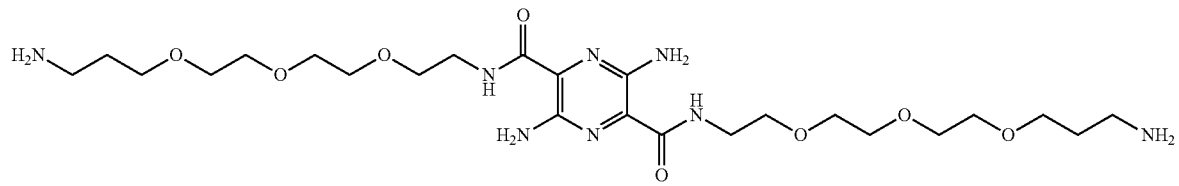

Results and Discussion

As depicted in Scheme 2 of this Example 4, well-defined diblock copolymers PEO$_{45}$-b-PNAS$_{95}$ and PEO$_{45}$-b-PNAS$_{105}$ were obtained via reversible addition-fragmentation chain transfer (RAFT) polymerization, starting from a PEO$_{45}$ based macro chain transfer agent (macro-CTA). GPC analyses of these two polymers (Scheme 2 of Example 4, insertions) clearly demonstrated their monomodal molecular weight distributions, even at higher NAS monomer conversions (90% and 95% respectively). Further chain extension with styrene yielded triblock copolymers PEO$_{45}$-b-PNAS$_{95}$-b-PS$_{60}$ (compound 4) and PEO$_{45}$-b-PNAS$_{105}$-b-PS$_{50}$ (compound 5).

Figure 8:
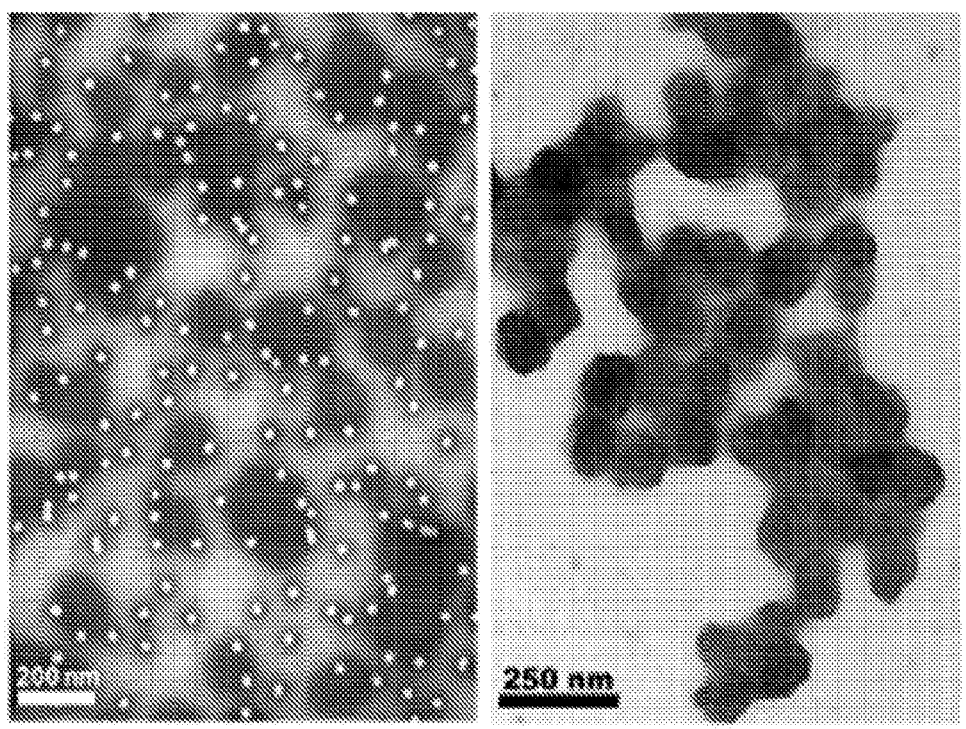
FIG. 8 provides TEM images of micelles generated from compounds 4 of Example 4 and multicompartment micelles generated from compound 5 of Example 4.
Figure 9:
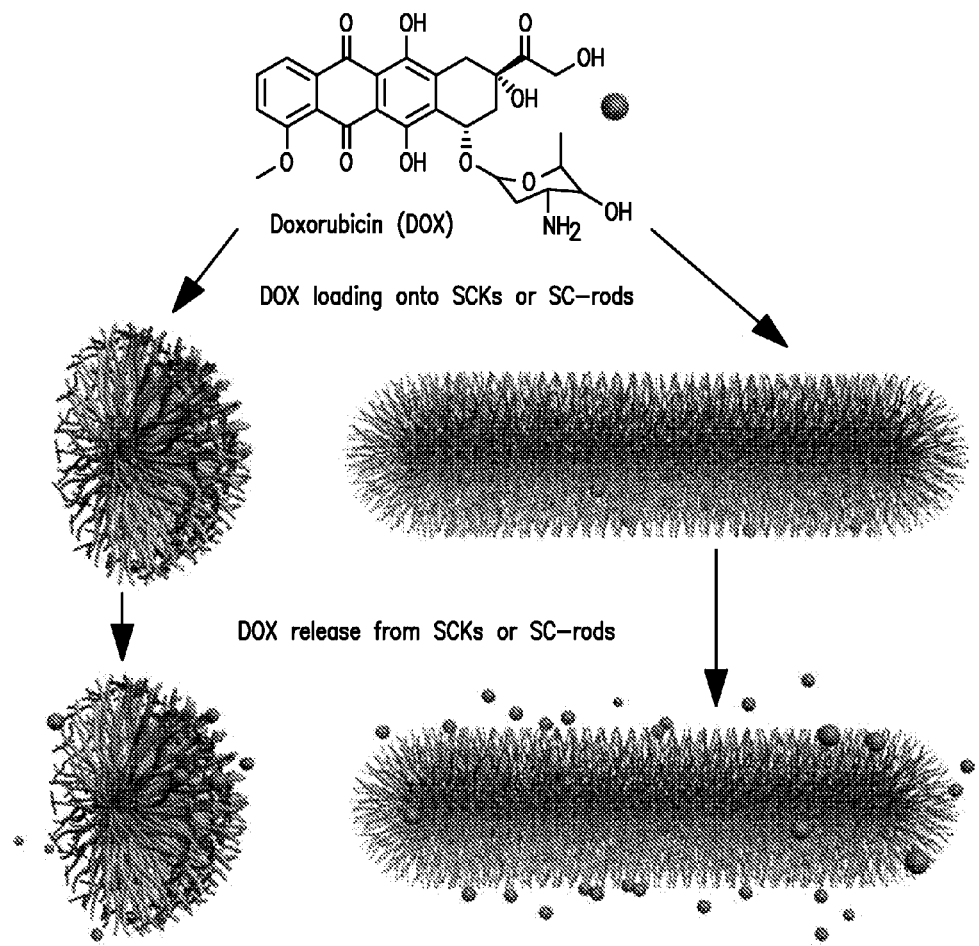
FIG. 9 shows a general description of loading and release of therapeutic payload using spherical or rod-shaped nanostructures.
Figure 10:
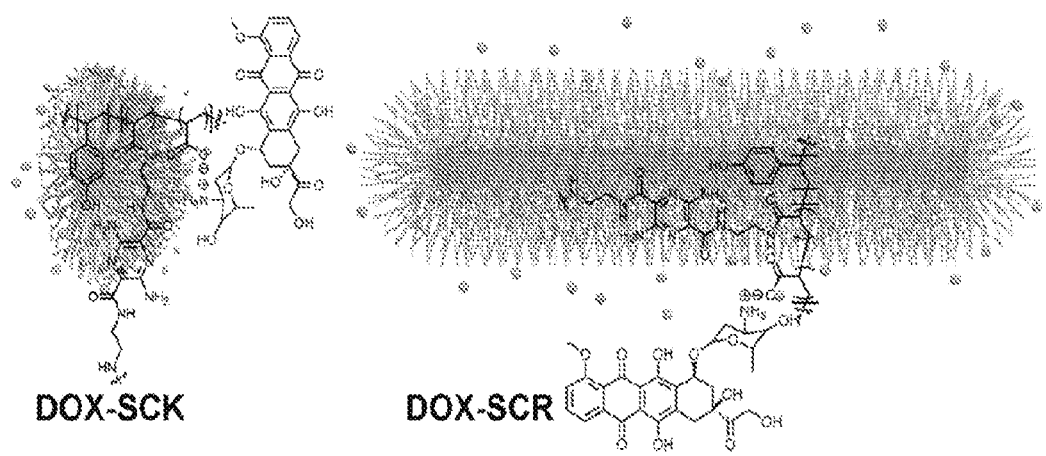
FIG. 10 shows a schematic representation of DOX-loaded shell-crosslinked spherical (DOX-SCK) or rod-shaped (DOX-SCR) nano-objects.

A typical self assembly protocol was employed consisting of addition of water, a selective solvent for PEO, to the polymer precursor solution in DMF, a common solvent for all blocks. Interestingly, compound 4 provided micelles with hydrodynamic diameter of ca. 50 nm, while multicompartment micelles with hydrodynamic diameter of ca. 300 nm were generated from the assembly of compound 5 (See, FIG. 8). FIG. 8 provides TEM images of micelles (left) generated from compounds 4 of Example 4 and multicompartment micelles (right) generated from compound 5 of Example 4.

The crosslinking/functionalization efficiency for cross linkers 1 and 2 was almost identical, although the hydrophilicity of cross linker 2 was increased. A maximum of 30%

Scheme 2 of Example 4. Preparation of amphiphilic triblock copolymers.
Insertions are DMF SEC profiles for the diblock (top) and triblock (bottom) copolymers.

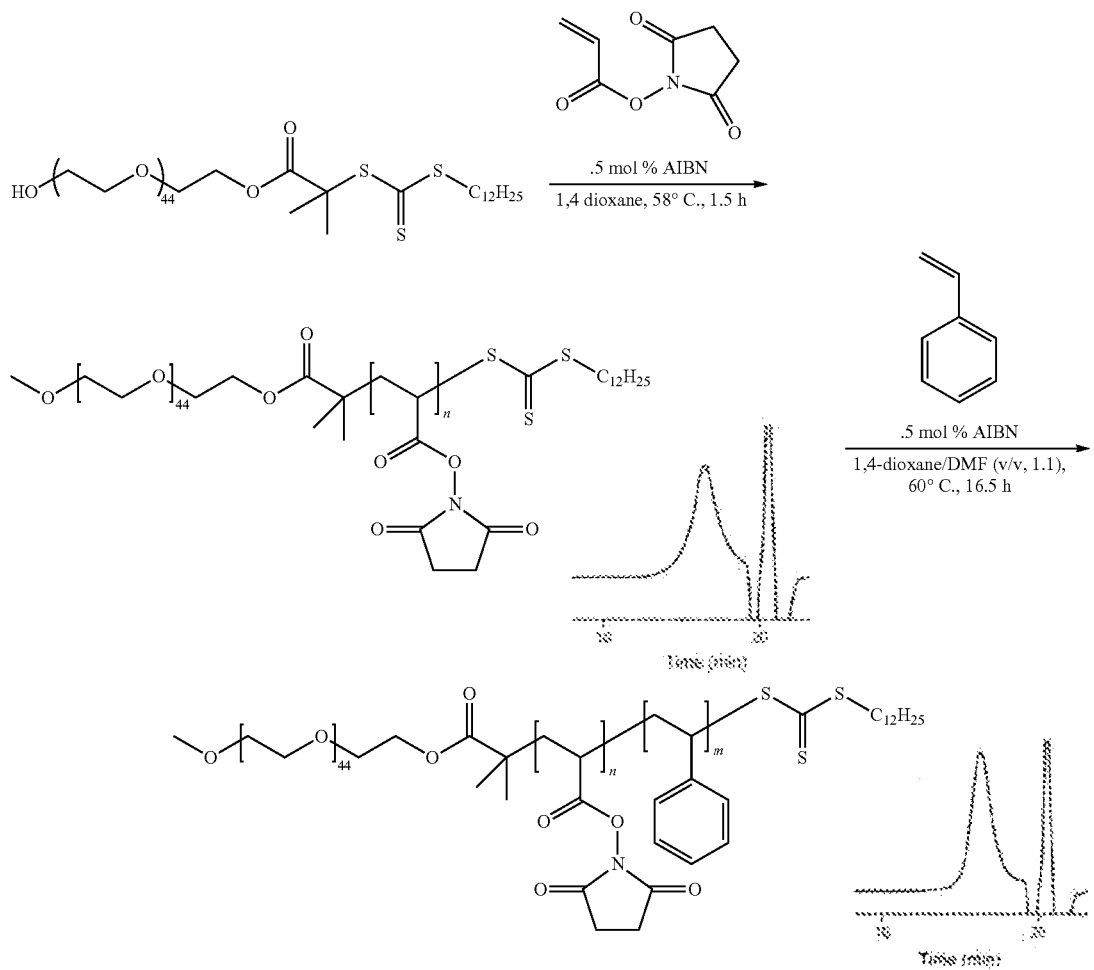

actual crosslinking extent was achieved at each nominal extent (20%, 50%, and 100%, respectively). Dramatic improvement to a maximum of 60% actual crosslinking extent at each nominal extent was achieved while using cross linker 3, a crosslinker bearing positive charge. This improvement could be attributed to strong electrostatic interactions between the guanidine moieties of the bifunctional bis-arginyl-pyrazine 3, and copolymer NAS-derived carboxylates, generated by partial hydrolysis of active esters during the micellization process. The present invention includes the use of a variety of cross linking moieties having one or more natural or non-natural amino acid groups, particularly one or more basic amino acids, such as arginine, lysine, histidine, ornithine, and homoarginine. Thus, pre-coordination of cross linker 3 with the micelles/multicompartment micelle via guanidine-carboxylate complexes, resulted in a vast enhancement of inter-strand amide crosslinking reaction efficiency. The morphology of all of these nanoobjects was maintained for micelles and multicompartment micelles after crosslinking at the nominal 20% and 50% extents, while different morphologies were observed for crosslinked micelles at the nominal 100% extents.

Photophysical properties of these photonic nanoparticles and multicompartment micelles were then measured. For cross linkers 1 and 2, only the nominal 100% crosslinked nanoparticles exhibited similar UV-Vis profiles as the crosslinkers themselves while a blue shift (ca. 35 nm) was observed for the nominal 20% crosslinked micelles. For cross linker 3, blue shift (ca. 40 nm) was also observed for nominal 20% crosslinked micelles, but the nominal 50% crosslinked nanoparticles already displayed identical maximum UV-Vis absorption at 440 nm as the crosslinker. All of these nanoobjects showed pH-sensitive fluorescence enhancements up to 300% in the range of pH 5.5 to 8.5. There were no obvious hydrodynamic diameter variations of these nanoparticles and multicompartment micelles in the surveyed pH range, as measured by DLS.

A novel amphiphilic triblock copolymer system having a functionalized PNAS segment was established. Further treatments of this functional polymer led to functionalized nanostructures bearing interesting stoichiometric and pH-sensitive photophysical properties. This method also allowed for the facile quantification of actual crosslinking extents.

This Example highlights the usefulness of controlled radical polymerization of functional monomers to provide well-defined, reactive block copolymers that can be transformed into functional nanoscale objects. Employing reversible addition-fragmentation chain transfer (RAFT) polymerization, well-defined amphiphilic triblock copolymers poly(ethylene oxide)-b-poly(N-acryloxysuccinimide)-b-polystyrene (PEO-b-PNAS-b-PS) were obtained. These polymer precursors were assembled into highly functionalizable nanoparticles and nano-scale multicompartment micelles in aqueous media. After in situ crosslinking with a series of pyrazine-based diamino crosslinkers through amidation, it was revealed that the reaction efficiency varied with the composition and properties of the crosslinkers. The photophysical properties of the pyrazine fluorophore (i.e. UV absorption and fluorescence) were also found to be altered after covalent incorporation into the polymer assemblies. These results not only provided direct "visualization" of the extent of crosslinking, but also demonstrated that the photonic crosslinked nanostructures could be utilized for optical imaging and monitoring.

EXAMPLE 5

Shell-Crosslinked Nanoparticles for Optical Imaging and Therapy with Incorporation and Release of Doxorubicin (DOX)

Figure 11:
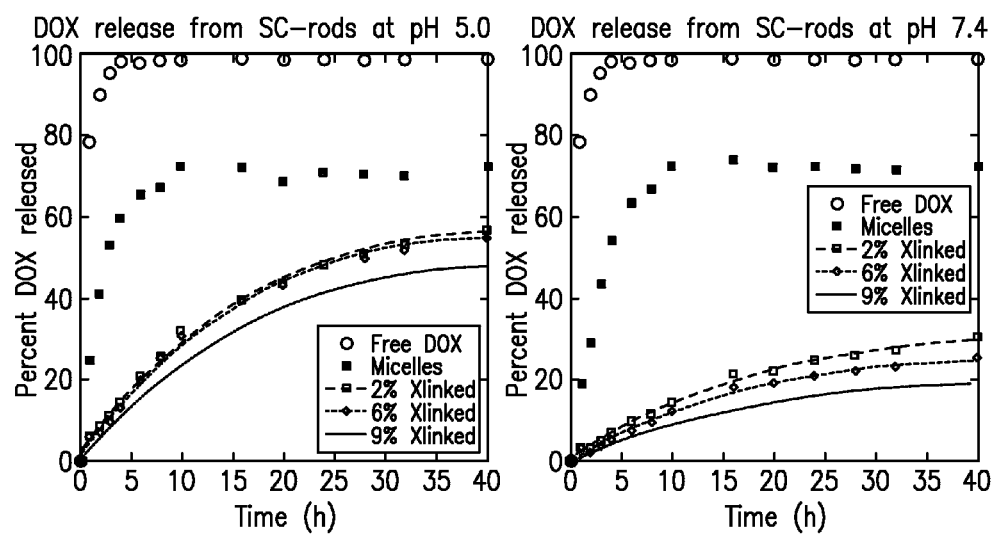
FIG. 11 shows one example of doxorubicin (DOX) release profile of a SC-rod with 2, 6 or 9% crosslink density at two different pH values.
Figure 12:
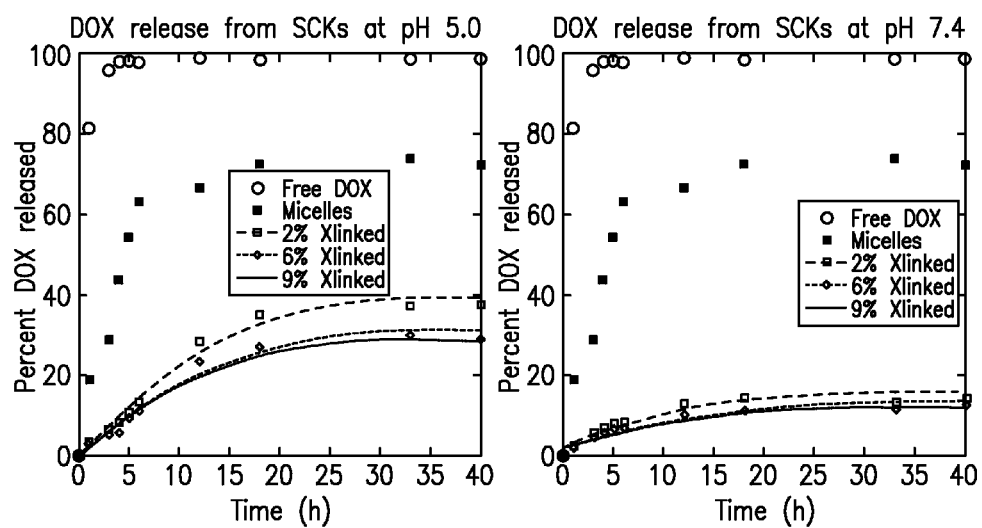
FIG. 12 shows one example of DOX release profile of a SCK with 2, 6 or 9% crosslink density at two different pH values.
Figure 13:
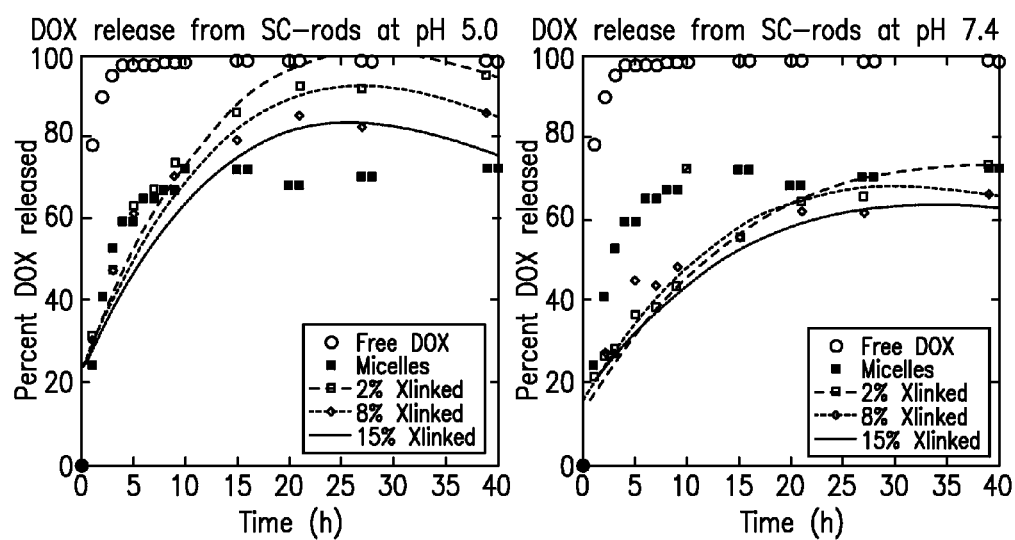
FIG. 13 shows DOX release profile of a SC-rod with 2, 8 or 15% crosslink density.

For the data shown in FIGS. 11 and 12, the following procedures were followed:

Formation of Spherical Micelles:

Into 55.2 mL of nanopure water with solution pH 12 was added 25.7 mg of $PAA_{140}$-b-$PpHS_{50}$ ($M_n$=16.4 kDa; $M_w/M_n$=1.14) and the solution was allowed to stir for 3 hrs. The solution pH was adjusted to ca. 6 by adding drops of hydrochloric acid and further allowed to stir overnight to achieve a final polymer concentration of ca. 0.3 mg/mL.

Formation of Rod-Shaped Nanostructures:

Into 85.5 mL of nanopure water with solution pH 6 was added 25.7 mg of $PAA_{140}$-b-$PpHS_{50}$ ($M_n$=16.4 kDa; $M_w/M_n$=1.14) and the solution was allowed to stir overnight.

Preparation of Shell-Crosslinked Nanoparticles (SCKs) or Rod-Shaped Nanostructures (SC-Rods):

To each of three vials was added 25 mL of spherical micelle or rod-shaped nanostructure solution with polymer concentration of ca. 0.3 mg/mL. To each vial was added different amounts of crosslinking chromophore, MP-3142 or MP-3192 (1.1, 5.5 or 11 molar equivalents) using an electronic pipette and allowed to stir for 2 hrs. To this reaction mixture was added dropwise, via a metering pump, a freshly prepared solution of 1-[3-(dimethylamino)propyl]-3-ethylcarbodiimide methiodide dissolved in nanopure water (2.8, 14 or 28 molar equivalents). The reaction mixtures were allowed to stir for 24 hrs at rt and were then transferred to presoaked dialysis membrane tubes (MWCO ca. 6-8 kDa), and dialyzed against 5 mM PBS for three days and nanopure water for one day to remove free crosslinking chromophores and urea by-products. The percentages of incorporation of crosslinking chromophores were determined by UV-vis spectroscopy.

General procedure for the preparation of DOX-loaded spherical SCKs or SC-rods: A solution of doxorubicin (0.9 mg/mL in dimethylformamide and 3 eq. of triethylamine, 30% w/w with respect to the SCK or SC-rod) was added to a vial containing a magnetic stir bar and the SCK or SC-rod solution (7 mL). The solution was protected from light and stirred overnight. The solution was then transferred to a centrifugal filter device (Amicon Ultra 4, 30 kDa MWCO, Millipore Corp., Billerica Mass., USA) and washed extensively with 5 mM PBS pH 7.4 buffer at 37° C. to remove all unincorporated DOX. After several washing cycles, the filtrate was analyzed by UV-vis (488 nm) to confirm the successful removal of the free DOX. The amount of incorporated DOX was determined by UV-vis (480 nm, E=13050 $M^{-1}$ $cm^{-1}$). In an example an approximately 36% wt % DOX loading in SC-rods using MP-3142 crosslinkers was provided. In an example, an approximately 17 wt % DOX loading for spherical SCKs using MP-3142 crosslinkers was provided. In an example, an approximately 12 wt % DOX loading in SC-rods using MP-3192 crosslinkers was provided.

General procedure for the DOX release experiments: To a presoaked dialysis cassette (Slide-A-Lyzer, 10 kDa MWCO, Pierce Biotechnology, Rockford Ill., USA) was added ca. 7 mL of the DOX-loaded SCK or SC-rod solution. The cassette was stirred in a beaker containing 4 L of 5 mM PBS at pH 5.0 or 7.4 and 37° C. for a period of 52 hrs. Samples (ca. 1 mL) were removed from the cassette at 0, 1, 2, 3, 5, 7, 9, 15, 21, 27, 39 and 52 h and analyzed by UV-vis spectroscopy (488 nm, $\epsilon$=13050 $M^{-1}$ $cm^{-1}$) and injected back to the cassette immediately after the analysis. DOX release data points were then fitted to a third order polynomial equation. The results are shown in FIGS. 10-13.

Figure 14:
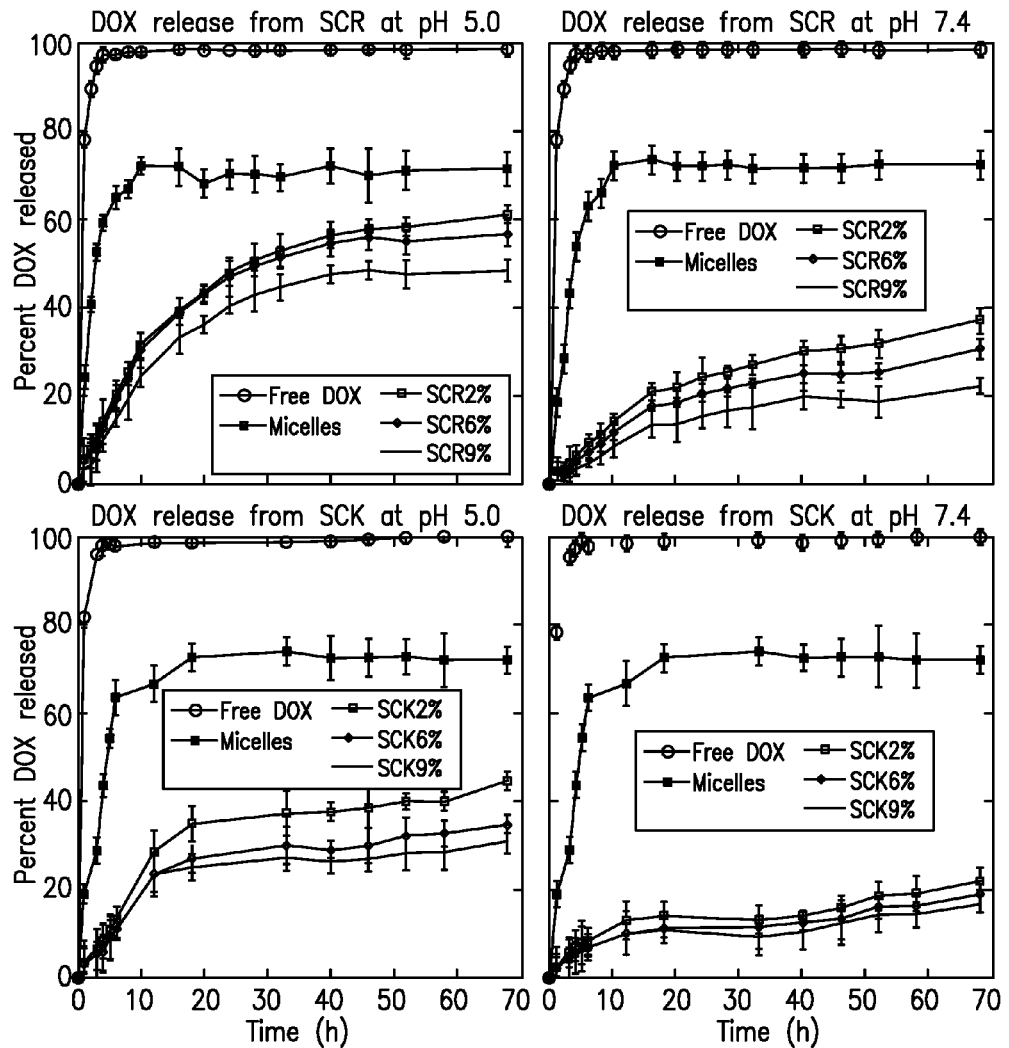
FIG. 14 shows DOX release from rod-shaped (SCR) SCR2%, SCR6% or SCR9% (top) and shell-crosslinked spherical (SCK) SCK2%, SCK6% or SCK9% (bottom) at pH 5.0 (left) or 7.4 (right) aqueous buffer solution where the percentages given are the % of cross-linking.

For the results shown in FIG. 14 the following procedures were followed.

Preparation of Rod-Shaped Micelles (1): To a 100-mL RB flask equipped with a magnetic stir bar was added $PAA_{140}$-b-$PpHS_{50}$ (93 mg, 5.7 μmol) and nanopure water (91 mL) to achieve a polymer concentration of ca. 1.0 mg/mL. The mixture was allowed to stir at rt for 2 h. An aliquot of the solution (25 mL) was added to a 100-mL RB flask and diluted with nanopure water (60 mL) to achieve a final polymer concentration of ca. 0.3 mg/mL. The solution was allowed to stir at rt overnight.

Preparation of Spherical Micelles (2): To a 100-mL RB flask equipped with a magnetic stir bar was added 50 mL of $PAA_{140}$-b-$PpHS_{50}$ (15 mg, 0.9 μmol). The pH value was adjusted to ca. 12 by adding a pellet of NaOH to afford a clear solution. The micellization was initiated by decreasing the solution pH value to ca. 7 by adding dropwise HCl. The micelle solution was allowed to stir at rt for 12 h. $H_{av}$=5±2 nm (AFM); $D_{av}$=16±3 nm (TEM); $P_h$ as measured by DLS was pH dependent—see ref[13] for the data.

Preparation of Shell-Crosslinked Rod-Shaped Nanostructures (SCR): To a 50-mL RB flask equipped with a magnetic stir bar was added a solution of 1 1n nanopure $H_2O$ (28 mL, 72 μmol of carboxylic acid residues). To this solution, was added a solution of 3,6-diamino-$N^2,N^5$-bis(2-aminoethyl)pyrazine-2,5-dicarboxamide (0.2 mg, 0.6 μmol (0.8 mol % relative to the acrylic acid residues) for 2% crosslinking extent; or 1.0 mg, 2.8 μmol (3.9 mol % relative to the acrylic acid residues) for 6% crosslinking extent; or 2.0 mg, 5.6 μmol (7.9 mol % relative to the acrylic acid residues) for 10% crosslinking extent). The reaction mixture was allowed to stir at rt for 2 h. To this solution was added, dropwise via a syringe pump over 1 h, a solution of 1-[3'-(dimethylamino)propyl]-3-ethylcarbodiimide methiodide (EDCI, 0.4 mg, 1 μmol for 2% crosslinking extent; or 2.1 mg, 7.2 μmol for 6% crosslinking extent; or 4.3 mg, 14 μmol for 9% crosslinking extent) and the reaction mixture was further stirred at rt for 16 h. Finally, the reaction mixture was transferred to pre-soaked dialysis tubing (MWCO ca. 3,500 Da) and dialyzed against nanopure water for 3 d to remove the non-attached crosslinker, excess small molecule starting materials and by-products, and afford aqueous solutions of shell-crosslinked cylinder, SCR2%, SCR6% or SCR9% (final polymer concentration: 0.35 mg/mL, 0.3 mg/mL, 0.28 mg/mL, respectively—where in each case, the % crosslinking was determined by UV-vis spectroscopic measurement of the amount of crosslinker remaining after purification). SCR2%, SCR6% and SCR9% measured 23±2 nm in width and 100 nm to a micron length, by TEM.

Preparation of Shell-Crosslinked Spherical Nanoparticles (SCK): To a 50-mL RB flask equipped with a magnetic stir bar was added a solution of 2 in nanopure $H_2O$ (25 mL, 68 μmol of carboxylic acid residues). To this solution, was added a solution of 3,6-diamino-$N^2,N^5$-bis(2-aminoethyl)pyrazine-2,5-dicarboxamide (0.2 mg, 0.5 μmol (0.8 mol % relative to the acrylic acid residues) for 2% crosslinking extent; or 1.0 mg, 2.7 μmol (3.9 mol % relative to the acrylic acid residues) for 6% crosslinking extent; or 2.0 mg, 5.4 μmol (7.9 mol % relative to the acrylic acid residues) for 9% crosslinking extent). The reaction mixture was allowed to stir at rt for 2 h. To this solution was added, dropwise via a syringe pump over 1 h, a solution of 1-[3'-(dimethylamino)propyl]-3-ethylcarbodiimide methiodide (EDCI, 0.4 mg, 1 μmol for 2% crosslinking extent; or 2.0 mg, 6.8 μmol for 6% crosslinking extent; or 4.1 mg, 14 μmol for 10% crosslinking extent) and the reaction mixture was further stirred at rt for 16 h. Finally, the reaction mixture was transferred to pre-soaked dialysis tubing (MWCO ca. 3,500 Da) and dialyzed against nanopure water for 3 d to remove the non-attached crosslinker, excess small molecule starting materials and by-products, and afford aqueous solutions of shell-crosslinked spherical nanoparticles, SCK2%, SCK6% or SCK9% (final polymer concentration: 0.25 mg/mL, 0.24 mg/mL, 0.24 mg/mL, respectively—where in each case, the % crosslinking was determined by UV-vis spectroscopic measurement of the amount of crosslinker remaining after purification). SCK2%, SCK6% and SCK9% measured 27±3 nm by number-average distribution dynamic light scattering measurements. SCK2%, SCK6% and SCK9% measured 23±2 nm in diameter, by TEM.

Loading DOX into SCRs: To a 20-mL scintillation vial equipped with a magnetic stir bar was added a solution of SCR2% (6.5 mL, 2.0 mg of polymer), SCR6% (7.2 mL, 2.1 mg of polymer) or SCR9% (8.9 mL, 2.5 mg of polymer). To this solution was added 50 wt % of doxorubicin (0.94 mg/mL in N,N-dimethylformamide and triethylamine) (for SCR2%: 1.1 mL, for SCR6%: 1.1 mL, for SCR9%: 1.3 mL). The scintillation vial containing the reaction mixture was covered with aluminum foil and allowed to stir at rt overnight. The solution was then transferred to a centrifugal filter device (Amicon Ultra 4, 30 kDa MWCO, Millipore Corp., Billerica Mass., USA) and washed extensively with 100 mM PBS pH 7.4 buffer at 37° C. to remove all unincorporated DOX. After several washing cycles, the filtrate was analyzed by UV-vis (488 nm) to confirm the successful removal of the free DOX.

Loading DOX into SCKs: To a 20-mL scintillation vial equipped with a magnetic stir bar was added a solution of SCK2% (8.0 mL, 2.0 mg of polymer), SCK6% (8.0 mL, 1.9 mg of polymer) or SCK9% (8.0 mL, 1.9 mg of polymer). To this solution was added 50 wt % of doxorubicin (0.94 mg/mL in N,N-dimethylformamide and triethylamine) (for SCK2%: 1.1 mL, for SCK6%: 1.0 mL, for SCK9%: 1.0 mL). The scintillation vial containing the reaction mixture was covered with aluminum foil and allowed to stir at rt overnight. The solution was then transferred to a centrifugal filter device (Amicon Ultra 4, 30 kDa MWCO, Millipore Corp., Billerica Mass., USA) and washed extensively with 100 mM PBS pH 7.4 buffer at 37° C. to remove all unincorporated DOX. After several washing cycles, the filtrate was analyzed by UV-vis (488 nm) to confirm the successful removal of the free DOX.

DOX Release Experiments: DOX-SCR or DOX-SCK (ca. 4 mL) was transferred to a presoaked dialysis cassette (Slide-A-Lyzer, 10 kDa MWCO, Pierce Biotechnology, Rockford Ill., USA). The cassette was then allowed to stir in a beaker containing 4 L of 5 mM PBS at pH 7.4 or pH 5.0 at 37° C. for a period of 68 h in the dark. Samples (ca. 1.5 mL) were removed from the cassette at 0, 1, 2, 4, 6, 9, 12, 18, 24, 30, 40, 50 and 60 h, analyzed by UV-vis (488 nm, $\epsilon$=12500 $M^{-1}cm^{-1}$ determined by a calibration curve in PBS), and then returned to the cassette. All release experiments were conducted in triplicate.

Results of DOX Loading and Release

Figure 25A:
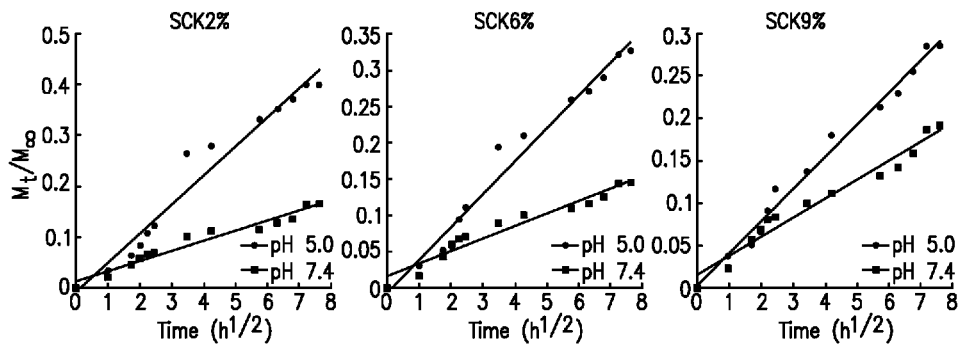
FIGS. 25A-C show Higuchi plots of DOX release profiles of SCK2%, SCK6% and SCK9% at pH 5.0 or pH 7.4 aqueous buffer solutions (FIG. 25A); SCR2%, SCR6% and SCR9% at pH 5.0 or pH 7.4 aqueous buffer solutions (FIG. 25B); and rSCR2%, rSCR6% and rSCR9% at pH 5.0 or pH 7.4 aqueous buffer solutions (FIG. 25C).
Figure 25B:
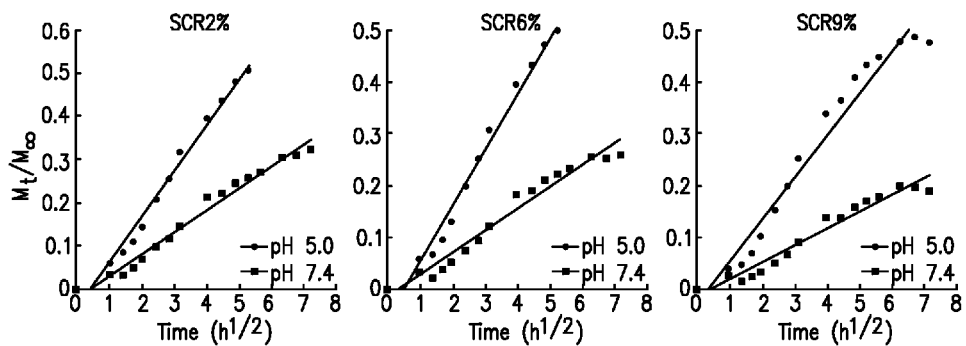
Figure 25C:
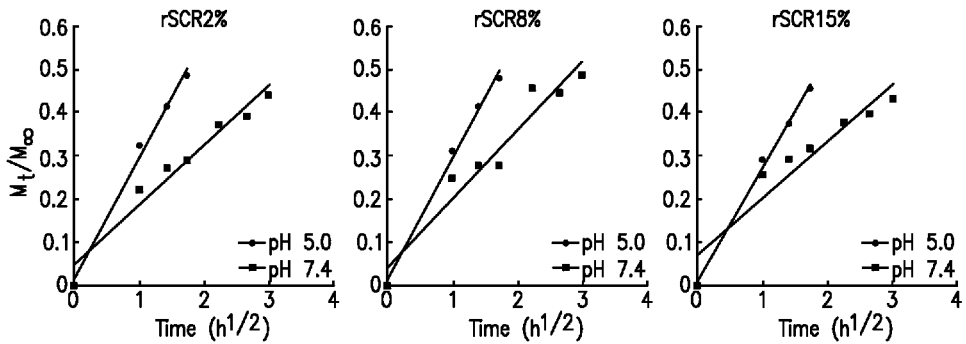

DOX-loaded rod-shaped (DOX-SCR) and spherical shell-crosslinked (DOX-SCK) nanostructures (FIG. 10) showed significant differences in guest loading and release behaviors. DOX-SCRs was capable of ca. 36 wt % drug loading, whereas ca. 17 wt % loading was observed for the DOX-SCK samples, as measured by UV-vis spectroscopy. The apparent differences in loading capacities of SCR vs. SCK may be due to the increased block copolymer chain densities uniquely present in the middle section of the rods or to the higher core volume within the rods, or a combination of both effects. Three samples of each of DOX-SCKs and DOX-SCRs varying in the crosslinking densities (2%, 6% or 9%) were used to conduct release experiments from dialysis cassettes against 5 mM PBS (pH 5.0 or 7.4) at 37° C. over a 68 h period. A control solution of free DOX reached a 95% release in 3 h and a complete release within 4 h, from the dialysis cassette at either pH value. Uncrosslinked micelle analogues exhibited a burst release of over 70% of the encapsulated drug molecules within 10 h at either pH value. Shell-crosslinked counterparts, however, gave controlled release of the guest molecules, whose rate was governed most significantly by solution pH, but also by the nanostructure morphology and crosslink density (FIG. 14) Observed differences in the release profiles from DOX-SCRs or DOX-SCKs at two solution pH values were attributed to the relative ionic attractions between protonated DOX molecules and deprotonated or protonated PAA residues. At solution pH 5.0, higher amounts of the PAA units became protonated than at pH 7.4 and, thereby, lost ionic interactions with protonated DOX molecules. This phenomenon was observed for both morphologies.

release time was approximately linear for the first 50% of drug release, in agreement with the limitations of the Higuchi model. The rate constants, k, calculated from the Higuchi plots, indicated faster kinetics for the drug release at pH 5.0 compared with pH 7.4, for all SCRs and SCKs, and faster release kinetics for the drug released from SCRs compared with SCKs, with subtle differences in rate among varying crosslink densities (Table 1). Higuchi plots of DOX release profiles of SCK2%, SCK6% and SCK9% at pH 5.0 or pH 7.4 aqueous buffer solutions are shown in FIG. 25A. Higuchi plots of DOX release profiles of SCR2%, SCR6% and SCR9% at pH 5.0 or pH 7.4 aqueous buffer solutions are shown in FIG. 25B. Higuchi plots of DOX release profiles of rSCR2%, rSCR6% and rSCR9% at pH 5.0 or pH 7.4 aqueous buffer solutions are shown in FIG. 25C.

TABLE 1

| | DOX release rate, k ($h^{-1/2}$), obtained from fitting drug release experimental data to the Higuchi model. | | | | | | |
|---|---|---|---|---|---|---|---|
| Solution pH | SCR2% | SCR6% | SCR9% | SCK2% | SCK6% | SCK9% | Micelle |
| pH 5.0 | 0.11 | 0.11 | 0.080 | 0.057 | 0.045 | 0.038 | 0.25 |
| pH 7.4 | 0.051 | 0.042 | 0.033 | 0.020 | 0.017 | 0.022 | 0.28 |

The observed higher capacity of DOX loading into SCRs and greater extent of release are curious and counterintuitive results. The SCRs appeared to be able to load more DOX under initial steady-state conditions of loading and yet, were also capable of greater release under the dynamic dialysis conditions. Therefore, studies were conducted to confirm that the overall dimensions and structures of the SCRs remained intact throughout the experiments, across the pH ranges employed. The SCRs remained as rod-shaped nanostructures at pH 4.7, pH 7.4 and 12.7. Only for the SCR having the lowest degree of crosslinking, subjected to pH 12.7, was destruction of the nanoassembly observed, due to deprotonation of both the PAA and PpHS blocks causing water-solubility (data not shown). At higher crosslink densities (i.e., SCR6% and SCR9%), maintenance of the overall rod-shape, held together by a sufficient amount of crosslinks, was observed by TEM. Therefore, the differences in the DOX loading and release, between the SCRs vs. SCKs, are explained as being due to differences in packing chain densities. The SCRs have heterogeneity along the backbone and the end-caps, which may provide for many sites to allow for DOX packaging, accommodating greater loading capacities. It was difficult to explain the greater extents of release. Understanding the subtle differences observed in release profiles from DOX-SCRs or DOX-SCKs of varying crosslinking densities required utilization of mathematical models.

Quantitative determination of the kinetics of DOX release was achieved through fitting the experimental data to an exponential relation for Fickian diffusion of a drug from a matrix of general shape, the Higuchi equation (M. R. Brophy, P. B. Deasy, *Int. J. Pharm.* 1987, 37, 41; T. Higuchi, *J. Pharm. Sci.* 1963, 52, 1145; L. Serra, J. Domenech, N. A. Peppas, *Biomaterials* 2006, 27, 5440)

$$\frac{M_t}{M_\infty} = kt^{\frac{1}{2}} \quad (1)$$

where $M_t/M_\infty$ is the proportion of drug released at a given time, k is the rate constant of drug release, and t is time. The proportion of DOX release plotted against the square root of To further quantitatively understand the differences and similarities in DOX release profiles, model-independent methods were used to calculate $f_1$, the difference factor, and $f_2$, the similarity factor (F. O. Costa, J. J. S. Sousa, A. Pais, S. J. Formosinho, *J. Controlled Release* 2003, 89, 199; J. W. Moore, H. H. Flanner, *Pharm. Tech.* 1996, 20, 67.):

$$f_1 = \frac{\sum_{t=1}^{n} |R_t - T_t|}{\sum_{t}^{n} R_t} \times 100 \quad (2)$$

where t is the sampling time, n is the number of time points, $R_t$ is the dissolution value of the reference (measured as the percentage of DOX release for the reference) and $T_t$ is the dissolution value of the sample of interest (measured as the percentage of DOX release from the sample). When the reference profile and the sample profile are identical, $f_1$ is equal to zero and, generally, the profiles are considered similar with $f_1$ values up to 15. The $f_2$ factor is a logarithmic transformation of the sum of squared error of difference between the reference and the sample of interest:

$$f_2 = 50 \times \log\left\{\left[1 + \frac{1}{n}\sum_{t=1}^{n}(R_t - T_t)^2\right]^{-0.5}\right\} \times 100 \quad (3)$$

When the reference profile and the sample profile are identical, $f_2$ is equal to 100; the profiles generally are considered similar when $f_2$ values are greater than 50. Both the difference factor $f_1$ and the similarity factor $f_2$ revealed that the SCR and SCK release profiles were significantly different from the release profiles of free DOX, micelles and each other at a comparable crosslink density (where all $f_1$ factors were greater than 15 and all $f_2$ factors were less than 50) at pH 5.0 or 7.4. Statistical differences were validated for different amounts of crosslinks except: SCR2% vs. SCR6% release profiles were similar at pH 5.0 ($f_1$=4, $f_2$=84); SCK6% vs. SCK9% release profiles were similar at pH 5.0 and 7.4 ($f_1$=9, $f_2=81$; $f_1=10$, $f_2=89$); SCK2% vs. SCK6% release profiles were similar at pH 7.4 ($f_1=15$, $f_2=83$). Overall, significantly different release profiles were observed only if there was a sufficient difference between the crosslinking densities (i.e., 2% vs. 9%), for which higher crosslinking densities slowed the drug release.

The hypothesis that ionic attractions played a partial role in gating of guest molecules was further evidenced by utilization of an arginine-functionalized chromophoric crosslinker. SCRs functionalized with positively-charged arginine-based crosslinkers (rSCRs) demonstrated promoted release of DOX due to ionic repulsions (data not shown). The initial introduction of the arginine-functionalized pyrazine crosslinkers at a low level (rSCR2%) gave the most significant extent of promoted release, and release profiles that approached those of free DOX escape from the dialysis cassette. As increasing amounts of the arginine-based crosslinker were incorporated (rSCR8% and rSCR15%), the crosslink gating effect was again observed as slight reductions in the rates of release, being more similar to those observed for release from the uncrosslinked micelles.

EXAMPLE 6

Paclitaxel Loaded Nanoparticles

The shell-crosslinked nanoparticles were used as a delivery and imaging vehicle for paclitaxel. These studies are described in this Example. Various loading capacities of paclitaxel and their cell killing abilities into 60 nm nanoparticles were investigated, as well as the effect of size of paclitaxel loaded 10 nm vs. 20 nm nanoparticles. The effect of paclitaxel loaded PEGylated vs. non-PEGylated 20 nm nanoparticles (high crosslinking density ~20%-30%) was studied. Also, investigation of MP3397 loaded PEGylated vs. non-PEGylated 20 nm nanoparticles (high crosslinking density ~20%-30%) was performed, as well as investigation of paclitaxel loaded PEGylated vs. non-PEGylated 20 nm nanoparticles (low crosslinking density ~5%-10%).

Figure 15:
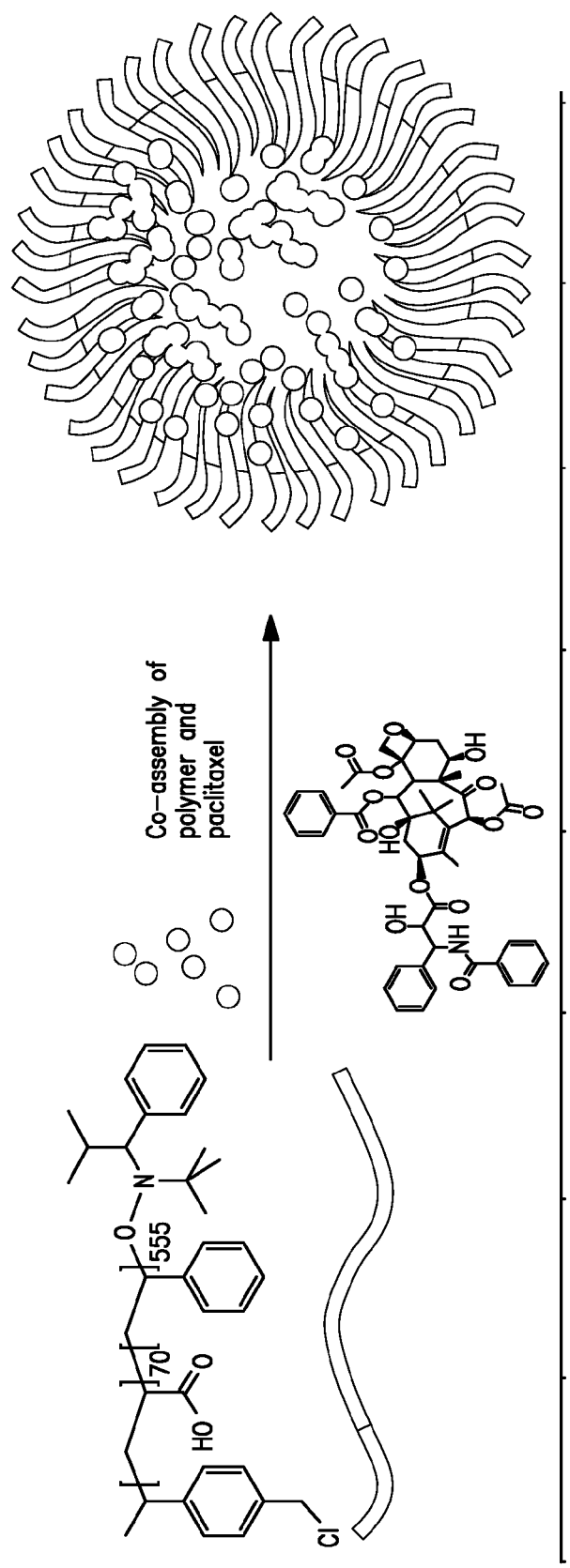
FIG. 15 shows a schematic diagram of the co-assembly of polymer and paclitaxel.

FIG. 15 shows a schematic diagram of the co-assembly of polymer and paclitaxel. Additional details for preparation of polymer and loading of the therapeutic agent are described below and elsewhere herein.

Table 2 provides details of polymer concentration and paclitaxel concentration in the example particles prepared. In Table 2, the abbreviation SCK represents shell crosslinked nanoparticles where MP-3142 is used for crosslinking as described elsewhere herein.

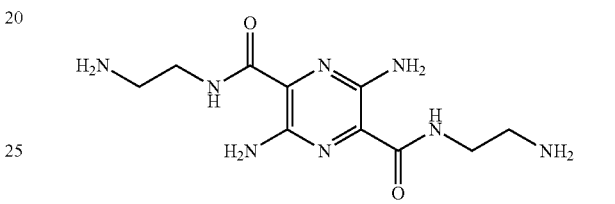

MP-3142

TABLE 2

Various loading capacities of paclitaxel (PTX) into 60 nm nanoparticles.

| | Code | | | | | | | | | |
|---|---|---|---|---|---|---|---|---|---|---|
| | YLL-ii-094a | YLL-ii-094b | YLL-ii-094c | YLL-ii-094d | YLL-ii-094e | YLL-ii-094f | YLL-ii-094g | YLL-ii-094h | YLL-ii-094i | YLL-ii-094j |
| Sample info | $PAA_{70}$-$b$-$PS_{555}$ micelle | $PAA_{70}$-$b$-$PS_{555}$ SCK | PTX--micelle-20 (20 wt %) | PTX-SCK-20 (20 wt %) | PTX-micelle-15 (15 wt %) | PTX-SCK-15 (15 wt %) | PTX-micelle-10 (10 wt %) | PTX-SCK-10 (10 wt %) | PTX-micelle-5 (5 wt %) | PTX-SCK-5 (5 wt %) |
| Polymer conc. [mg/mL] | 0.2667 | 0.2667 | 0.2326 | 0.2326 | 0.2469 | 0.2469 | 0.2532 | 0.2532 | 0.2597 | 0.2597 |
| Paclitaxel conc. [mg/mL] | — | — | 0.0465 | 0.0465 | 0.0370 | 0.0370 | 0.0253 | 0.0253 | 0.0123 | 0.0123 |

Figure 16:
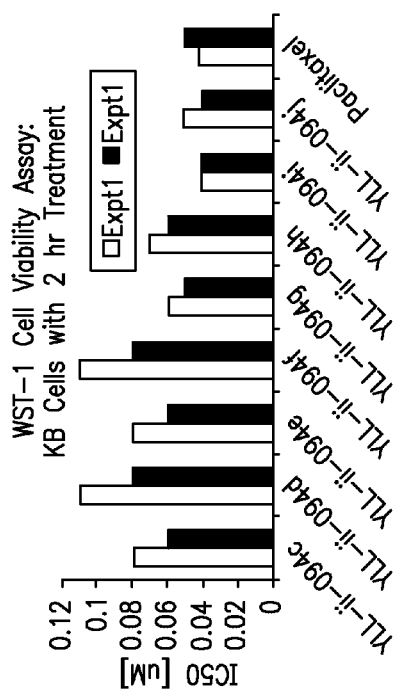
FIG. 16 shows the IC50 results for duplicate experiments for various compositions with KB cells with 2 hours of treatment.

Table 3 provides 1050 data for the EST-1 cell viability assay using KB cells with 2 hour treatment with the particles described above. FIG. 16 shows the 1050 results for duplicate experiments using several polymer samples. The results indicated that 5 wt % paclitaxel loaded SCKs showed the highest cell killing effect. The cell kill results for 5 wt % paclitaxel loaded SCKs was comparable to free paclitaxel. HPLC and MS analyses were in agreement with the determination of PTX concentration.

TABLE 3

Cell cytotoxicity assay results for 60 nm particles.

| Code | Sample info | PTX 2 hr $IC_{50}$ [uM] | PTX 72 hr $IC_{50}$ [uM] | PTX Conc. (mg/ml) | HPLC C18 PTX Amt. (ug/ml) | MMR LC/MS/MS PTX Amt. (ug/ml) |
|---|---|---|---|---|---|---|
| YLL-ii-094a | $PAA_{70}$-$b$-$PS_{555}$ micelle | NA | NA | 0 | ND | BMDL |
| YLL-ii-094b | $PAA_{70}$-$b$-$PS_{555}$ SCK | NA | NA | 0 | ND | BMDL |

TABLE 3-continued

Cell cytotoxicity assay results for 60 nm particles.

| Code | Sample info | PTX 2 hr IC$_{50}$ [uM] | PTX 72 hr IC$_{50}$ [uM] | PTX Conc. (mg/ml) | HPLC C18 PTX Amt. (ug/ml) | MMR LC/MS/MS PTX Amt. (ug/ml) |
|---|---|---|---|---|---|---|
| YLL-ii-094c | PTX-micelle-20 (20 wt %) | 0.08 | 0.017 | 0.0465 | 32.4 | 30.8 & 30.7 |
| YLL-ii-094d | PTX-SCK-20 (20 wt %) | 0.11 | 0.038 | 0.0465 | 21.7 | 38.7 & 38.9 |
| YLL-ii-094e | PTX-micelle-15 (15 wt %) | 0.08 | 0.015 | 0.0370 | 23.5 | 26.7 & 26.9 |
| YLL-ii-094f | PTX-SCK-15 (15 wt %) | 0.11 | 0.021 | 0.0370 | 19.5 | 16.2 & 16.4 |
| YLL-ii-094g | PTX-micelle-10 (10 wt %) | 0.06 | 0.012 | 0.0253 | 18.4 | 21.9 & 21.9 |
| YLL-ii-094h | PTX-SCK-10 (10 wt %) | 0.07 | 0.014 | 0.0253 | 8.4 | NA |
| YLL-ii-094i | PTX-micelle-5 (5 wt %) | 0.04 | 0.008 | 0.0123 | 9.5 | 9.1 & 9.2 |
| YLL-ii-094j | PTX-SCK-5 (5 wt %) | 0.05 | 0.009 | 0.0123 | 7.6 | 8.4 & 8.5 |
| Paclitaxel | in DMSO | 0.05 | 0.007 | | | |

The difference between 10 nm and 20 nm diameter particles on cell cytoxicity is described next. 10 nm particles of PAA$_{120}$-b-PS$_{40}$ had a diameter of 10±2 nm measured via TEM. 20 nm particles of PAA$_{120}$-b-PS$_{100}$ had a diameter of 20±3 nm measured via TEM. MP-3142 was used for crosslinking to provide shell crosslinked nanoparticles (SCKs).

Figure 17:
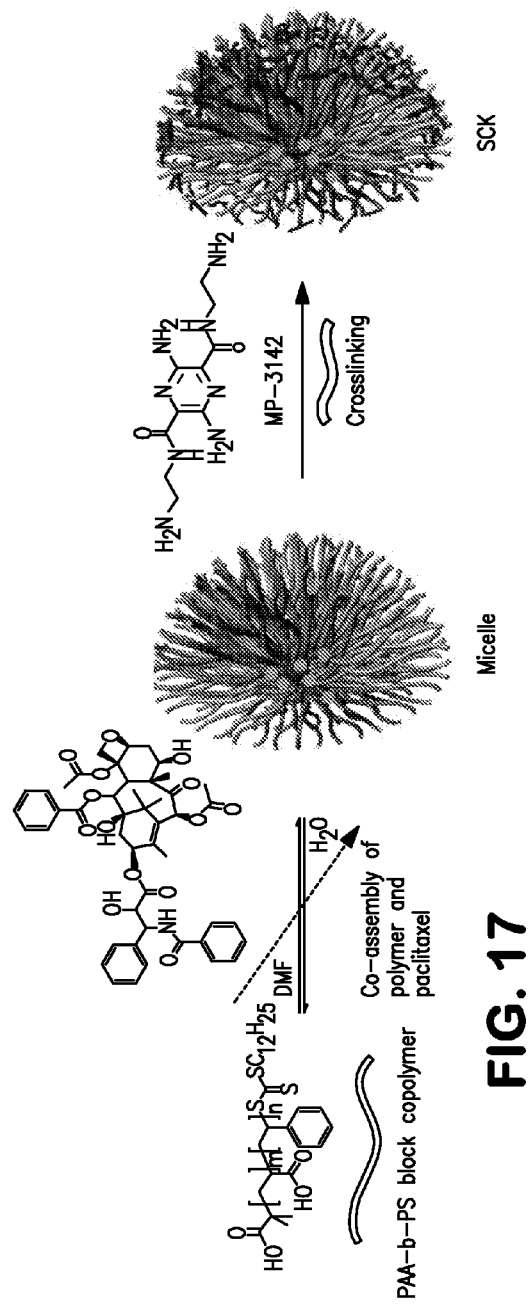
FIG. 17 provides a schematic diagram of co-assembly of polymer and paclitaxel to form a micelle, followed by crosslinking with MP-3142 to provide shell crosslinked nanoparticles (SCK).

FIG. 17 provides a schematic diagram of co-assembly of polymer and paclitaxel to form a micelle, followed by crosslinking with MP-3142 to provide shell crosslinked nanoparticles (SCK). Specific synthesis procedures are easily determined by one of ordinary skill in the art using the methods described below and herein.

Table 4 provides the composition of the samples prepared.

TABLE 4

Non-PEGylated Samples (10 nm vs. 20 nm)

PAA$_{120}$-b-PS$_{40}$ micelle
PAA$_{120}$-b-PS$_{40}$ SCK
PAA$_{120}$-b-PS$_{40}$ micelle with 5% PTX
PAA$_{120}$-b-PS$_{40}$ SCK with 5% PTX
PAA$_{120}$-b-PS$_{40}$ micelle with 10% PTX
PAA$_{120}$-b-PS$_{40}$ SCK with 10% PTX
PAA$_{120}$-b-PS$_{40}$ SCK with 10% PTX and AF647
PAA$_{120}$-b-PS$_{100}$ micelle
PAA$_{120}$-b-PS$_{100}$ SCK
PAA$_{120}$-b-PS$_{100}$ micelle with 5% PTX
PAA$_{120}$-b-PS$_{100}$ SCK with 5% PTX
PAA$_{120}$-b-PS$_{100}$ micelle with 10% PTX
PAA$_{120}$-b-PS$_{100}$ SCK with 10% PTX
PAA$_{120}$-b-PS$_{100}$ SCK with 10% PTX and AF647

Table 5 provides results of cell cytotoxicity 1050 data for the EST-1 cell viability assay using KB cells with the particles described above. "ND" means not determined.

TABLE 5

| Sample ID | Polymer Precursor | Micelle/ SCK | Polymer conc. (mg/mL) | MP3142 conc. mM | PTX wt % | PTX conc. (mg/mL) | After one day of loading 2 hr IC50 in uM | After one day of loading 72 hr IC50 in uM | After two weeks of loading 2 hr IC50 in uM | After two weeks of loading 72 hr IC50 in uM |
|---|---|---|---|---|---|---|---|---|---|---|
| YLL-ii-114A | PAA$_{120}$-b-PS$_{40}$ | Micelle | 0.2828 | — | — | — | ND | ND | ND | ND |
| YLL-ii-114B | PAA$_{120}$-b-PS$_{100}$ | Micelle | 0.2696 | — | — | — | ND | ND | ND | ND |
| YLL-ii-114C | PAA$_{120}$-b-PS$_{40}$ | SCK | 0.2971 | 0.0933 | — | — | ND | ND | ND | ND |
| YLL-ii-114D | PAA$_{120}$-b-PS$_{100}$ | SCK | N/A | N/A | — | — | — | — | — | — |
| YLL-ii-114E | PAA$_{120}$-b-PS$_{40}$ | Micelle | 0.3108 | — | 5% | 0.01554 | 0.0575 | 0.011 | 0.033 | 0.011 |
| YLL-ii-114F | PAA$_{120}$-b-PS$_{100}$ | Micelle | 0.2692 | — | 5% | 0.01346 | 0.057 | 0.023 | 0.1 | 0.02 |
| YLL-ii-114G | PAA$_{120}$-b-PS$_{40}$ | SCK | 0.3133 | 0.0775 | 5% | 0.01554 | 0.099 | 0.033 | 0.115 | 0.018 |
| YLL-ii-114H | PAA$_{120}$-b-PS$_{100}$ | SCK | 0.2786 | 0.0799 | 5% | 0.01346 | 0.062 | 0.016 | 0.066 | 0.012 |
| YLL-ii-114I | PAA$_{120}$-b-PS$_{40}$ | Micelle | 0.2439 | — | 10% | 0.02439 | 0.342 | 0.082 | 0.39 | 0.075 |
| YLL-ii-114J | PAA$_{120}$-b-PS$_{100}$ | Micelle | 0.3000 | — | 10% | 0.03000 | 0.08 | 0.021 | 0.071 | 0.015 |

TABLE 5-continued

| Sample ID | Polymer Precursor | Micelle/ SCK | Polymer conc. (mg/mL) | MP3142 conc. mM | PTX wt % | PTX conc. (mg/mL) | After one day of loading 2 hr IC50 in uM | After one day of loading 72 hr IC50 in uM | After two weeks of loading 2 hr IC50 in uM | After two weeks of loading 72 hr IC50 in uM |
|---|---|---|---|---|---|---|---|---|---|---|
| YLL-ii-114K | $PAA_{120}$-b-$PS_{40}$ | SCK | 0.2712 | 0.0804 | 10% | 0.02439 | 2 | 0.24 | 0.83 | 0.3 |
| YLL-ii-114L | $PAA_{120}$-b-$PS_{100}$ | SCK | 0.2714 | 0.0676 | 10% | 0.03000 | 0.23 | 0.05 | 0.13 | 0.046 |
| YLL-ii-114M | $PAA_{120}$-b-$PS_{40}$ | SCK | 0.2712 | 0.0804 | 10% | 0.02439 | >28 uM | 0.64 | >28 uM | 0.67 |
| YLL-ii-114N | $PAA_{120}$-b-$PS_{100}$ | SCK | 0.2714 | 0.0676 | 10% | 0.03000 | 0.4 | 0.1 | 0.46 | 0.07 |
| Paclitaxel | Free | — | — | — | — | — | 0.045 | 0.002 | 0.045 | 0.002 |

Confocal microscopy protocol. 50,000 KB cells were plated in each well of 8 well chamber slide in folate free RPMI1640 supplemented with 100 units/mL aqueous penicillin G, 100 ug/mL streptomycin, and 10% fetal bovine serum at concentrations to allow 70% confluence overnight.

Figure 18A:
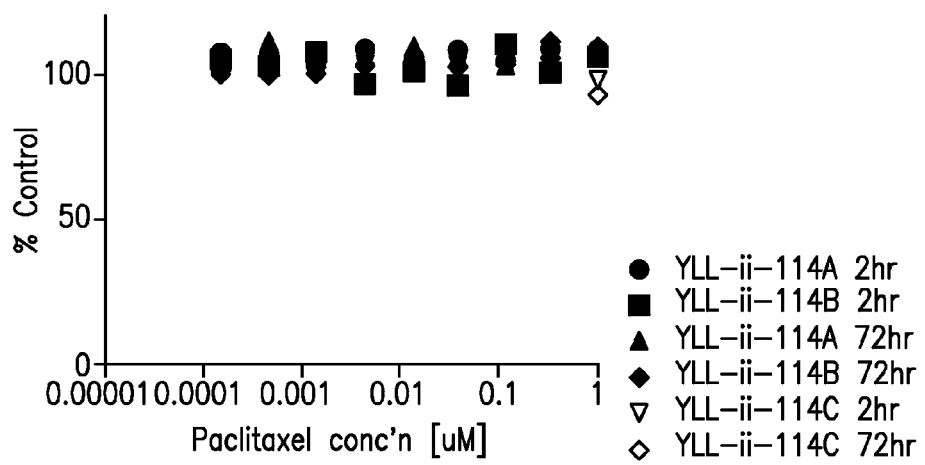
FIGS. 18A and 18B shows the paclitaxel concentration of various formulations as a function of time.
Figure 18B:
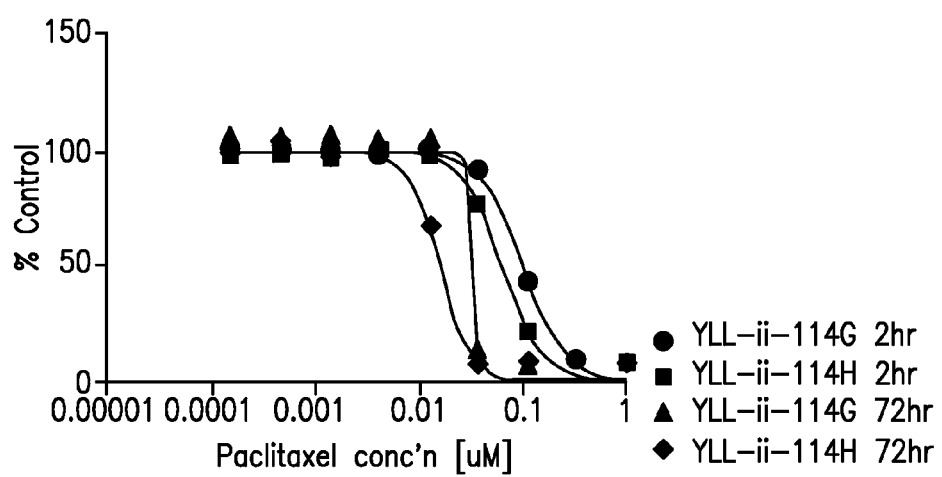

On the day of experiments, cells were washed with pre-warmed PBS. The cells were then incubated with empty or paclitaxel loaded SCKs diluted in folate free RPMI cell culture media. Cells were incubated for 2 hours to 3 hours at 37° C., washed with PBS three times, fixed with 4% formaldehyde, counterstained with Hoechst 33258 nuclear staining dye, and mounted with ProLong Antifade mounting medium. Cells were visualized with 60× objective and images were taken with Nikon A1 confocal microscope. FIGS. 18A and 18B show the paclitaxel concentration as a percent of control for various samples identified in Table 5.

It was suggested by fluorescence imaging that paclitaxel loaded SCKs are internalized by KB cells (data not shown). A 50 k MW CO spin filter experiment was performed which showed that the paclitaxel was encased in the SCKs and was not in the free solution, thus the cell killing was due to the nanoparticles.

The effect of PEGylated versus non-PEGylated particles on size, hydrodynamic diameter, and cell killing ability of particles is described next. In the general procedure to prepare the particles, a stock solution of paclitaxel/MP3397 dissolved in DMSO (1.199 mg/mL) was added to the polymer dissolved in DMF (1 mg/mL); Nanopure water was added dropwise (15 mL/h) to the solution of polymer and paclitaxel. The micelle solution was dialyzed against nanopure water to remove organic solvent. The micelle solutions were crosslinked with MP-3142 to afford shell crosslinked nanoparticles (SCKs). This is shown schematically in FIG. 17.

Table 6 provides the characteristics of particles prepared.

TABLE 6

| Sample ID | Sample Name | Polymer Precursor | Non-PEG/ PEG | Polymer conc. (mg/mL) | MP3142 conc. (mM) | Paclitaxel conc. (mg/mL) | MP3397 conc. (mg/mL) |
|---|---|---|---|---|---|---|---|
| YLL-ii-126A | SCK | $PAA_{120}$-b-$PS_{100}$ | Non-PEG | 0.2632 | 0.0562 | — | — |
| YLL-ii-126B | PEG-SCK | $P(AA_{0.95}$-$(PEG_{2k})_{0.05})_{120}$-b-$PS_{100}$ | PEG | 0.2837 | 0.0779 | — | — |
| YLL-ii-126C | SCK-PTX | $PAA_{120}$-b-$PS_{100}$ | Non-PEG | 0.2522 | 0.0438 | 0.0126 | — |
| YLL-ii-126D | PEG-SCK-PTX | $P(AA_{0.95}$-$(PEG_{2k})_{0.05})_{120}$-b-$PS_{100}$ | PEG | 0.2650 | 0.1248 | 0.0133 | — |
| YLL-ii-126E | SCK-MP3397 | $PAA_{120}$-b-$PS_{100}$ | Non-PEG | 0.2573 | 0.1274 | — | 0.0128 |
| YLL-ii-126F | PEG-SCK-MP3397 | $P(AA_{0.95}$-$(PEG_{2k})_{0.05})_{120}$-b-$PS_{100}$ | PEG | 0.2796 | 0.0893 | — | 0.0139 |

The paclitaxel loaded particles were shown to have a similar size as the corresponding particles having no drug loading, and the PEGylated particles exhibited a larger hydrodynamic diameter as measured by DLS. (data not shown). When viewed by TEM, PEGylated particles exhibited aggregation as compared to non-PEGylated particles.

Table 7 suggests that under the conditions studied, a higher crosslinking density resulted in lower cell killing ability of the SCKs as compared to SCKs with lower crosslinking density.

TABLE 7

| Sample ID | Sample Name | Diameter (nm) | Paclitaxel wt % | 2 h IC50 in μM | 72 h IC50 in μM | 2 h IC50 in μM | 72 h IC50 in μM |
|---|---|---|---|---|---|---|---|
| YLL-ii-126A | SCK | 21 ± 2 | 5% | ND | ND | ND | ND |

TABLE 7-continued

| Sample ID | Sample Name | Diameter (nm) | Paclitaxel wt % | 2 h IC50 in μM | 72 h IC50 in μM | 2 h IC50 in μM | 72 h IC50 in μM |
|---|---|---|---|---|---|---|---|
| YLL-ii-126B | PEG-SCK | 23 ± 3 | 5% | ND | ND | ND | ND |
| YLL-ii-126C | SCK-PTX | 23 ± 2 | 5% | 0.347 | 0.095 | 0.49 | 0.1 |
| YLL-ii-126D | PEG-SCK-PTX | 23 ± 3 | 5% | ND | 0.97 | ND | 0.97 |
| YLL-ii-114H | SCK-PTX | 20 | 5% | 0.062 | 0.016 | 0.066 | 0.012 |
| YLL-ii-114H | SCK-PTX | 20 | 5% | 0.078 | 0.015 | 0.1 | 0.017 |

Figure 19:
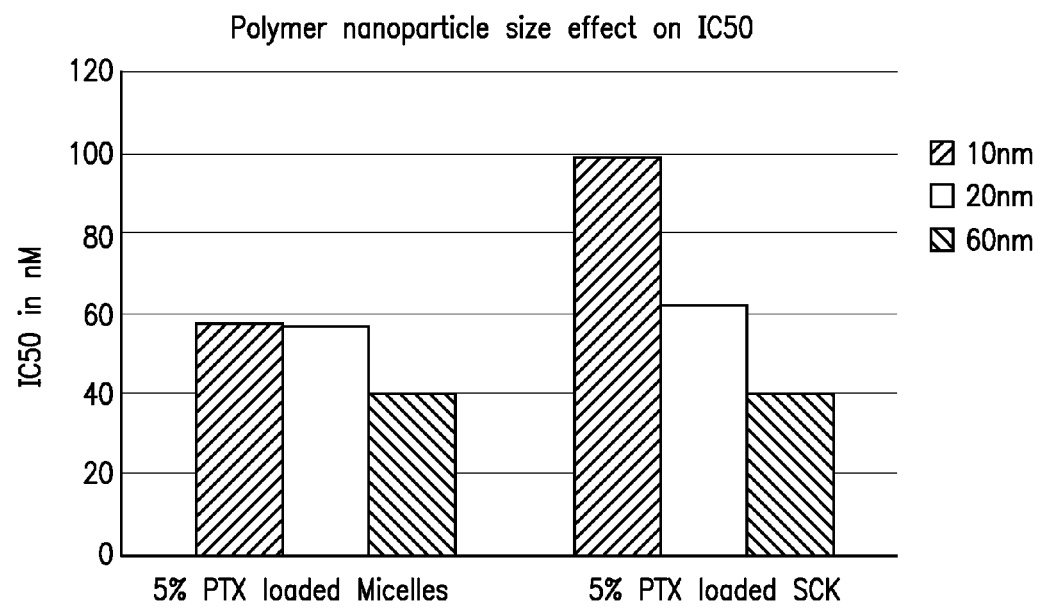
FIG. 19 shows the effect of polymer nanoparticle size on the IC50 for paclitaxel.

Different formulations were compared for the 1050. It appeared that a larger particle demonstrated a lower 1050 than a smaller particle, both for micelles and SCKs for the studies performed (see FIG. 19). For a given particle size, a higher crosslinked particle appears to exhibit a higher 1050 for paclitaxel for these studies.

Materials and Methods

Materials

All chemicals were purchased from Sigma Chemical Co. (St. Louis, Mo.) and used without further purification unless otherwise noted. The Supor 25 mm 0.1 μm Spectra/Por Membrane tubes (MWCO 6-8 kDa), used for dialysis, were purchased from Spectrum Medical Industries Inc. Nanopure water (18 MΩ·cm) was acquired by means of a Milli-Q water filtration system, Millipore Corp. (Bedford, Mass.). Polymer precursor $PAA_{120}$-b-$PS_{100}$ was synthesized as described elsewhere herein.

Instruments

Ultraviolet-visible spectroscopy (UV-vis) absorption measurements were made using a UV-2550 system (Shimadzu Corp., Japan) using PMMA cuvettes. Spectra were analyzed with UV-Probe v. 2.33 software. Dynamic light scattering measurements were conducted with a Brookhaven Instruments, Co. (Holtsville, N.Y.) DLS system equipped with a model BI-200SM goniometer, BI-9000AT digital correlator, and a model EMI-9865 photomultiplier, and a model Innova 300 Ar ion laser operated at 514.5 nm (Coherent Inc., Santa Clara, Calif.). Measurements were made at 25±1° C. Prior to analysis, solutions were filtered through a 0.45 μm Millex®-GV PVDF membrane filter (Millipore Corp., Medford, Mass.) to remove dust particles. Scattered light was collected at a fixed angle of 90°. The digital correlator was operated with 522 ratio spaced channels, and initial delay of 5 μs, a final delay of 50 ms, and a duration of 8 minutes. A photomultiplier aperture of 400 μm was used, and the incident laser intensity was adjusted to obtain a photon counting of between, 200 and 300 kcps. The calculations of the particle size distributions and distribution averages were performed with the ISDA software package (Brookhaven Instruments Company), which employed single-exponential fitting, Cumulants analysis, and CONTIN particle size distribution analysis routines. All determinations were average values from ten measurements. Transmission electron microscopy (TEM) bright-field imaging was conducted on a JOEL 1200 microscope, operating at 100 kV. The samples were prepared as follows: 4 μL of the dilute solution (with a polymer concentration of ca. 0.2-0.5 mg/mL) was deposited onto a carbon-coated copper grid, which was glow charged to increase the surface hydrophilicity. After 5 min, the excess of the solution was quickly wicked away by a piece of filter paper. The samples were then negatively stained with 4 μL of 1 wt % uranyl acetate aqueous solution. After 1 min, the excess PTA solution was quickly wicked away by a piece of filter paper and the samples were left to dry under ambient conditions overnight.

Preparation of Paclitaxel Loaded Nanoparticles

General procedure for co-assembly of paclitaxel and PAA-b-PS into micelles: PAA-b-PS (ca. 10 mg) polymers were dissolved in N,N-dimethylformamide (DMF) (10 mL) in a 100 mL round bottom flask and allowed to stir for 20 min at room temperature. Paclitaxel in dimethyl sulfoxide (DMSO) (1.144 mg/mL) was added to the solution and allowed to stir for additional 10 min at room temperature. To this solution, an equal volume of nanopure water was added dropwise via a syringe pump over a period of 1 h. The reaction mixture was allowed to stir for additional 24 h at room temperature and dialyzed against nanopure water for 3 days in a presoaked dialysis tubing (MWCO ca. 6-8 kDa) to afford a micelle solution with a final polymer concentration of ca. 0.25 mg/mL.

General procedure for shell crosslinking paclitaxel loaded micelles with MP-3142 to afford shell-crosslinked knedel-like nanoparticles (SCKs): To the micelle solution of paclitaxel loaded PAA-b-PS micelles was added a solution of MP-3142 in nanopure water (1.693 mg/mL, 1.1 eq., nominal 20% crosslinking) dropwise via a syringe pump over a period of 2 h. To this solution, 1-[3"-(dimethylamino)propyl]-3-ethyl-carbodiimide methiodide (EDCI) in nanopure water (3.467 mg/mL, 1.3 eq) was added dropwise via a syringe pump over 10 min and the resulting mixture was allowed to stir overnight before dialysis against nanopure water for 4 days in presoaked dialysis tubing (MWCO ca. 6-8 kDa) to afford SCK solutions with a final polymer concentration of ca. 0.25 mg/mL. The crosslinking density was measured by UV-vis spectroscopy to be about 7-10%.

EXAMPLE 7

Incorporation of Type I Phototherapeutic Agent-Loaded Nanoparticles

In embodiment, two photoactive moieties can be included into the nanoparticles. This allows for different monitoring or phototherapy functions in one particle, for example. In an embodiment of this aspect of the invention, one photoactive moiety can be used for crosslinking the block copolymers and another photoactive moiety can be used for phototherapy or optical monitoring applications, for example.

Materials and Methods
Preparation of MP-3397 Loaded Nanoparticles

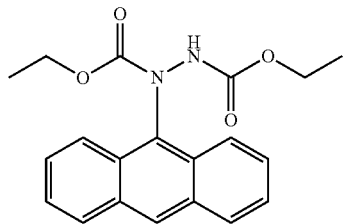

MP-3397

General procedure for loading of MP-3397 into PAA-b-PpHS micelles: To a 100-mL round bottom flask equipped a magnetic stir bar was charged with PAA-b-PpHS (ca. 27 mg) micelle solution. To this solution was added MP-3397 (0.66 mg, ca. 2.5 wt %) in N,N-dimethylformamide (DMF) (0.79 mg/mL). The mixture was allowed to stir overnight at room temperature before being dialyzed against nanopure water for 1 day in a presoaked dialysis tubing (MWCO ca. 6-8 kDa) to afford a micelle solution with a final polymer concentration of ca. 0.25 mg/mL.

General procedure for shell crosslinking MP-3397-loaded micelles with MP-3142 to afford shell-crosslinked knedel-like nanoparticles (SCKs): To the micelle solution of MP-3397-loaded PAA-b-PpHS micelles was added a solution of MP-3142 in nanopure water (1.693 mg/mL, 1.1 eq., nominal 20% crosslinking) dropwise via a syringe pump over a period of 2 h. To this solution, 1-[3"-(dimethylamino)propyl]-3-ethyl-carbodiimide methiodide (EDCI) in nanopure water (3.467 mg/mL, 1.3 eq) was added dropwise via a syringe pump over 10 min and the resulting mixture was allowed to stir overnight before dialysis against nanopure water for 4 days in presoaked dialysis tubing (MWCO ca. 6-8 kDa) to afford SCK solutions with a final polymer concentration of ca. 0.25 mg/mL. The crosslinking density was measured by UV-vis spectroscopy to be about 7-10%.

Materials. The universal alkoxyamine initiator 2,2,5-trimethyl-3-(1'-phenylethoxy)-4-phenyl-3-azahexane and the corresponding nitroxide 2,2,5-trimethyl-4-phenyl-3-azahexane-3-nitroxide were synthesized according to the literature method.[15] Boc-NH-PEG$_{3kDa}$-NH$_2$ and MeO-PEG$_{2kDa}$-NH$_2$ were purchased from Rapp Polymere (Tubingen, Germany). Ellman's reagent kit, 2,4,6,-trinitrobenzene sulfonic acid (TNBS), Zeba desalting columns, succinimidyl-([N-maleimidopropionamido]-ethyleneglycol) ester (NHS-PEO$_2$-maleimide) and N-succinimidyl-5-acetylthiopropionate (SATP) were purchased from Pierce Thermo Scientific (Waltham, Mass.). Sephadex-G25 medium was obtained from GE Healthcare. All other chemicals and reagents were obtained from Aldrich and used as received, unless described otherwise. tert-Butyl acrylate (tBA) and 4-acetoxystyrene were filtered through a plug of aluminum oxide to remove the inhibitor. The Supor 25 mm 0.1 µm Spectra/Por Membrane tubes (MWCO 6-8 kDa), used for dialysis, were purchased from Spectrum Medical Industries Inc. Nanopure water (18 MΩ·cm) was acquired by means of a Milli-Q water filtration system, Millipore Corp. (Bedford, Mass.). All reactions were performed under N$_2$, unless noted otherwise. Ellman's assay calibration curve was constructed using cysteine in aqueous buffer (100 mM PBS, 0.1 M NaCl, 10 mM EDTA, pH 7.4) at 412 nm.

Instrumental. $^1$H NMR and $^{13}$C NMR spectra were recorded at 500 MHz and 125 MHz, respectively, as solutions with the solvent proton or carbon signal as a standard. UV-Vis spectra were collected at ambient temperature in the region of 200-800 nm, using a Varian Cary 100 Bio UV-visible spectrophotometer. The fluorescence spectra were obtained at room temperature using a Varian Cary Eclipse fluorescence spectrophotometer. An excitation wavelength of the observed maximum absorption peak was used unless otherwise noted. Each fluorescence spectrum was normalized with respect to the absorbance at the excitation wavelength. The molar extinction coefficient ($\epsilon$) of chromophoric crosslinkers ($\epsilon$=5163 M$^{-1}$·cm$^{-1}$ at 441 nm) was determined by a calibration curve in 5 mM PBS. The chromophoric crosslinker concentrations in the nano-objects were determined by UV-vis spectroscopy.

Gel permeation chromatography (GPC) was conducted on a Waters 1515 HPLC (Waters Chromatography, Inc.) equipped with a Waters 2414 differential refractometer, a PD2020 dual-angle (15° and 90°) light scattering detector (Precision Detectors, Inc.), and a three-column series PL gel 5 µm Mixed C, 500 Å, and 10$^4$ Å, 300×7.5 mm columns (Polymer Laboratories, Inc.). The system was equilibrated at 35° C. in anhydrous THF, which served as the polymer solvent and eluent with a flow rate of 1.0 mL/min. Polymer solutions were prepared at a known concentration (ca. 4-5 mg/mL) and an injection volume of 200 µL was used. Data collection and analysis were performed, respectively, with Precision Acquire software and Discovery 32 software (Precision Detectors, Inc.). Interdetector delay volume and the light scattering detector calibration constant were determined by calibration using a nearly monodispersed polystyrene standard (Pressure Chemical Co., M$_p$=90 kDa, M$_w$/M$_n$<1.04). The differential refractometer was calibrated with standard polystyrene reference material (SRM 706 NIST), of known specific refractive index increment dn/dc (0.184 mL/g). The dn/dc values of the analyzed polymers were then determined from the differential refractometer response.

DLS measurements were also conducted using Delsa Nano C from Beckman Coulter, Inc. (Fullerton, Calif.) equipped with a laser diode operating at 658 nm. Size measurements were made in nanopure water. Scattered light was detected at 15° angle and analyzed using a log correlator over 70 accumulations for a 0.5 mL of sample in a glass size cell (0.9 mL capacity). The photomultiplier aperture and the attenuator were automatically adjusted to obtain a photon counting rate of ca. 10 kcps. The calculation of the particle size distribution and distribution averages was performed using CONTIN particle size distribution analysis routines using Delsa Nano 2.31 software. The peak average of histograms from intensity, volume and number distributions out of 70 accumulations were reported as the average diameter of the particles.

Transmission electron microscopy (TEM) bright-field imaging was conducted on a Hitachi H-7500 microscope, operating at 80 kV. The samples were prepared as follows: 4 µL of the dilute solution (with a polymer concentration of ca. 0.2-0.5 mg/mL) was deposited onto a carbon-coated copper grid, which was pre-treated with absolute ethanol to increase the surface hydrophilicity. After 5 min, the excess of the solution was quickly wicked away by a piece of filter paper. The samples were then negatively stained with 4 µL of 1 wt % phosphotungstic acid (PTA) aqueous solution. After 1 min, the excess PTA solution was quickly wicked away by a piece of filter paper and the samples were left to dry under ambient conditions overnight.

Synthesis of poly(acrylic acid)$_{140}$-g-(CONH-PEO$_{2kDa}$-OCH$_3$)-b-poly(p-hydroxystyrene)$_{50}$ (PAA$_{140}$-g-mPEO$_{2kDa}$-b-PpHS$_{50}$) (I). A flame-dried 100-mL round bottom flask equipped with a magnetic stir bar was charged with poly(acrylic acid)$_{140}$-b-poly(p-hydroxystyrene)$_{50}$ (325 mg, 19.9 µmol) and 50 mL of dry DMF. To the stirred solution, 1-hydroxybenzotrizole hydrate (HOBt) (91.2 mg, 0.675 mmol) and EDCI (201 mg, 0.675 mmol) were added and the reaction was left to proceed for 1 h, after which a solution of NH$_2$-mPEO$_{2kDa}$ (667 mg, 0.334 mmol, 16.8 equiv) dissolved in 5 mL of DMF and N,N-diisopropylethylamine (DIPEA) (87.2 mg, 0.675 mmol) were added. The reaction mixture was further stirred for 20 h at room temperature before being transferred to a presoaked dialysis tubing (MWCO ca. 6000-8000 Da), and dialyzed against nanopure H$_2$O for 2 days, to remove all of the impurities and afford PAA$_{140}$-g-mPEO$_{2kDa}$-b-PpHS$_{50}$ (I) as a white solid after lyophilization (913 mg, 92% yield). M$_n^{NMR}$=44,300 g/mol. $^1$H NMR (DMSO-d$_6$, ppm): δ 12.3 (br, 95 H), 8.94 (br, 78 H), 7.22 (m, 10 H), 6.45 (br, 200 H), 3.50-3.40 (br, 280 H), 2.40-2.18 (br, 45 H), 1.37 (m, 240 H).

Synthesis of poly(acrylic acid)$_{140}$-g-(CONH-PEO$_{3kDa}$-NH-Boc)-b-poly(p-hydroxystyrene)$_{50}$ (PAA$_{140}$-g-PEO$_{3kDa}$-NH-Boc-b-PpHS$_{50}$) (II). A flame-dried 100-mL round bottom flask equipped with a magnetic stir bar was charged with poly(acrylic acid)$_{140}$-b-poly(p-hydroxystyrene)$_{50}$ (379 mg, 23.2 µmol) and 50 mL of dry DMF. To the stirred solution, 1-hydroxybenzotrizole hydrate (HOBt) (91.0 mg, 0.672 mmol) and EDCI (200 mg, 0.672 mmol) were added and the reaction was left to proceed for 1 h, after which a solution of PEO$_{3kDa}$-NH-Boc (994 mg, 0.332 mmol, 14.3 equiv) dissolved in 5 mL of DMF and N,N-diisopropylethylamine (DIPEA) (86.8 mg, 0.672 mmol) were added. The reaction mixture was further stirred for 20 h at room temperature before being transferred to a presoaked dialysis tubing (MWCO ca. 6000-8000 Da), and dialyzed against nanopure H$_2$O for 2 days, to remove all of the impurities and afford PAA$_{140}$-g-PEO$_{3kDa}$-NH-Boc-b-PpHS$_{50}$ (II) as a white solid after lyophilization (1.15 g, 84% yield). M$_n^{NMR}$=58,400 g/mol. $^1$H NMR (DMSO-d$_6$): δ 12.3 (br, 70 H), 8.84 (br, 80 H), 7.22 (m, 10 H), 7.31-6.48 (br, 200 H), 3.52-3.41 (br, 420 H), 2.40-2.10 (br, 140 H), 1.30 (br, 230 H).

Synthesis of poly(acrylic acid)-g-(CONH-PEO$_{3kDa}$-NH$_2$)-b-poly(p-hydroxystyrene) (PAA-g-PEO$_{3kDa}$-NH$_2$-b-PpHS) (III). A flame-dried 100-mL round bottom flask equipped with a magnetic stir bar was charged with 11 (1.15 g, 17.1 µmol). TFA (30 mL) was added to the stirred solution and the reaction mixture was allowed to stir for 24 h at rt, after which the solvent was removed under vacuum. The crude product was re-suspended in THF (20 mL) and transferred to a presoaked dialysis tubing (MWCO ca. 6000-8000 Da), and dialyzed against nanopure H$_2$O for 2 days, to remove all of the impurities, after which the solution was lyophilized to yield PAA-g-PEO$_{3kDa}$-NH$_2$-b-PpHS (III) as a white solid (1.10 mg, 94%). M$_n^{NMR}$=57,700 g/mol. $^1$H NMR (DMSO-d$_6$) δ 12.3 (br, 70 H), 8.84 (br, 80 H), 7.22 (m, 10 H), 7.31-6.48 (br, 200 H), 3.52-3.41 (br, 420 H), 2.40-2.10 (br, 140 H), 1.30 (br, 230 H).

Synthesis of poly(acrylic acid)-g-(CONH-PEO$_{3kDa}$-NHCO—C$_2$H$_4$—SCOCH$_3$)-b-poly(p-hydroxystyrene) (PAA-g-PEO$_{3kDa}$-NHCO—C$_2$H$_4$—SCOCH$_3$-b-PpHS) (IV). A flame-dried 100-mL round bottom flask equipped with a magnetic stir bar was charged with III (1.1 g, 21.0 µmol). N-succinimidyl-5-acetylthiopropionate (SATP) (119 mg, 485 µmol, 2 equiv/NH2) and DIPEA (325 mg, 2.52 mmol) were added to the stirred solution and the reaction mixture was allowed to stir for 12 h at rt before being transferred to a presoaked dialysis tubing (MWCO ca. 6000-8000 Da), and dialyzed against nanopure H$_2$O for 2 days, to remove all of the impurities and afford PAA-g-PEO$_{3kDa}$-NHCO—C$_2$H$_4$—SCOCH$_3$-b-PpHS (IV) as a white solid after lyophilization (835 mg, 76% yield). M$_n^{NMR}$=57,700 g/mol. $^1$H NMR (DMSO-d$_6$) δ 12.2 (br, 70 H), 8.82 (br, 90 H), 7.22 (m, 10 H), 7.31-6.48 (br, 200 H), 4.71-4.58 (br, 28 H), 3.53-3.41 (br, 400 H), 2.40-2.10 (br, 140 H), 1.30 (br, 230 H).

Deprotection procedure to prepare poly(acrylic acid)-g-(CONH-PEO$_{3kDa}$-NHCO—C$_2$H$_4$—SH)-b-poly(p-hydroxystyrene) (PAA-g-PEO$_{3kDa}$-NHCO—C$_2$H$_4$—SH-b-PpHS) (V). Hydroxylamine hydrochloride (500 mL, 0.5 M) in aqueous buffer (100 mM PBS, 0.1 M NaCl, 10 mM EDTA, pH 7.4) was added to a stirred solution of 10 mL of polymer IV (180 mg, 3.44 mmol) suspended in buffer (100 mM PBS, 0.1 M NaCl, 10 mM EDTA, pH 7.4) and stirred for 6 h at room temperature. The solution was assayed by Ellman's method resulting in a concentration of 35±6 µM [HS], theoretical concentration of 41 µM [HS], after which the coupling of bromoacetyl-LCB was performed immediately.

Bromoacetyl-thiol coupling of polymer (V) and bromoacetyl-leukemia cell binding peptide (LCB) to prepare poly(acrylic acid)-g-(CONN-PEO$_{3kDa}$-LCB)-b-poly(p-hydroxystyrene) (PAA-g-PEO$_{3kDa}$-LCB-b-PpHS) (VI). LCB (54 mg, 53 µmol) suspended in DMSO was added to a stirred solution of polymer (V) (239 mg, 4.39 mmol) suspended in buffer (50 mM sodium borate, pH 9). The reaction was allowed to proceed for 6 h, after which the solution pH was adjusted to 6 and allowed to stir overnight at room temperature before being transferred to presoaked dialysis tubing (MWCO ca. 6000-8000 kDa), and dialyzed against buffer (5 mM PBS, 5 mM NaCl, pH 7.4) for 2 days, to remove unconjugated LCB peptide and small molecule impurities. The reaction solution was lyophilized to afford a white solid (270 mg, 92% yield) (VI).

Co-assembly of PAA-g-mPEO$_{2kDa}$-b-PpHS) (I) and PAA-g-PEO$_{3kDa}$-LOB-b-PpHS (VI) to prepare micelles A, B, C, D or E. To a 20-mL scintillation vial was added polymer I (75 mg) followed by 15 mL of nanopure water. The solution was allowed to stir at rt for 12 h to afford micelle A. To a 20-mL scintillation vial was added polymer I (50 mg) and VI (25 mg) followed by 15 mL of nanopure water. The solution was allowed to stir at rt for 12 h to afford micelle B. To a 20-mL scintillation vial was added polymer I (37.5 mg) and VI (37.5 mg) followed by 15 mL of nanopure water. The solution was allowed to stir at rt for 12 h to afford micelle C. To a 20-mL scintillation vial was added polymer I (25 mg) and VI (50 mg) followed by 15 mL of nanopure water. The solution was allowed to stir at rt for 12 h to afford micelle D. To a 20-mL scintillation vial was added polymer VI (75 mg) followed by 15 mL of nanopure water. The solution was allowed to stir at rt for 12 h to afford micelle E.

Shell crosslinking of micelles to afford LCB-SCK-A. To a 20-mL scintillation vial equipped with a magnetic stir bar was added a solution of micelle A (19.4 mg, 0.437 µmol). To this solution, was added 3,6-diamino-N$^2$,N$^5$-bis(2-aminoethyl)pyrazine-2,5-dicarboxamide: 0.60 mg, 1.68 µmol (3.85 mol % relative to the acrylic acid residues) for 2% crosslinking extent); 2.39 mg, 6.75 µmol (15.4 mol % relative to the acrylic acid residues) for 7% crosslinking extent; or 5.93 mg, 16.7 µmol (38.5 mol % relative to the acrylic acid residues) for 14% crosslinking extent). The reaction mixture was allowed to stir at rt for 2 h. To this solution was added, dropwise via a syringe pump over 1 h, a solution of 1-[3'-(dimethylamino)propyl]-3-ethylcarbodiimide methiodide (EDCI, 1.09 mg, 3.67 µmol for 2% crosslinking extent; or 4.37 mg, 14.7 µmol for 7% crosslinking extent; or 10.9 mg, 36.5 µmol for 15% crosslinking extent) and the reaction mixture was further stirred at rt for 16 h. Finally, the reaction mixture was transferred to pre-soaked dialysis tubing (MWCO ca. 3,500 Da)

and dialyzed against nanopure water for 3 d to remove the non-attached crosslinker, excess small molecule starting materials and by-products, and afford aqueous solutions of LCB-shell-crosslinked nanoparticle A (LCB-SCK-A2%, 7% or 15%) (final polymer concentration: 1.46 mg/mL, 1.32 mg/mL or 1.02 mg/mL, respectively—where in each case, the % crosslinking was determined by UV-vis spectroscopic measurement of the amount of crosslinker remaining after purification).

Shell crosslinking of micelles to afford LCB-SCK-B. To a 20-mL scintillation vial equipped with a magnetic stir bar was added a solution of micelle B (20.0 mg, 0.404 μmol). To this solution, was added 3,6-diamino-$N^2,N^5$-bis(2-aminoethyl)pyrazine-2,5-dicarboxamide: 0.551 mg, 1.56 μmol (3.85 mol % relative to the acrylic acid residues) for 2% crosslinking extent); 2.20 mg, 6.21 μmol (15.4 mol % relative to the acrylic acid residues) for 8% crosslinking extent; or 5.53 mg, 15.6 μmol (38.5 mol % relative to the acrylic acid residues) for 19% crosslinking extent). The reaction mixture was allowed to stir at rt for 2 h. To this solution was added, dropwise via a syringe pump over 1 h, a solution of 1-[3'-(dimethylamino)propyl]-3-ethylcarbodiimide methiodide (EDCI, 1.01 mg, 3.39 μmol for 2% crosslinking extent; or 4.02 mg, 13.5 μmol for 9% crosslinking extent; or 10.1 mg, 34.0 μmol for 20% crosslinking extent) and the reaction mixture was further stirred at rt for 16 h. Finally, the reaction mixture was transferred to pre-soaked dialysis tubing (MWCO ca. 3,500 Da) and dialyzed against nanopure water for 3 d to remove the non-attached crosslinker, excess small molecule starting materials and by-products, and afford aqueous solutions of LCB-shell-crosslinked nanoparticle B (LCB-SCK-B2%, 9% or 20%) (final polymer concentration: 1.46 mg/mL, 1.28 mg/mL or 1.00 mg/mL, respectively—where in each case, the % crosslinking was determined by UV-vis spectroscopic measurement of the amount of crosslinker remaining after purification).

Shell crosslinking of micelles to afford LCB-SCK-C. To a 20-mL scintillation vial equipped with a magnetic stir bar was added a solution of micelle C (20.8 mg, 0.395 μmol). To this solution, was added 3,6-diamino-$N^2,N^5$-bis(2-aminoethyl)pyrazine-2,5-dicarboxamide: 0.538 mg, 1.52 μmol (3.85 mol % relative to the acrylic acid residues) for 2% crosslinking extent); 2.15 mg, 6.08 μmol (15.4 mol % relative to the acrylic acid residues) for 7% crosslinking extent; or 5.43 mg, 15.3 μmol (38.5 mol % relative to the acrylic acid residues) for 17% crosslinking extent). The reaction mixture was allowed to stir at rt for 2 h. To this solution was added, dropwise via a syringe pump over 1 h, a solution of 1-[3'-(dimethylamino)propyl]-3-ethylcarbodiimide methiodide (EDCI, 0.986 mg, 3.32 μmol for 2% crosslinking extent; or 3.94 mg, 13.2 μmol for 10% crosslinking extent; or 9.95 mg, 33.3 μmol for 22% crosslinking extent) and the reaction mixture was further stirred at rt for 16 h. Finally, the reaction mixture was transferred to pre-soaked dialysis tubing (MWCO ca. 3,500 Da) and dialyzed against nanopure water for 3 d to remove the non-attached crosslinker, excess small molecule starting materials and by-products, and afford aqueous solutions of LCB-shell-crosslinked nanoparticle C (LCB-SCK-C2%, 10% or 22%) (final polymer concentration: 1.39 mg/mL, 1.31 mg/mL or 1.09 mg/mL, respectively—where in each case, the % crosslinking was determined by UV-vis spectroscopic measurement of the amount of crosslinker remaining after purification).

Shell crosslinking of micelles to afford LCB-SCK-D. To a 20-mL scintillation vial equipped with a magnetic stir bar was added a solution of micelle D (20.1 mg, 0.357 μmol). To this solution, was added 3,6-diamino-$N^2,N^5$-bis(2-aminoethyl)pyrazine-2,5-dicarboxamide: 0.487 mg, 1.38 μmol (3.85 mol % relative to the acrylic acid residues) for 2% crosslinking extent); 1.95 mg, 5.50 μmol (15.4 mol % relative to the acrylic acid residues) for 6% crosslinking extent; or 4.90 mg, 13.9 μmol (38.5 mol % relative to the acrylic acid residues) for 14% crosslinking extent). The reaction mixture was allowed to stir at rt for 2 h. To this solution was added, dropwise via a syringe pump over 1 h, a solution of 1-[3'-(dimethylamino)propyl]-3-ethylcarbodiimide methiodide (EDCI, 0.892 mg, 3.00 μmol for 3% crosslinking extent; or 3.57 mg, 12.0 μmol for 11% crosslinking extent; or 8.98 mg, 30.2 μmol for 24% crosslinking extent) and the reaction mixture was further stirred at rt for 16 h. Finally, the reaction mixture was transferred to pre-soaked dialysis tubing (MWCO ca. 3,500 Da) and dialyzed against nanopure water for 3 d to remove the non-attached crosslinker, excess small molecule starting materials and by-products, and afford aqueous solutions of LCB-shell-crosslinked nanoparticle D (LCB-SCK-D3%, 11% or 24%) (final polymer concentration: 1.15 mg/mL, 1.06 mg/mL or 0.958 mg/mL, respectively—where in each case, the % crosslinking was determined by UV-vis spectroscopic measurement of the amount of crosslinker remaining after purification).

Shell crosslinking of micelles to afford LCB-SCK-E. To a 20-mL scintillation vial equipped with a magnetic stir bar was added a solution of micelle E (20.4 mg, 0.315 μmol). To this solution, was added 3,6-diamino-$N^2,N^5$-bis(2-aminoethyl)pyrazine-2,5-dicarboxamide: 0.429 mg, 1.21 μmol (3.85 mol % relative to the acrylic acid residues) for 2% crosslinking extent); 1.72 mg, 4.85 μmol (15.4 mol % relative to the acrylic acid residues) for 6% crosslinking extent; or 4.34 mg, 12.3 μmol (38.5 mol % relative to the acrylic acid residues) for 15% crosslinking extent). The reaction mixture was allowed to stir at rt for 2 h. To this solution was added, dropwise via a syringe pump over 1 h, a solution of 1-[3'-(dimethylamino)propyl]-3-ethylcarbodiimide methiodide (EDCI, 0.786 mg, 2.64 μmol for 4% crosslinking extent; or 3.14 mg, 10.6 μmol for 6% crosslinking extent; or 7.95 mg, 26.7 μmol for 25% crosslinking extent) and the reaction mixture was further stirred at rt for 16 h. Finally, the reaction mixture was transferred to pre-soaked dialysis tubing (MWCO ca. 3,500 Da) and dialyzed against nanopure water for 3 d to remove the non-attached crosslinker, excess small molecule starting materials and by-products, and afford aqueous solutions of LCB-shell-crosslinked nanoparticle E (LCB-SCK-E4%, 6% or 25%) (final polymer concentration: 1.01 mg/mL, 0.783 mg/mL or 0.835 mg/mL, respectively—where in each case, the % crosslinking was determined by UV-vis spectroscopic measurement of the amount of crosslinker remaining after purification).

General procedure for loading MP-3397 into LCB-SCKs. To a 20-mL scintillation vial equipped with a magnetic stir bar was added a solution of micelle (7.89 mg, 5.42 μmol). To this solution, was added diethyl 1-(anthracen-9-yl)hydrazine-1,2-dicarboxylate (MP-3397) (0.395 mg, 5 wt %). The reaction mixture was allowed to stir at rt overnight. Finally, the reaction mixture was transferred to pre-soaked dialysis tubing (MWCO ca. 3,500 Da) and dialyzed against nanopure water for 2 d to remove excess small molecule starting materials and afford aqueous solutions of MP-3397-LCB-shell-crosslinked nanoparticle (final polymer concentration: 1.07 mg/mL).

Figure 20:
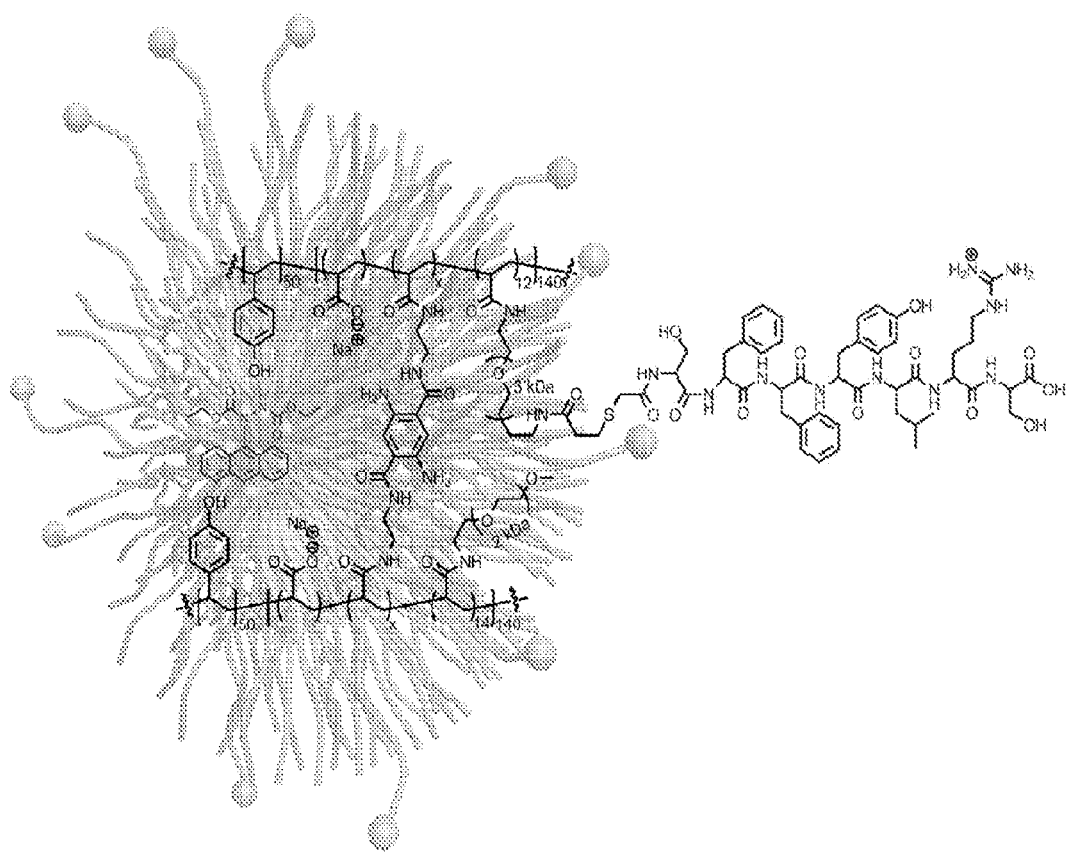
FIG. 20 provides a schematic diagram of one embodiment of the particles described.

FIG. 20 provides a schematic diagram of one embodiment of the particles described in this aspect of the invention.

Core loading was achieved by addition of MP-3397 stock solution (in DMF) into aqueous micelle solution followed by removal of organic solvent through dialysis. Alternatively, MP-3397 stock solution incubated with block copolymer (both in DMF) underwent co-assembly upon addition of water followed by dialysis. In an example, poly(p-hydroxystyrene) core achieved maximum of 5 wt % core loading whereas polystyrene core achieved ca. 15 wt %. Previously, poly(p-hydroxystyrene) core has been shown to load 15 wt % of MP-4089

The LCB-peptide was conjugated via thiol-bromoacetyl. The reaction was carried out at pH 9 for 3 hours under nitrogen. The solution pH was adjusted to 6 and maleimidobutyric acid was added to react with any residual thiol groups. The reaction mixture was purified by dialysis against 5 mM PBS and lyophilized to afford LCB-PEO$_{3k}$ block copolymer. A separate batch of mPEO$_{2k}$ block copolymer has been synthesized to be co-assembled with the LCB-PEO$_{3k}$ block copolymer. These reactions are shown in Scheme 1 of this Example 7:

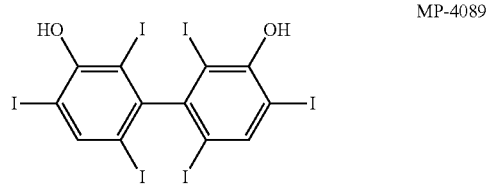 [SMILES: Oc1c(I)cc(I)c(-c2c(I)cc(I)c(O)c2I)c1I]

MP-4089

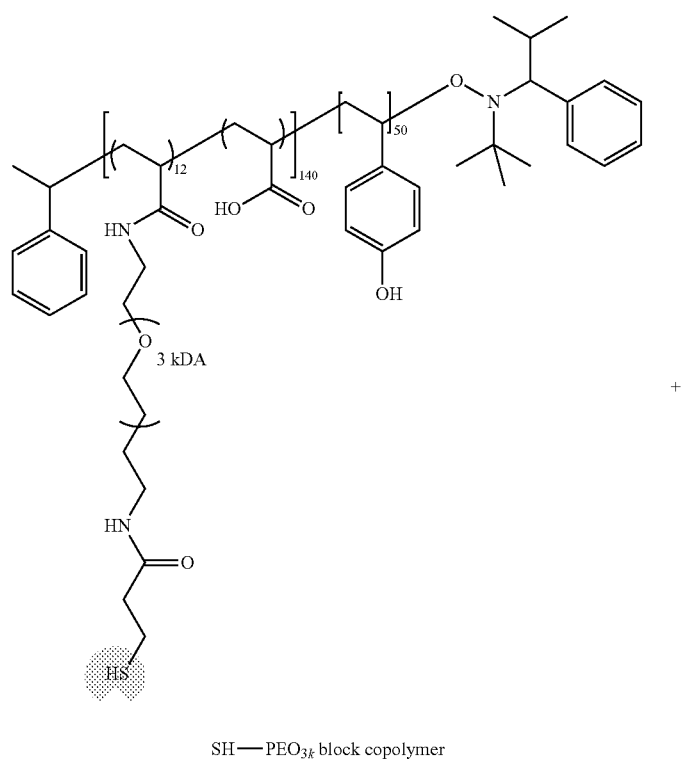

SH—PEO$_{3k}$ block copolymer

+

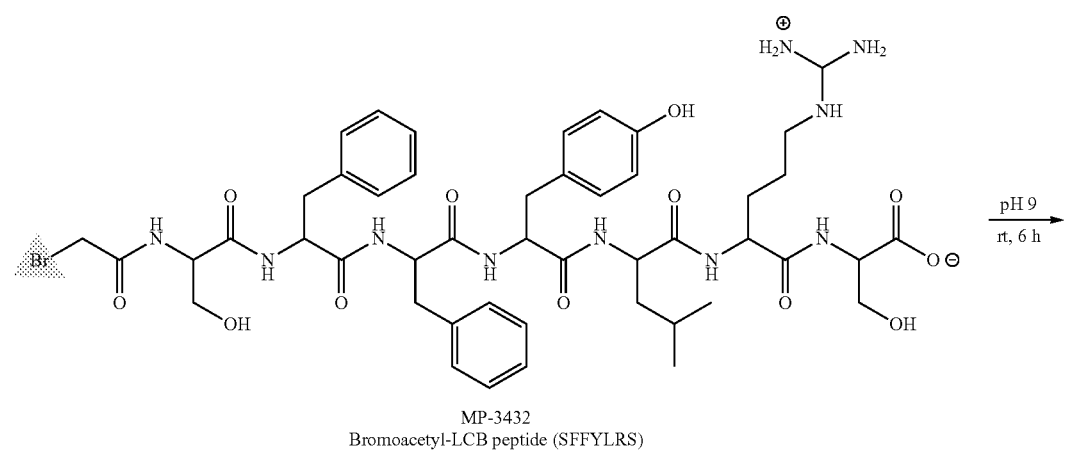

MP-3432
Bromoacetyl-LCB peptide (SFFYLRS)

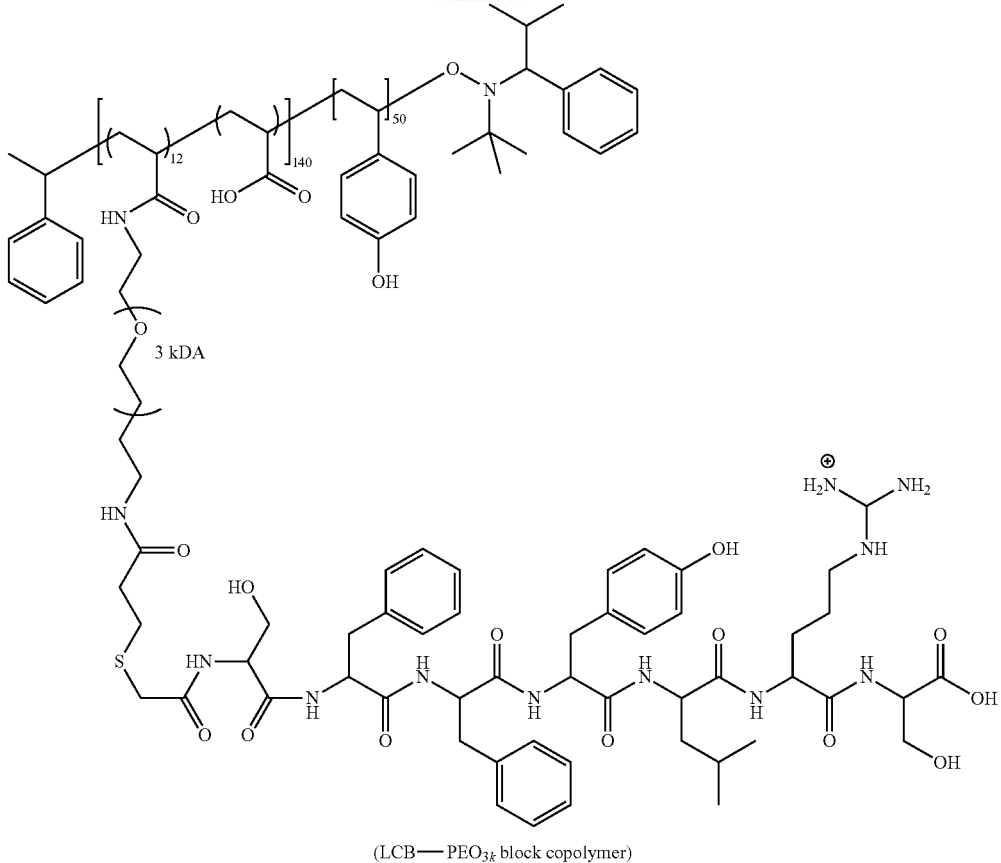

(LCB—PEO$_{3k}$ block copolymer)

Co-assembly of mPEO$_{2k}$ and LCB-PEO$_{3k}$ block copolymers followed by shell crosslinking reactions afforded targeted SCKs with a variable number of targeting peptides. Micelles D and E series underwent shell crosslinking reactions in a mixed solvent system (10 v/v % DMSO) with MP-3124 due to low water solubility

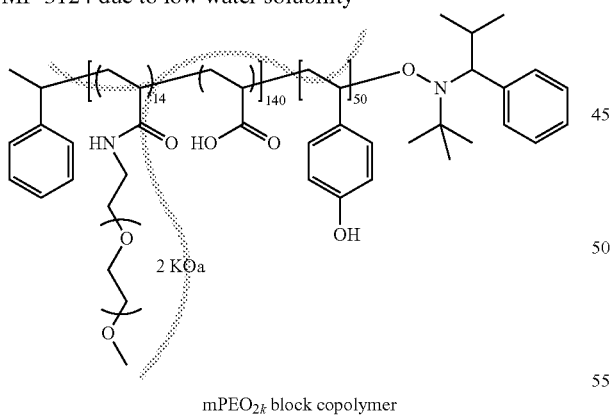

mPEO$_{2k}$ block copolymer

The size and zeta potential for various LCB-SCKs are provided in Table 8:

TABLE 8

| SCK | weight ratio mPEO$_{2k}$:LCB-PEO$_{3k}$ | % LCB | % mPEO$_{2k}$ | # LCB/ polymer | D$_h$ (nm) | ζ (mV)$^a$ | D$_h$ (nm) | ζ (mV)$^a$ | Xlink density | conc. (mg/ml) |
|---|---|---|---|---|---|---|---|---|---|---|
| A | 75 mg to 0 mg | 0 | 10 | 0 | 25 ± 3 | −27 ± 2 | 20 ± 5 | −36 ± 2 | 2% | 1.5 |
|   |   |   |   |   |   |   | 20 ± 5 | −38 ± 3 | 7% | 1.3 |
|   |   |   |   |   |   |   | 14 ± 4 | −31 ± 1 | 15% | 1.0 |

TABLE 8-continued

| SCK | weight ratio mPEO$_{2k}$: LCB-PEO$_{3k}$ | % LCB | % mPEO$_{2k}$ | # LCB/ polymer | D$_h$ (nm) | ζ (mV)$^a$ | D$_h$ (nm) | ζ (mV)$^a$ | Xlink density | conc. (mg/ml) |
|---|---|---|---|---|---|---|---|---|---|---|
| B | 50 mg to 25 mg | 1.9 | 7.7 | 2.7 | 17 ± 2 | −29 ± 1 | 19 ± 5 | −33 ± 4 | 2% | 1.5 |
|   |   |   |   |   |   |   | 15 ± 4 | −35 ± 2 | 9% | 1.3 |
|   |   |   |   |   |   |   | 15 ± 4 | −34 ± 3 | 20% | 1.0 |
| C | 37.5 mg to 37.5 mg | 3.2 | 6.3 | 4.5 | 15 ± 3 | −27 ± 2 | 16 ± 4 | −27 ± 2 | 2% | 1.4 |
|   |   |   |   |   |   |   | 14 ± 4 | −27 ± 2 | 10% | 1.3 |
|   |   |   |   |   |   |   | 12 ± 3 | −27 ± 1 | 22% | 1.1 |
| D | 25 mg to 50 mg | 5.3 | 3.8 | 7.4 | 14 ± 2 | −17 ± 4 | 13 ± 3 | −25 ± 1 | 3% | 1.2 |
|   |   |   |   |   |   |   | 12 ± 3 | −24 ± 3 | 11% | 1.1 |
|   |   |   |   |   |   |   | 9 ± 2 | −24 ± 1 | 24% | 1.0 |
| E | 0 mg to 75 mg | 8.6 | 0 | 12 | 14 ± 2 | −20 ± 1 | 14 ± 4 | −26 ± 3 | 4% | 1.0 |
|   |   |   |   |   |   |   | 13 ± 4 | −26 ± 3 | 6% | 0.8 |
|   |   |   |   |   |   |   | 11 ± 3 | −15 ± 4 | 25% | 0.8 |

Two block copolymers, mPEO$_{2kDa}$ or LCB-PEO$_{3kDa}$ grafted block copolymers, were formulated at five different wt. ratios and subsequently shell-crosslinked at three different xlink densities with MP-3142 to give rise to 15 SCKs, each of which was loaded with 5 wt % of MP-3397. These formulations are provided below in Table 9.

TABLE 9

NL-iv-62A
MP3397-mPEO-SCK A2

| Polymer conc. = | 1.1 mg/mL |
| MP3397 conc. = | 53 μg/mL |
| LCB conc. = | 0 μg/mL |

NL-iv-62B
MP3397-mPEO-SCK A7

| Polymer conc. = | 1.0 mg/mL |
| MP3397 conc. = | 50 μg/mL |
| LCB conc. = | 0 μg/mL |

NL-iv-62C
MP3397-mPEO-SCK A15

| Polymer conc. = | 0.82 mg/mL |
| MP3397 conc. = | 4.1 μg/mL |
| LCB conc. = | 0 μg/mL |

NL-iv-63A
MP3397-LCB-SCK B2

| Polymer conc. = | 1.1 mg/mL |
| MP3397 conc. = | 53 μg/mL |
| LCB conc. = | 67 μg/mL |

NL-iv-63B
MP3397-LCB-SCK B9

| Polymer conc. = | 0.93 mg/mL |
| MP3397 conc. = | 46 μg/mL |
| LCB conc. = | 60 μg/mL |

NL-iv-63C
MP3397-LCB-SCK B20

| Polymer conc. = | 0.78 mg/mL |
| MP3397 conc. = | 39 μg/mL |
| LCB conc. = | 50 μg/mL |

NL-iv-64A
MP3397-LCB-SCK C2

| Polymer conc. = | 1.0 mg/mL |
| MP3397 conc. = | 51 μg/mL |
| LCB conc. = | 98 μg/mL |

NL-iv-64B
MP3397-LCB-SCK C10

| Polymer conc. = | 0.94 mg/mL |
| MP3397 conc. = | 47 μg/mL |
| LCB conc. = | 90 μg/mL |

TABLE 9-continued

NL-iv-64C
MP3397-LCB-SCK C22

| Polymer conc. = | 0.78 mg/mL |
| MP3397 conc. = | 39 μg/mL |
| LCB conc. = | 75 μg/mL |

NL-iv-65A
MP3397-LCB-SCK D3

| Polymer conc. = | 0.80 mg/mL |
| MP3397 conc. = | 40 μg/mL |
| LCB conc. = | 100 μg/mL |

NL-iv-65B
MP3397-LCB-SCK D11

| Polymer conc. = | 0.76 mg/mL |
| MP3397 conc. = | 38 μg/mL |
| LCB conc. = | 97 μg/mL |

NL-iv-65C
MP3397-LCB-SCK D24

| Polymer conc. = | 0.69 mg/mL |
| MP3397 conc. = | 35 μg/mL |
| LCB conc. = | 89 μg/mL |

NL-iv-66A
MP3397-LCB-SCK E4

| Polymer conc. = | 0.72 mg/mL |
| MP3397 conc. = | 36 μg/mL |
| LCB conc. = | 140 μg/mL |

NL-iv-66B
MP3397-LCB-SCK E6

| Polymer conc. = | 0.60 mg/mL |
| MP3397 conc. = | 30 μg/mL |
| LCB conc. = | 120 μg/mL |

NL-iv-66C
MP3397-LCB-SCK E25

| Polymer conc. = | 0.64 mg/mL |
| MP3397 conc. = | 32 μg/mL |
| LCB conc. = | 102 μg/mL |

Figure 21:
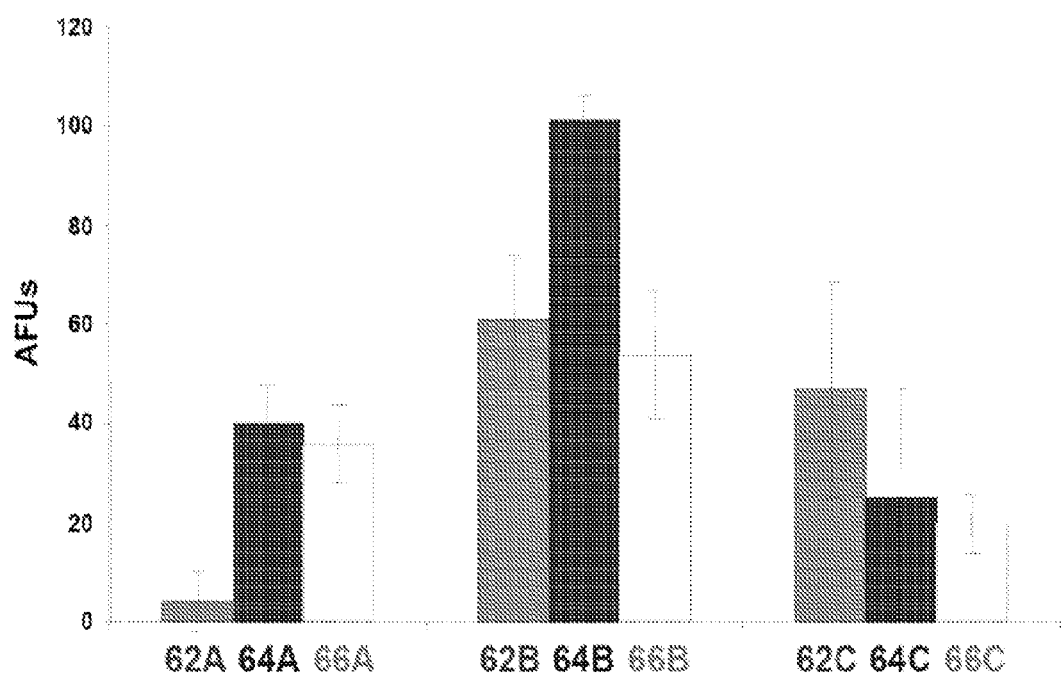
FIG. 21 shows results of binding studies in U937 cells.

In these formulations, the concentration of MP-3397 was kept the same in the nanoparticles for all the formulations tested, for both binding as well as toxicity studies; 80,000 cells were plated in 24 well plate on the same day; Cells were incubated for 2 hours with nanoparticles. For binding studies cells were washed at the end of 2 hour and lysed. Fluorescence of MP-3142 was then measured. Cells were then washed twice and further incubated for 2 hours. At the end of 4 hour incubation, plates were exposed to light source for 20 mins. After 24 hours the metabolic activity of U937 was assessed with WST-1. Metabolic activity=cell viability. FIG. 21 shows results of these studies.

Particles NL-iv-6XA and then NL-iv-6XB series showed maximum binding as monitored by MP-3142 fluorescence.

The binding in this series showed increasing signal with increase in targeting peptide which was lost at the highest concentration of targeting peptide (this may be due to a multivalency issue). The NL-iv-6XC series showed a binding profile opposite to other two series. It is considered that the highest cross linking density might inhibit the binding or reduce the availability of peptide. In addition, the fluorescence of MP-3142 is quenched in these particles.

Figure 22:
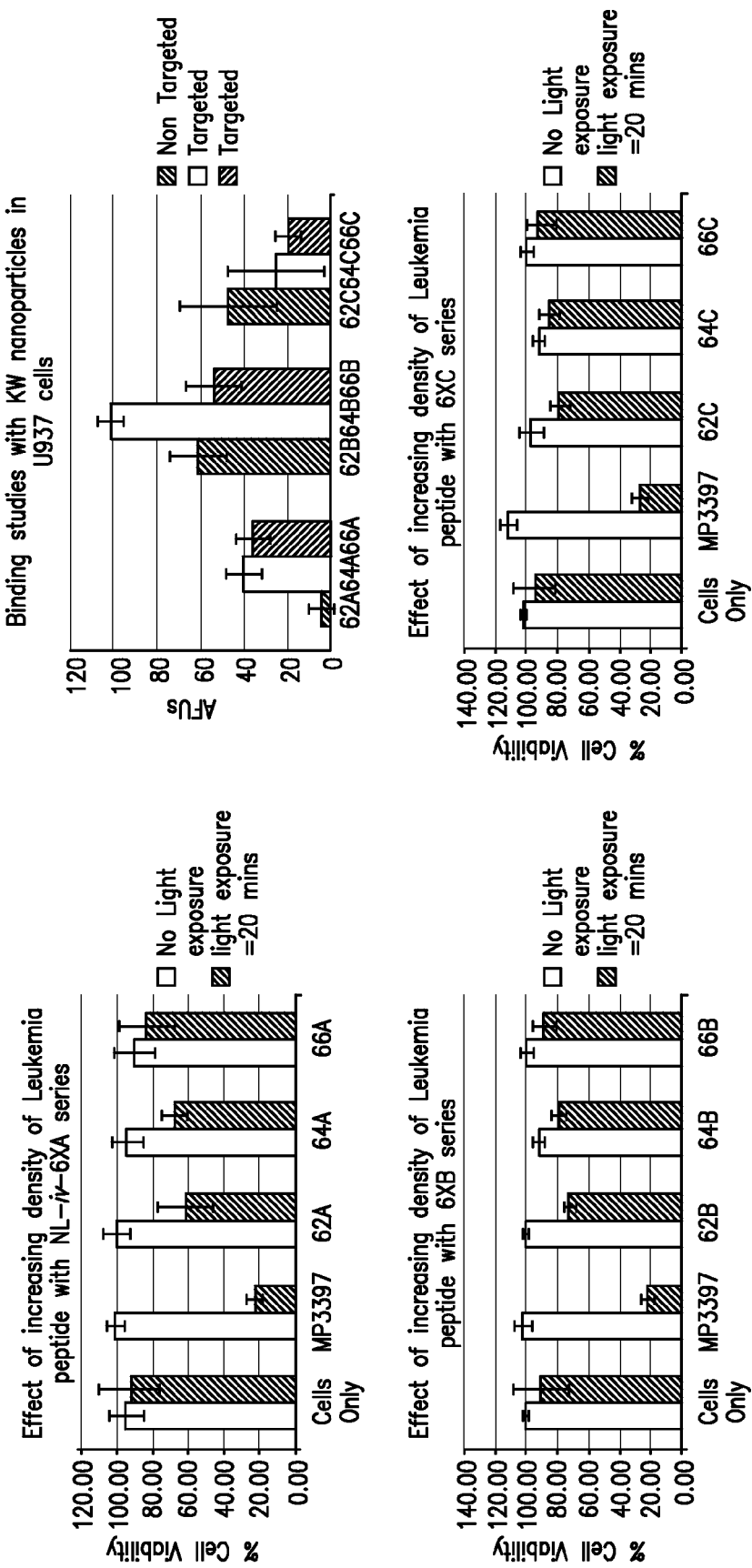
FIG. 22 shows the effect of increasing concentration of Leukemia peptide on the targeting efficiency of nanoparticles.

FIG. 22 shows the effect of increasing concentration of Leukemia peptide on the targeting efficiency of nanoparticles. The targeting vector had minimal effect on the toxicity induced in U937 cells indicating the peptide availability for binding.

Figure 23A:
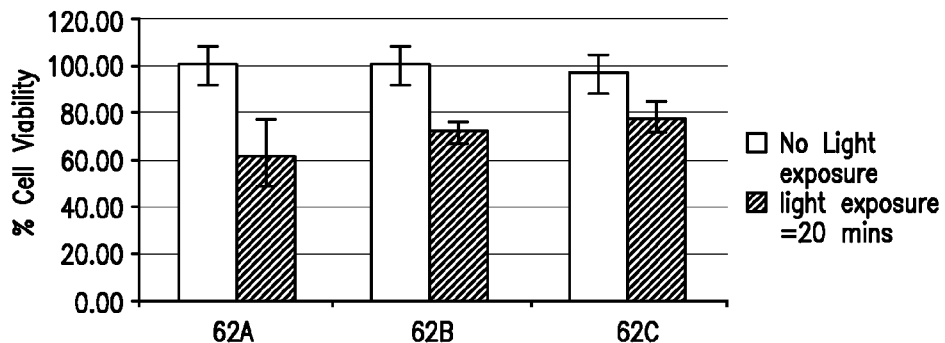
FIG. 23 A-C shows the effect of increasing crosslink density on NP induced toxicity in U937 cells.
Figure 23B:
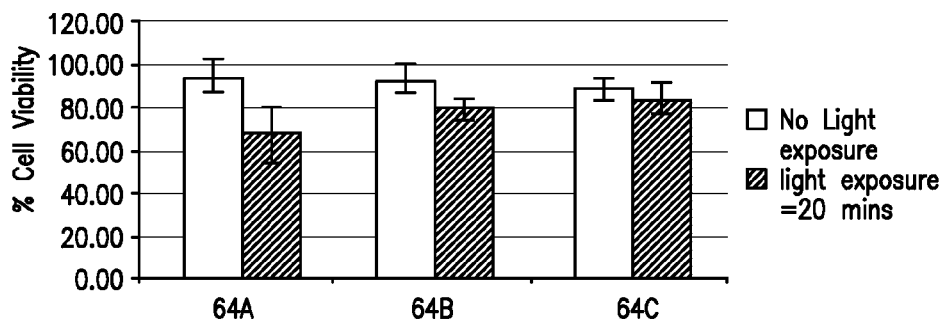
Figure 23C:
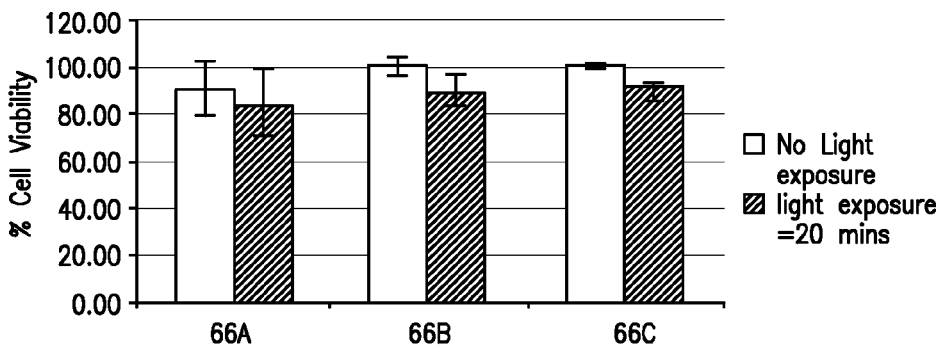

FIG. 23 A-C shows the effect of increasing crosslink density on NP induced toxicity in U937 cells. NL-iv-6XA series showed more toxicity than 6XB and 6XC series of formulations: 6XA>6XB>6XC. This may be caused by the crosslinking might be making particle more rigid inhibiting drug release or the drug is being activated before it is released from the nanoparticles

EXAMPLE 8

Additional Examples of Biophotonic Embedded Therapeutic Molecule/Biotargeting Compounds of the invention are also useful for targeting biological moieties. Targeted moieties may also undergo subsequent or coincident phototherapeutic applications. In aspects of this embodiment, compounds of the formulas described herein contain one or more biotargeting groups. Examples of biotargeting groups are well known in the art. By way of example, the optical agent which includes a targeting moiety can be administered to a patient in a diagnostically effective amount to detect the optical agent within the patient. After a period of time has lapsed for the compound to bind to the desired target, the whole body or portion thereof is exposed to light of suitable wavelength to excite the optical agent. Light emanating from the patient as a result of the absorption and excitation of the optical agent is then detected. By evaluating the location and strength of light emanating from the patient, a diagnosis can be made as a result of the targeting properties of the optical agent.

In embodiments, compounds of the invention are useful for both oncology and non-oncology applications. Some specific applications. Other specific targets include colon, lung, ovarian, cervical, esophageal, bladder, blood, and stomach cancers; endometriosis, and bacterial infections. Particular targeting groups include ST receptor binding agents, bombesin receptor binding agents, leukemia peptides, and folate receptor binding. Some examples of targeting peptides are described in WO/2008/108941. Specific targeting ligands include peptides known in the art for targeting, such as the leukemia cell binding peptide Ser-Phe-Phe-Tyr-Leu-Arg-Ser (SFFYLRS, SEQ ID NO: 1). Folate receptor targets are disclosed in Rossin, et al., J. Nucl. Med., 46(7), 1210-1218 (2005); Zhang, et al., J. Poly. Sci: A: Polymer Chemistry, 46, 7578-7583 (2008) for example. The use of the Tat peptide is described in Liu, et al., Biomacromolecules, 2, 362-368 (2001), Zhang, et al., Bioconjugate Chem., 19, 1880-1887 (2008), for example.

Figure 24:
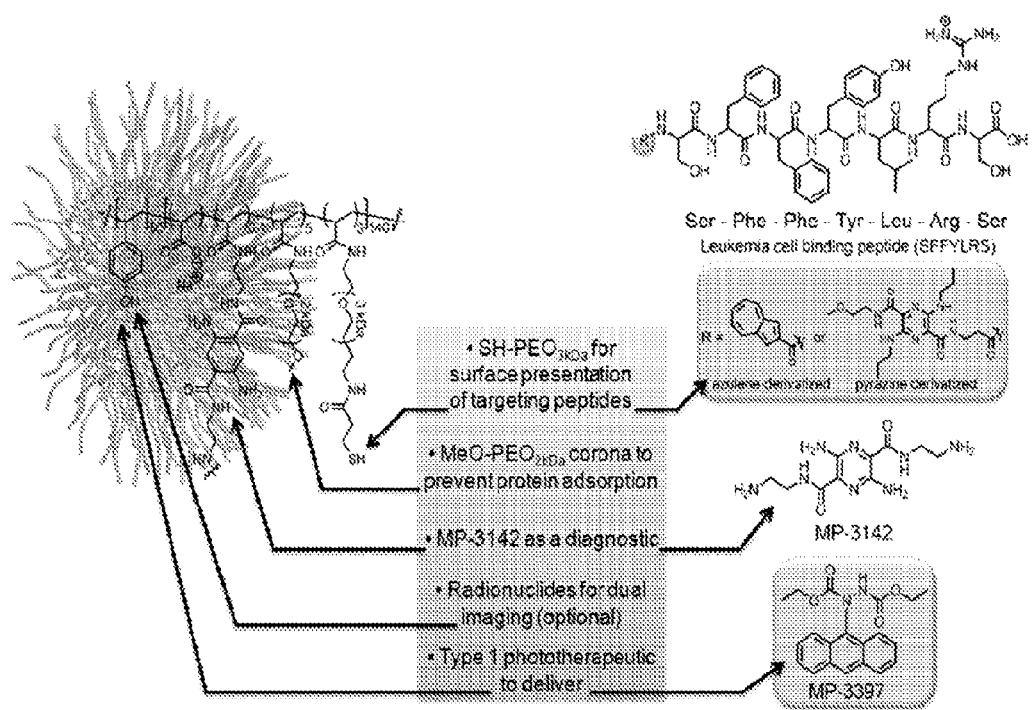
FIG. 24 shows a schematic of the various portions of the molecules.

In this series of experiments, a physical mixture of the SCK and various peptides such as the leukemia cell binding peptide SFFYLRS (SEQ ID NO: 1) and phototherapeutic moieties such as MP3397 were prepared. FIG. 24 shows a schematic of the various portions of the molecules. The preparation of these molecules is described elsewhere herein. The maximum loading capacity using MP-3397 was determined by observing the absence of precipitation. The amount of peptide loaded was based on a calculation (one peptide molecule per two polymer chains). MP-3142 was omitted in certain characterization experiments. Based on qualitative experiments (data not shown), different photophysical properties are expected depending on the order in which the drug/peptide molecule are loaded. As shown in FIG. 24, the polymer chains can be derivatized with azulene moieties and pyrazine moieties, for example. These modifications are readily carried out by a person having ordinary skill in the art.

In addition stealth MP-3142-shell-crosslinked nanostructures whose core is loaded with MP-3397 for delivery and leukemia cell binding peptides (SFFYLRS, SEQ ID NO: 1) were covalently conjugated and presented on the surface for targeting. The leukemia cell binding peptide can be azulene derivatized or pyrazine derivatized as shown in FIG. 24. MP-3397 loaded micelles having a polymer concentration of 1.0 mg/mL and a MP-3397 concentration of 0.041 mg/mL were also prepared. In these samples, the fluorescence emission peaks range from about 400 to 500 nm (data not shown). Azulene-derivatized leukemia cell binding peptide loaded micelles having the formula below:

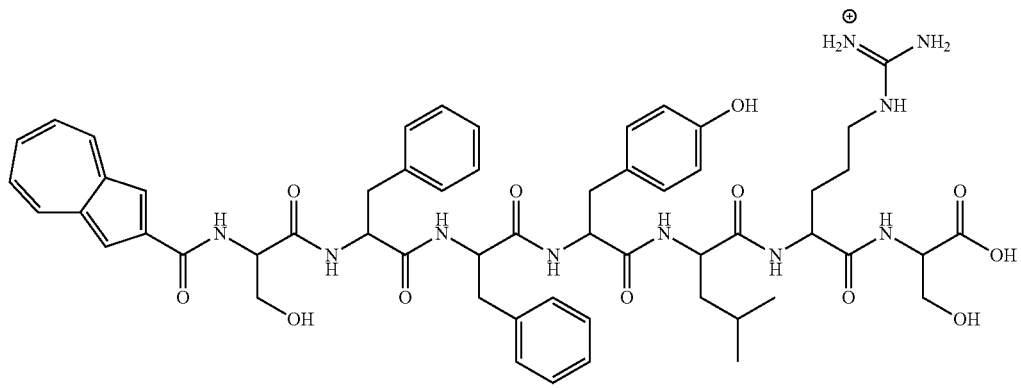

Ser-Phe-Phe-Tyr-Leu-Arg-Ser
Leukemia cell binding peptide (azulene derivatized)SFFYLRS targets are tumors accessible via endoscope. In this application, an optical agent that targets a peptide associated with such a tumor is administered to the tumor via endoscope or other useful method. Then, the compounds of the invention can be used in phototherapeutic applications or imaging having a polymer concentration of 0.73 mg/mL and a peptide concentration of 0.024 mg/mL showed λmax of 361 nm. Pyrazine-derivatized leukemia cell binding peptide loaded micelles having the formula below:

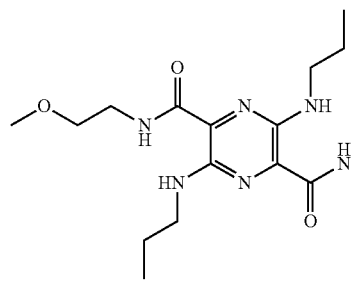

Ser-Phe-Phe-Tyr-Leu-Arg-Ser
Leukemia cell binding peptide (pyrazine derivatized):SFFYLRS and a polymer concentration of 0.768 mg/mL and a peptide concentration of 0.027 mg/mL showed a λmax of 453 nm. The pyrazine peptide emission does not overlap with MP-3397 in its fluorescence emission wavelength.

Doubly-loaded micelles having both MP-3397 and the leukemia cell binding peptide SFFYLRS (SEQ ID NO: 1) where the leukemia cell binding peptide and MP-3397 were added either first or second were prepared. These micelles could be monitored using UV-vis and fluorescence (data not shown) and showed different spectral properties.

Scheme 1 of Example 8 shows the preparation of doubly loaded micelles with the leukemia cell binding peptide added second.

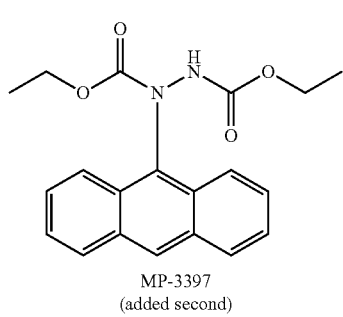

MP-3397
(added second)

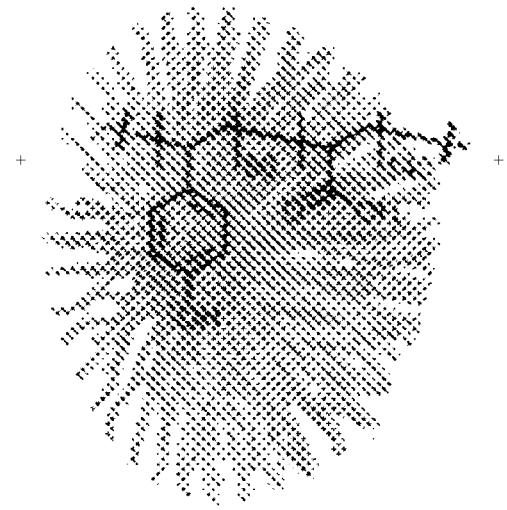

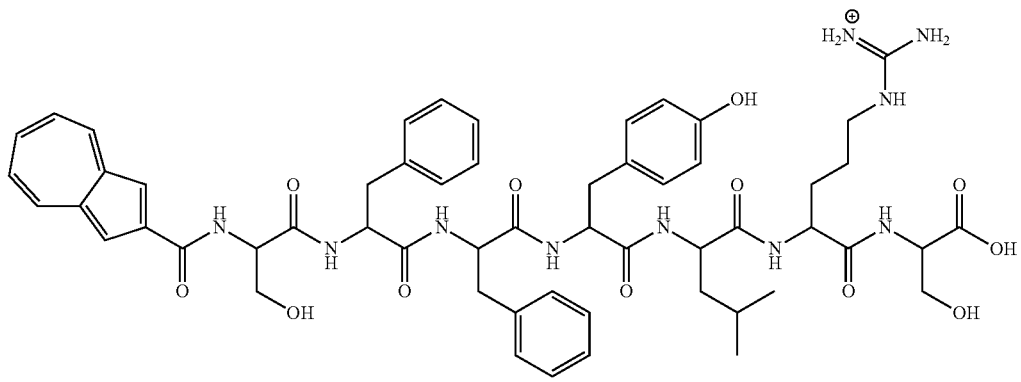

Ser-Phe-Tyr-Leu-Arg-Ser
Leukemia cell binding peptide (azulene derivatized): SFFYLR5

Scheme 2 of Example 8 shows the preparation of doubly loaded micelles with MP-3397 added second.

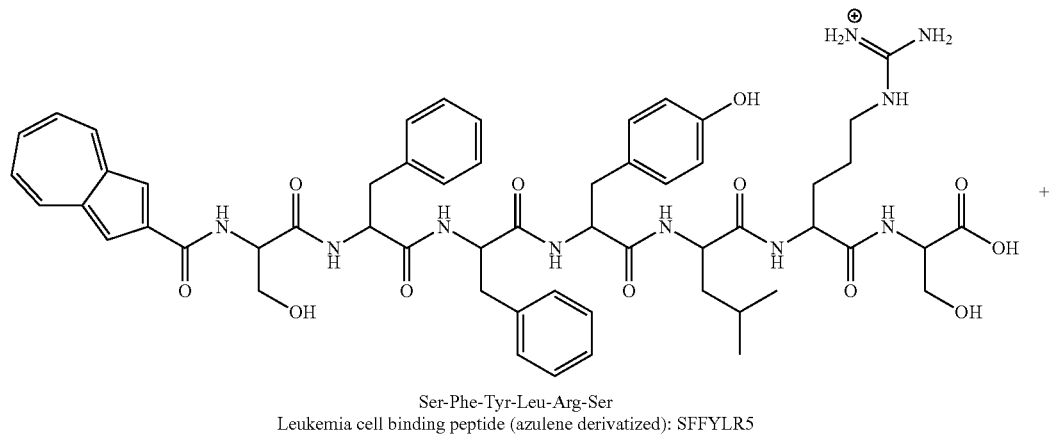

Ser-Phe-Tyr-Leu-Arg-Ser
Leukemia cell binding peptide (azulene derivatized): SFFYLR5

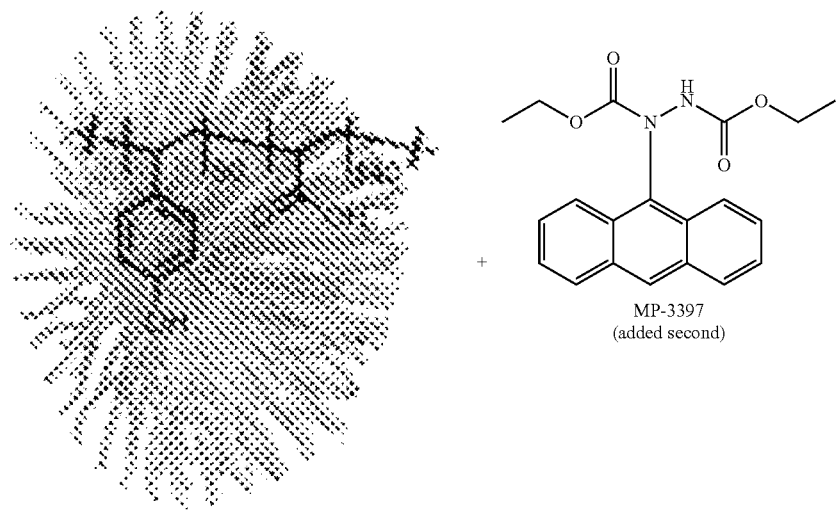

MP-3397
(added second)

EXAMPLE 9

Optical Imaging Using Functional Cross-Linked Nanostructures

In general, molecules absorbing, emitting, or scattering in the visible or NIR region of the electromagnetic spectrum are useful for optical measurement. The high sensitivity associated with fluorescence permits detection without the negative effects of radioactivity or ionizing radiation. Functional cross-linked nanostructures of the invention absorb strongly in the visible and NIR regions.

In an embodiment of this aspect, the invention provides a method of using an optical agent, for example, in a biomedical procedure for optically imaging or visualizing a target tissue or a class of target tissues in connection with tandem therapy. The present methods include tissue selective imaging and visualization methods, such as imaging or visualization of tumor tissue. A method of this aspect comprises the step of administering a diagnostically effective amount of a compound to a subject, wherein the compound is a compound having any of formulas described herein or a pharmaceutical preparation thereof. The present methods are useful for imaging or visualizing colorectal cancer and other cancers, including prostate cancer, gastric cancer, esophageal cancer, uterine-endometrial cancer, pancreatic cancer, breast cancer, cervical cancer, head and neck cancer, hepatic cancer, skin cancer, gallbladder cancer, lung cancer and ovarian cancer.

In methods of this aspect, the compound that has been administered to the subject then is exposed in vivo to electromagnetic radiation and electromagnetic radiation emitted or scattered by the compound is then detected. In some embodiments, fluorescence is excited from the compound (e.g., due to the electromagnetic radiation exposure), optionally via multiphoton excitation processes. In an embodiment particularly useful for imaging and/or visualization, the method of this aspect further comprises: (i) exposing a compound, such as a compound having any one of formulas described herein, administered to the subject to electromagnetic radiation capable of exciting emission from the compound; and (ii) measuring the emission from the compound. In some embodiments, the methods of the present invention use fluorescence excitation via exposure to light having wavelengths selected over the range of 400-1300 nm. For example, optical coherence tomography (OCT) is an optical imaging technique compatible with the present compounds that allows high resolution cross sectional imaging of tissue microstructure. Use of electromagnetic radiation having wavelengths selected over the range of 400 nanometers to 1300 nanometers may be useful for some in situ optical imaging methods of the present invention, including biomedical applications for imaging organs, tissue and/or tumors, anatomical visualization, optical guided surgery and endoscopic procedures. Compounds in present methods may function as contrast agents, optical probes and/or tracer elements. The methods of the present invention include in vivo, in vitro and ex vivo imaging and visualization. The present invention provides methods for a range of clinical procedures, including optical imaging methods and/or visualization guided surgery and/or endoscopic diagnostic and therapeutic procedures.

In an exemplary protocol of uses of the compounds of the invention for a biomedical imaging procedure, a functional cross-linked nanostructures is exposed to visible and/or near infrared light. This exposure of the Functional cross-linked nanostructures to light may occur at any appropriate time but preferably occurs while the Functional cross-linked nanostructures is located in the body. Due to this exposure of the Functional cross-linked nanostructures to the visible and/or infrared light, the Functional cross-linked nanostructures emits spectral energy (e.g., visible and/or near infrared light) that may be detected by appropriate detection equipment. The spectral energy emitted from the Functional cross-linked nanostructures tends to exhibit a wavelength range greater than a wavelength range absorbed by the Functional cross-linked nanostructures. For example, if the Functional cross-linked nanostructures absorbs light of about 700 nm, the Functional cross-linked nanostructures may emit light of about 745 nm.

Detection of the Functional cross-linked nanostructures (or more particularly, light emitted therefrom) may be achieved through optical fluorescence, absorbance or light scattering procedures known in the art. This detection of the emitted spectral energy, or luminescence, may be characterized as a collection of the emitted spectral energy and a generation of electrical signal indicative of the collected spectral energy. For these purposes, the term "luminescence" refers to the emission of light from excited electronic states of atoms or molecules. Luminescence generally refers to light emission, such as photoluminescence, chemiluminescence, and electrochemiluminescence, among others. In photoluminescence, including fluorescence and phosphorescence, the excited electronic state is created by the absorption of electromagnetic radiation. Luminescence detection involves detection of one or more properties of the luminescence or associated luminescence process. These properties may include intensity, excitation and/or emission spectrum, polarization, lifetime, and energy transfer, among others. These properties may also include time-independent (steady-state) and/or time-dependent (time-resolved) properties of the luminescence. Representative luminescence techniques include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), optical-acoustic tomography (OAT) and bioluminescence resonance energy transfer (BRET), multiphoton technology, among others.

By way of example, when a compound is used in the present invention, it is desirable that the wavelength of light supplied to the compound be such that it excites the compound. This excitation causes the molecule to emit part of the absorbed energy at a different wavelength, and the emission can be detected using fluorometric techniques or other techniques as described above. One skilled in the art can readily determine the most appropriate detection technique based on, in part, the specific compound(s) administered, the particular use (e.g., tissue to be detected) and other aspects, including physical limitations of the analysis.

The techniques utilized to detect the spectral energy from the Functional cross-linked nanostructures that is present in the body may be designed to detect only selected wavelengths (or wavelength ranges) and/or may include one or more appropriate spectral filters. Various catheters, endoscopes, ear clips, headbands, surface coils, finger probes, and the like may be utilized to expose the Functional cross-linked nanostructures to light and/or to detect light emitting therefrom. This detection of spectral energy may be accomplished at one or more times intermittently or may be substantially continuous.

Preferably, non-ionizing energy is administered to the subject or sample for detecting or imaging a biological sample to a compound of the invention. For these purposes, the term "non-ionizing energy" generally refers to electromagnetic radiation that does not carry enough energy to completely remove at least one electron from an atom or molecule of the patient's body. For example, in some embodiments, non-ionizing energy may include spectral energy ranging in wavelength from about 400 nm to about 1200 nm. In some embodiments, non-ionizing energy may simply include visible and/or near infrared light.

In one embodiment, the spectral properties of the compounds of the invention may be tuned to desired wavelength ranges for excitation and/or emission. This may be useful, for example, in developing a particular imaging technique using a known excitation source.

References

J. Xu, G. Sun, R. Rossin, A. Hagooly, Z. Li, K-I, Fukukawa, B. W. Messmore, D. A. Moore, M. J. Welch, C. J. Hawker, K. L. Wooley, "Labeling of polymer nanostructures for medical imaging: importance of cross-linking extent, spacer length, and charge density," Macromolecules. 40, 2971-2973 (2007).

Q. Ma, E. E. Remsem, T. Kowalewski, J. Schaefer, K. L. Wooley, "Environmentally-responsive, entirely hydrophilic, shell-cross-linked (SCK) nanoparticles," Nano Lett. 1, 651-655 (2001).

H. Cui, Z. Chen, S. Zhong, K. L. Wooley, D. J. Pochan, "Block copolymer assembly via kinetic control," Science. 317, 647-650 (2007).

D. Benoit, V. Chaplinski, R. Braslau, C. J. Hawker, "Development of a universal alkoxyamine for "living" free radical polymerizations," J. Am. Chem. Soc. 121, 3904-3920 (1999).

Joralemon, M. J.; O'Reilly, R. K.; Hawker, C. J.; Wooley K. L. J. Am. Chem. Soc. 2005, 127, 16892-16899.

Li, Yali; Sun, Guorong; Xu, Jinqi; Wooley, Karen L. Nanotechnology in Therapeutics (2007), 381-407.

Kai Qi, Qinggao Ma, Edward E. Remsen, Christopher G. Clark, Jr., Karen Wooley J. Am. Chem. Soc., 2004, 126, 6599.

Qi Zhang, Edward Remsen, Karen Wooley, J. Am. Chem. Soc. 2000, 122, 3642.

Greenspan, P; Fowler, S. D., Journal of Lipid Research 1985, 26, 781.

M. Barzoukas, M. Blanchard-Desce, J. Chem. Phys. 2000, 113, 3951.

R. K. O'Reilly, C. J. Hawker, K. L. Wooley, Chem. Soc. Rev., 2006, 35, 1068-1083.

A. Walther, A. S. Goldmann, R. S. Yelamanchili, M. Drechsler, H. Schmalz, A. Eisenberg, A. H. E. Müller, Macromolecules, 2008, 41, 3254-3260.

Z. Li, E. Kesselman, Y. Talmon, M. A. Hillmyer, T. P. Lodge, Science, 2004, 306, 98-101.

I. W. Hamley, Nanotechnology, 2003, 14, R39-R54.

S. Liu, S. P. Armes, Angew. Chem. Int. Ed. 2002, 41, 1413-1416.

B. P. Binks, R. Murakami, S. P. Armes, S. Fujii, Angew. Chem. Int. Ed. 2005, 44, 4795-4798.

H. Huang; T. Kowalewski; E. E. Remsen; R. Gertzmann; K. L. Wooley, J. Am. Chem. Soc., 1997, 119, 11653-11659.

V. L. Alexeev, A. C. Sharma, A. V. Goponenko, S. Das, I. K. Lednev, C. S. Wilcox, D. N. Finegold, S. A. Asher, Anal. Chem. 2003, 75, 2316-2323.

X. Xu, A. V. Goponenko, S. A. Asher, J. Am. Chem. Soc. 2008, 130, 3113-3119.

WO 2009/061473
U.S. Pat. No. 6,383,500
U.S. Pat. No. 5,429,826
WO 2008/105773
WO 2007/133807
U.S. Pat. No. 7,682,603
Soft Matter, 2009, 5, 3422-3429 shell comprises the hydrophilic blocks of the block copolymers, wherein the therapeutic agent is at least partially encapsulated by the supramolecular structure and the therapeutic agent is non-covalently associated with the hydrophobic core, and wherein the optical agent is a shell-cross linked rod-shaped nanostructure.

2. The optical agent of claim 1 wherein the one or more photoactive moieties comprise one or more fluorophores capable of excitation upon absorption of electromagnetic radiation having wavelengths selected over a range of 400 nanometers to 1300 nanometers, and capable of emission of electromagnetic radiation having wavelengths selected over a range of 400 nanometers to 1300 nanometers.

3. The optical agent of claim 1 wherein the one or more photoactive moieties comprises a Type I or Type II phototherapeutic agent.

4. The optical agent of claim 1 wherein the one or more photoactive moieties comprises a pyrazine.

5. The optical agent of claim 1 wherein the mole ratio of the linking groups to monomers of the hydrophilic blocks is selected over a range of 1:100 to 99:100.

6. The optical agent of claim 1 wherein the block copolymers are diblock copolymers, triblock copolymers, polyblock copolymers or graft colymers.

What is claimed is:

1. An optical agent comprising:
an optical agent comprising cross linked block copolymers, wherein each of the block copolymers comprises a hydrophilic block and a hydrophobic block; and
linking groups covalently cross linking at least a portion of the hydrophilic blocks of the block copolymers, wherein at least a portion of the linking groups comprise one or more photoactive moieties; and
a therapeutic agent that is a cytotoxic moiety, a DNA intercalating anthracycline, a chemotherapy agent, an alkylating agent, a DNA intercalator, a microtubule-targeting molecule, a folate antagonist, a nucleoside antimetabolite, an antineoplastic agent, a platinum complex, a Taxol, a Type I photodynamic compound or a Type II photodynamic compound;
wherein the optical agent forms a supramolecular structure in aqueous solution, the supramolecular structure having an interior hydrophobic core and a covalently cross linked hydrophilic shell, wherein the interior hydrophobic core comprises the hydrophobic blocks of the block copolymers, and the covalently cross linked hydrophilic 7. The optical agent of claim 1 wherein the hydrophobic block is a poly(p-hydroxystyrene) polymer block; a polystyrene polymer block; a poly(p-hydroxystyrene) polymer block; a polyacrylate polymer block; a poly(propylene glycol) polymer block; a poly(ester) polymer block; a polylactic acid polymer block; a poly(tert-butylacrylate) polymer block; a poly(N-acryloxysuccinimide) polymer block; a poly(methyl acrylate) polymer block; a poly(ε-caprolactone) polymer block; a poly(glycolic acid) polymer block; a polylactide polymer block; or a polyglycolide polymer block; or a copolymer thereof.

8. The optical agent of claim 1 wherein the hydrophilic block is a poly(acrylic acid) polymer block; a poly(ethylene glycol) polymer block; a poly(acetoxystyrene) polymer block; or a copolymer thereof.

9. The optical agent of claim 1 wherein a hydrophilic block is a poly(acrylic acid) polymer block, a hydrophobic block is a poly(p-hydroxystyrene) block and the linking groups are bound to monomers of the poly(acrylic acid) polymer block by amide bonds.

10. The optical agent of claim 1 wherein at least a portion of the hydrophilic blocks of the block copolymers and linking groups have the formula:

(FX2)

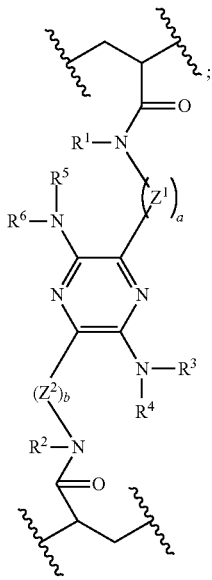

wherein each of $R^1$-$R^6$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group or a natural or non-natural amino acid or fragment thereof; each of $Z^1$ and $Z^2$ is independently

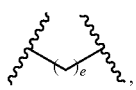

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein each e is independently is selected from the range of 0 to 10; and each of a and b is independently 0 or 1; or wherein at least a portion of the hydrophilic blocks of the block copolymers and linking groups have the formula:

(FX3)

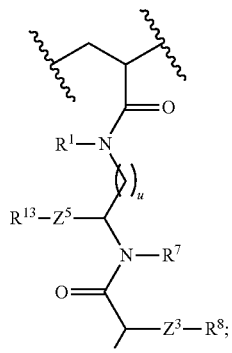

-continued

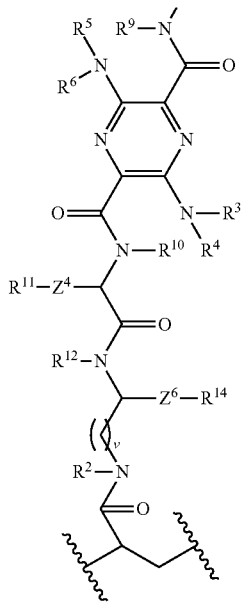

wherein each of $R^1$-$R^{14}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alykl, $C_5$-$C_{20}$ aryl, $C_1$-$C_{20}$ carbonyl, $C_2$-$C_{20}$ alkenyl, $C_5$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group or a natural or non-natural amino acid or fragment thereof; each of u and v is independently selected from the range of 0 to 10; each of $Z^3$-$Z^6$ is independently

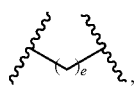

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein each e is independently is selected from the range of 0 to 10.

11. The optical agent of claim 10 wherein at least one of $R^8$, $R^{11}$, $R^{13}$, and $R^{14}$ is:

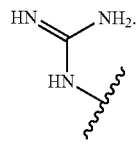

12. The optical agent of claim 1 wherein at least a portion of the hydrophilic blocks of the block copolymers and linking groups have the formula:

(FX11)

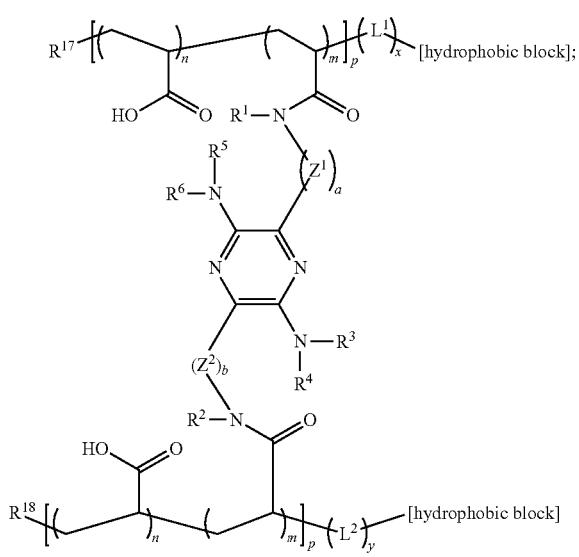

wherein each p is selected from the range of 20 to 250, wherein independently for each value of p, n is independently a number from 1 to 0 and m is independently a number from 1 to 0; wherein each of $R^1$-$R^6$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group or a natural or non-natural amino acid or fragment thereof; each of $R^{17}$ and $R^{18}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group, a natural or non-natural amino acid or fragment thereof or an additional hydrophilic block of the copolymers; each of $Z^1$, $Z^2$, $L^1$ and $L^2$ is independently

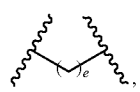

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein each e is independently selected from the range of 0 to 10; each of a and b is independently 0 or 1; wherein [hydrophobic block] is a hydrophobic block of the block copolymers; wherein each of x and y is independently 0 or 1; or wherein at least a portion of the hydrophilic blocks of the block copolymers and linking groups have the formula:

(FX14)

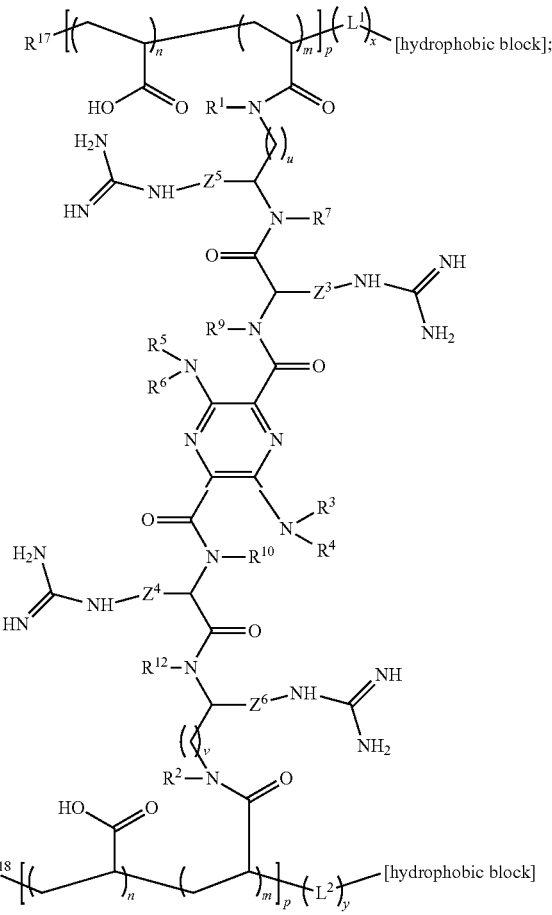

wherein each p is selected from the range of 20 to 250, wherein independently for each value of p, n is independently a number from 1 to 0 and m is independently a number from 1 to 0; wherein each of $R^1$-$R^7$, $R^9$, $R^{10}$, and $R^{12}$-$R^{14}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo amine amide hydroxyl, carboxyl, cyano a nitrile group an azide group, a nitro group, an acyl group, a thiol group or a natural or non-natural amino acid or fragment thereof; each of $R^{17}$ and $R^{18}$ is independently selected from the group consisting of —R, —COOR, —COR, —CON(R)$_2$, —OCON(R)$_2$, —N(R)$_2$, —SR, —SO$_2$R, —SOR, —OCOOR, —SO$_2$N(R)$_2$, and —OR; each R is independently selected from the group consisting of a hydrogen, $C_1$-$C_{20}$ alkyl, $C_5$-$C_{20}$ aryl, $C_1$-$C_{20}$ carbonyl, $C_2$-$C_{20}$ alkenyl, $C_2$-$C_{20}$ alkynyl, $C_5$-$C_{20}$ alkylaryl, $C_1$-$C_{20}$ alkoxy, halo, amine, amide, hydroxyl, carboxyl, cyano, a nitrile group, an azide group, a nitro group, an acyl group, a thiol group, a natural or non-natural amino acid or fragment thereof or an additional hydrophilic block of the copolymers; each of $Z^3$-$Z^6$, $L^1$ and $L^2$ is independently

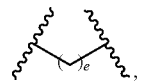

wherein one or more CH$_2$ groups may be replaced by NH, O, S, a carbonyl (C=O), or a sulfonyl (S=O or O=S=O); two adjacent CH$_2$ groups may be replaced by —CH=CH— or —C≡C—; and wherein each e is independently selected from the range of 0 to 10; each of u and v is independently selected from the range of 0 to 10; wherein [hydrophobic block) is a hydrophobic block of the block copolymers; wherein each of x and y is independently 0 or 1.

13. The optical agent of claim 1 further comprising one or more targeting moieties bonded to the hydrophilic blocks of at least a portion of the block copolymers, wherein the targeting moiety is a peptide, a protein, a ST receptor binding agent, a bombesin receptor binding agent, a leukemia peptide, and a folate receptor binding agent, an oligonucleotide, an antibody, a carbohydrate, a hormone, a lipid or a drug.

14. An optical agent of claim 1 for use in a tandem optical imaging and therapeutic procedure, the procedure comprising:
    administering to a mammal an effective amount of the optical agent of claim 1, wherein the one or more photoactive moieties comprise one or more chromophores and/or fluorophores, wherein the therapeutic agent is released from the supramolecular structure;
    exposing the optical agent administered to the mammal to electromagnetic radiation; and detecting electromagnetic radiation transmitted, scattered or emitted by the optical agent.

15. A shell-cross linked micelle comprising:
    cross linked block copolymers, wherein each of the block copolymers comprises a poly(acrylic acid) polymer block directly or indirectly bonded to a hydrophobic block; pyrazine-containing linking groups covalently cross linking at least a portion of the poly(acrylic acid) polymer blocks of the block copolymers, wherein the copolymers form a supramolecular structure;
    a therapeutic agent that is a cytotoxic moiety, a DNA intercalating anthracycline, a chemotherapy agent, an alkylating agent, a DNA intercalator, a microtubule-targeting molecule, a folate antagonist, a nucleoside antimetabolite, an antineoplastic agent, a platinum complex, a Taxol, a Type I photodynamic compound or a Type II photodynamic compound, wherein the therapeutic agent is at least partially encapsulated by the supramolecular structure wherein the mole ratio of the pyrazine-containing linking groups to monomers of the poly(acrylic acid) polymer block is selected over a range of 1:100 to 99:100.

16. The compound of claim 1 and at least one carrier or excipient resulting in a pharmaceutically acceptable composition.

17. A pharmaceutically acceptable composition comprising at least
    one carrier or excipient and an optical agent comprising:
    an optical agent comprising cross linked block copolymers, wherein each of the block copolymers comprises a hydrophilic block and a hydrophobic block; and
    linking groups covalently cross linking at least a portion of the hydrophilic blocks of the block copolymers, wherein at least a portion of the linking groups comprise one or more photoactive moieties; and
    a therapeutic agent that is a cytotoxic moiety, a DNA intercalating anthracycline, a chemotherapy agent, an alkylating agent, a DNA intercalator, a microtubule-targeting molecule, a folate antagonist, a nucleoside antimetabolite, an antineoplastic agent, a platinum complex, a Taxol, a Type I photodynamic compound or a Type II photodynamic compound;
    wherein the optical agent forms a supramolecular structure in aqueous solution, the supramolecular structure having an interior hydrophobic core and a covalently cross linked hydrophilic shell, wherein the interior hydrophobic core comprises the hydrophobic blocks of the block copolymers, and the covalently cross linked hydrophilic shell comprises the hydrophilic blocks of the block copolymers, and wherein the therapeutic agent is at least partially encapsulated by the supramolecular structure and the therapeutic agent is non-covalently associated with the hydrophobic core.

18. An optical agent of claim 1, wherein the therapeutic agent is doxorubicin or paclitaxel.

19. A shell-cross linked micelle of claim 15, wherein the therapeutic agent is doxorubicin or paclitaxel.

20. A composition according to claim 17, wherein the therapeutic agent is doxorubicin or paclitaxel.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: synthesized peptide

<400> SEQUENCE: 1

Ser Phe Phe Tyr Leu Arg Ser
1               5
```